US012090146B2

United States Patent
Toop et al.

(10) Patent No.: US 12,090,146 B2
(45) Date of Patent: Sep. 17, 2024

(54) SUBSTITUTED-PYRIDINYL COMPOUNDS AND USES THEREOF

(71) Applicant: Bionomics Limited, Eastwood (AU)

(72) Inventors: Hamish Toop, Eastwood (AU); Rajinder Singh, Eastwood (AU); Erin Smith, Eastwood (AU); Dharam Paul, Eastwood (AU); Patrick Bazzini, Strasbourg (FR); Jean-Marie Contreras, Westhouse (FR); Christophe Morice, Widensolen (FR); Florence Chery, Strasbourg (FR); Fabrice Garrido, Illkirch (FR)

(73) Assignee: Bionomics Limited, Eastwood (AU)

( * ) Notice: Subject to any disclaimer, the term of this patent is extended or adjusted under 35 U.S.C. 154(b) by 729 days.

(21) Appl. No.: 17/276,605

(22) PCT Filed: Sep. 20, 2019

(86) PCT No.: PCT/AU2019/051013
§ 371 (c)(1),
(2) Date: Mar. 16, 2021

(87) PCT Pub. No.: WO2019/222816
PCT Pub. Date: Nov. 28, 2019

(65) Prior Publication Data
US 2022/0040163 A1  Feb. 10, 2022

(30) Foreign Application Priority Data

Sep. 21, 2018  (AU) .................. 2018903548

(51) Int. Cl.
*A61K 31/4439*  (2006.01)
*A61P 25/18*  (2006.01)
*A61P 25/28*  (2006.01)
*C07D 401/04*  (2006.01)

(52) U.S. Cl.
CPC ........ *A61K 31/4439* (2013.01); *C07D 401/04* (2013.01); *A61P 25/18* (2018.01); *A61P 25/28* (2018.01)

(58) Field of Classification Search
CPC ... A61K 31/4439; C07D 401/04; A61P 25/28; A61P 25/18
See application file for complete search history.

(56) References Cited

FOREIGN PATENT DOCUMENTS

| WO | 99-52892 A2 | 10/1999 |
|---|---|---|
| WO | 2011-069951 A1 | 6/2011 |
| WO | 2013-083994 A1 | 6/2013 |
| WO | 2013-175211 A1 | 11/2013 |
| WO | 2018-109484 A1 | 6/2018 |

OTHER PUBLICATIONS

Brown et al. Bioisosteres in Medicinal Chemistry—Chp 2, Wiley-VCH Verlag Gmbh & Co. KGaA, 2012, p. 15-29 (Year: 2012).*
International Search Report and Written Opinion mailed Nov. 1, 2019 in International Patent Application No. PCT/AU2019/051013 filed Sep. 20, 2019, 20 pages.

* cited by examiner

*Primary Examiner* — Noble E Jarrell
*Assistant Examiner* — Richard Grant Peckham
(74) *Attorney, Agent, or Firm* — Kilpatrick Townsend & Stockton LLP

(57) ABSTRACT

The present application relates generally to compounds useful for the treatment and/or enhancement of cognitive dysfunction and negative symptoms associated with CNS disorders where the circuitry involving fast spiking PV+ interneurons and the production of cortical gamma oscillations is disrupted. The subject disclosure enables the manufacture of medicaments as well as compositions containing same for use in methods of therapy and prophylaxis of cognitive dysfunction and negative symptoms.

12 Claims, No Drawings

SUBSTITUTED-PYRIDINYL COMPOUNDS AND USES THEREOF

FIELD

The present disclosure relates generally to compounds useful for the treatment and/or enhancement of cognitive dysfunction and negative symptoms associated with CNS disorders where the circuitry involving fast spiking PV+ interneurons and the production of cortical gamma oscillations is disrupted. The subject disclosure enables the manufacture of medicaments as well as compositions containing same for use in methods of therapy and prophylaxis of cognitive dysfunction and negative symptoms.

BACKGROUND

The Kv3 voltage-gated potassium channels Kv3.1-Kv3.4, encoded by the KCNC1-4 genes, are responsible for the neurons ability for fast repolarization, thereby facilitating high-frequency action potential firing. Due to these fast activating properties, Kv3 channels are believed to be important in setting and controlling firing frequency in fast spiking neurons.

Hence the Kv3 channels are thought to play a pivotal role in cortical neuronal networks to produce synchronized gamma (γ) frequency oscillations (30-80 Hz). When synchronized across neuronal populations, these γ oscillations are associated with productive cognitive and behavioral responses; their dysfunction is thought to be relevant for cognitive disorders and negative symptoms. Specifically, the fast-spiking interneurons involved in generating gamma synchrony are those that express the calcium-binding protein, parvalbumin (PV).

The Kv3.1 and Kv3.2 subunits are expressed in PV positive fast spiking GABAergic interneurons and are involved in the rapid action potential firing of these interneurons to orchestrate the activity of cortical networks.

Studies in patients suffering from schizophrenia and in animal models of the condition, have shown an inability of cortical networks to generate coherent gamma frequency oscillations. In addition, post-mortem studies using cortical tissue obtained from patients with schizophrenia report reductions in PV and in the expression of Kv3.1 channels in the remaining PV positive interneurons. In addition, PV interneuron dysfunction leading to dysfunctional gamma oscillations is implicated in several pathologies associated with cognitive dysfunction and negative symptoms where the circuitry involving fast spiking PV+ interneurons and the production of cortical gamma oscillations is disrupted: schizophrenia, Alzheimer's disease, Tourette's syndrome, autism, dementia, epilepsy.

Hence, pharmacological manipulation of Kv3.1 and/or Kv3.2 channels, represents a possible method for treating cognitive dysfunction and negative symptoms associated with central nervous system disorders where the circuitry involving fast spiking PV+ interneurons and the production of cortical gamma oscillations is dysfunctional. Small molecules that positively modulate Kv3.1 and/or Kv3.2, by restoring fast-spiking properties to PV interneurons, represent a novel therapeutic treatment for cognitive dysfunction and negative symptoms.

SUMMARY

The instant disclosure teaches that compounds of the invention including subformulae thereof, are activators of Kv3.1 and/or Kv3.2 channels and are therefore therapeutically useful in the treatment of cognitive dysfunction and negative symptoms associated with central nervous system disorders such as schizophrenia, Alzheimer's disease, Tourette's syndrome, autism, dementia, epilepsy and other disorders where gamma oscillations are dysfunctional.

In one aspect the invention provides methods of treating cognitive dysfunction and negative symptoms associated with CNS disorders where the circuitry involving fast spiking PV+ interneurons and the production of cortical gamma oscillations is disrupted in a subject in need thereof including the step of administering to a patient an effective amount of a compound of formula (I):

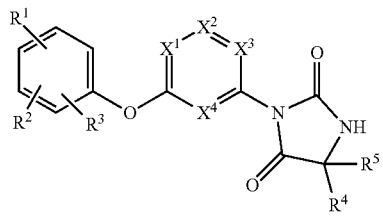

(I)

wherein:
one of $X^1$, $X^2$, $X^3$ or $X^4$ is N and the others are independently selected from CH, CF, $CCF_3$, CCl, $CCH_3$ or $COCF_3$;
$R^1$ is phenyl, CN, F, $OCF_3$, $C_1$-$C_3$ alkoxy or $C_1$-$C_5$ alkyl;
$R^2$ is H, $C_1$-$C_5$ alkyl or $C_1$-$C_5$ alkoxy;
$R^3$ is H or $CH_3$; or
$R^1$ and $R^2$ together represent an optionally substituted 5 or 6-membered O-containing heterocyclylene, optionally substituted 5 or 6-membered O-containing heteroarylene, or optionally substituted 5 or 6-membered arylene; and
$R^4$ and $R^5$ are independently H or $C_1$-$C_4$ alkyl, or $R^4$ and $R^5$ together represent an optionally substituted 4-7 membered cycloalkylene or optionally substituted 5-7 membered heterocyclylene;
or a pharmaceutically acceptable salt, solvate or prodrug thereof, and stereoisomers thereof.

In another aspect the invention provides compounds of formula (I'):

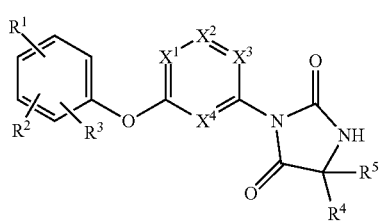

(I')

wherein:
one of $X^1$, $X^2$, $X^3$ or $X^4$ is N and the others are independently selected from CH, CF, $CCF_3$, $CCH_3$ or $COCF_3$;
$R^1$ is phenyl, CN, F, $OCF_3$, $C_1$-$C_3$ alkoxy or $C_1$-$C_5$ alkyl;
$R^2$ is H, $C_1$-$C_5$ alkyl or $C_1$-$C_5$ alkoxy;
$R^3$ is H or $CH_3$; or
$R^1$ and $R^2$ together represent an optionally substituted 5 or 6-membered O-containing heterocyclylene, optionally substituted 5 or 6-membered O-containing heteroarylene, or optionally substituted 5 or 6-membered arylene; and $R^4$ and $R^5$ are independently H or $C_1$-$C_4$ alkyl, or $R^4$ and $R^5$ together represent an optionally substituted 4-7 membered cycloalkylene or optionally substituted 5-7 membered heterocyclylene;

or a pharmaceutically acceptable salt, solvate or prodrug thereof, and stereoisomers thereof.

In certain embodiments:

$R^1$ is CN, F, $OCF_3$, $C_1$-$C_3$ alkoxy or $C_1$-$C_5$ alkyl; and
$R^2$ is $C_1$-$C_5$ alkyl or $C_1$-$C_5$ alkoxy; or
$R^1$ and $R^2$ together represent an optionally substituted 5-membered O-containing heterocyclyl.

In certain embodiments the compound of formula (I') is a compound of formula (I'a), (I'b), (I'c), or (I'd):

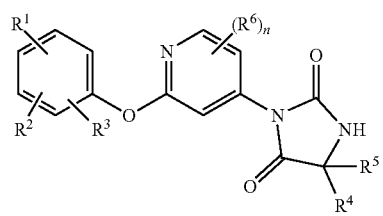

(I'a)

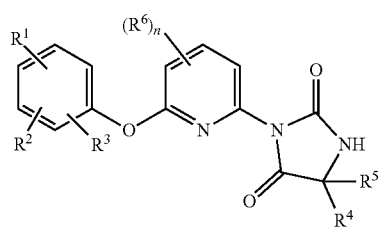

(I'b)

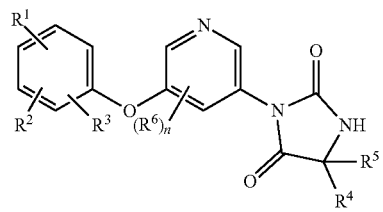

(I'c)

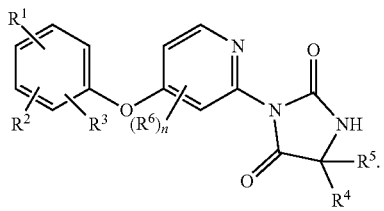

(I'd)

wherein $R^1$ to $R^5$ are as defined above, $R^6$ is independently selected from $OF_3$, $CF_3$, F, or $CH_3$, and n is 0, 1, or 2.

In an embodiment the compound of formula (I') is a compound of formula (I'a).

In a further embodiment the compound of formula (I') is selected from a compound of formula (I'a)-(I'd) in which $R^4$ and $R^5$ together represent an optionally substituted 4-7 membered cycloalkylene or optionally substituted 5-7 membered heterocyclylene.

The present invention also provides the use of a compound of formula (I):

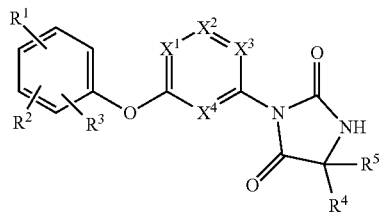

(I)

wherein:

one of $X^1$, $X^2$, $X^3$ or $X^4$ is N and the others are independently selected from CH, CF, $CCF_3$, CCl, $CCH_3$ or $COCF_3$;

$R^1$ is phenyl, CN, F, $OCF_3$, $C_1$-$C_3$ alkoxy or $C_1$-$C_5$ alkyl;
$R^2$ is H, $C_1$-$C_5$ alkyl or $C_1$-$C_5$ alkoxy;
$R^3$ is H or $CH_3$; or
$R^1$ and $R^2$ together represent an optionally substituted 5 or 6-membered O-containing heterocyclylene, optionally substituted 5 or 6-membered O-containing heteroarylene, or optionally substituted 5 or 6-membered arylene; and $R^4$ and $R^5$ are independently H or $C_1$-$C_4$ alkyl, or $R^4$ and $R^5$ together represent an optionally substituted 4-7 membered cycloalkylene or optionally substituted 5-7 membered heterocyclylene;

or a pharmaceutically acceptable salt, solvate or prodrug thereof, and stereoisomers thereof, in the manufacture of a medicament for the treatment of cognitive dysfunction and negative symptoms associated with CNS disorders where the circuitry involving fast spiking PV+ interneurons and the production of cortical gamma oscillations is disrupted.

The present invention also provides the use of a compound of formula (I):

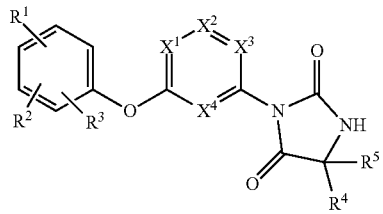

(I)

wherein:

one of $X^1$, $X^2$, $X^3$ or $X^4$ is N and the others are independently selected from CH, CF, $CCF_3$, CCl, $CCH_3$ or $COCF_3$;

$R^1$ is phenyl, CN, F, $OCF_3$, $C_1$-$C_3$ alkoxy or $C_1$-$C_5$ alkyl;
$R^2$ is H, $C_1$-$C_5$ alkyl or $C_1$-$C_5$ alkoxy;
$R^3$ is H or $CH_3$; or
$R^1$ and $R^2$ together represent an optionally substituted 5 or 6-membered O-containing heterocyclylene, optionally substituted 5 or 6-membered O-containing heteroarylene, or optionally substituted 5 or 6-membered arylene; and $R^4$ and $R^5$ are independently H or $C_1$-$C_4$ alkyl, or $R^4$ and $R^5$ together represent an optionally substituted 4-7 membered cycloalkylene or optionally substituted 5-7 membered heterocyclylene;

or a pharmaceutically acceptable salt, solvate or prodrug thereof, and stereoisomers thereof, for the treatment of cognitive dysfunction and negative symptoms associated with CNS disorders where the circuitry involving fast spiking PV+ interneurons and the production of cortical gamma oscillations is disrupted.

DETAILED DESCRIPTION OF THE INVENTION

The present disclosure contemplates the treatment of cognitive dysfunction and negative symptoms associated with CNS disorders where the circuitry involving fast spiking PV+ interneurons and the production of cortical gamma oscillations is disrupted.

It is proposed herein that the compounds of formula (I), and subformulae thereof, treat cognitive dysfunction and negative symptoms associated with CNS disorders where the circuitry involving fast spiking PV+ interneurons and the production of cortical gamma oscillations is disrupted.

The invention is based on the discovery that particular 1,3 meta-disposed hydantoin substituted pyridinyl compounds of the general formula (I) as shown below,

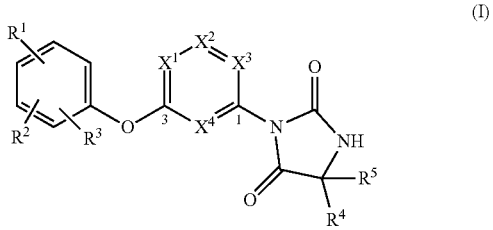

(wherein $R^1$-$R^5$ are as defined hereinbefore)
have useful properties as activators of the Kv3.1 and/or Kv3.2 channels and are able to elicit an effect on the central nervous system. Such compounds have significant potential for the treatment of cognitive dysfunction and negative symptoms associated with CNS disorders where the circuitry involving fast spiking PV+ interneurons and the production of cortical gamma oscillations is disrupted. For example, in schizophrenia, Alzheimer's disease, Tourette's syndrome, autism and other dementias.

Cognitive dysfunction or impairment refers to a category of mental health disorders that primarily affect cognitive abilities including learning, memory, perception, and problem solving. They are defined by deficits in cognitive ability that are acquired (as opposed to developmental), typically represent decline, and may have an underlying brain pathology.

The instant compounds have been shown to treat a specific underlying pathology ie "where the circuitry involving fast spiking PV+ interneurons and the production of cortical gamma oscillations is disrupted".

The DSM-5 defines six key domains of cognitive function: executive function, learning and memory, perceptual-motor function, language, complex attention, and social cognition. Cognition dysfunction or impairment may be diagnosed and assessed based on the six-item cognitive impairment test (6-CIT) Kingshill Version 2000.

"Alkyl" refers to a saturated monovalent hydrocarbon radical which may be straight chained or branched and preferably have from 1 to 5 carbon atoms or more preferably 1 to 4 (i.e., for instance $C_1$-$C_4$ alkyl). Examples of such alkyl groups include methyl, ethyl, n-propyl, iso-propyl, n-butyl and iso-butyl.

"Alkoxy" refers to the group alkyl-O— where the alkyl group is as described above but restricted to $C_1$-$C_3$ alkoxy. Examples include methoxy, ethoxy and n-propoxy.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

The most preferred heteroatom is nitrogen.

"Heterocyclylene" refers to a divalent heterocyclyl group wherein the heterocyclyl group is as described above.

"Heteroaryl" refers to a monovalent aromatic heterocyclic group which fulfils the Hückel criteria for aromaticity (i.e., contains 4n+2 π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (e.g., pyridyl, pyrrolyl or N-oxides thereof or furyl) or multiple condensed rings (e.g., indolizinyl, benzoimidazolyl, coumarinyl, quinolinyl, isoquinolinyl or benzothienyl).

"Heteroarylene" refers to a divalent heteroaryl group wherein the heteroaryl group is as described above.

"Cycloalkylene" refers to a divalent cycloalkyl group which is defined as a saturated divalent cyclic hydrocarbon radical and preferably have from 3 to 7 carbon atoms or more preferably 4 to 6. Examples of such groups include cyclopropylene, cyclobutylene, etc.

In this specification "optionally substituted" is taken to mean that a group may or may not be further substituted. The term "optionally substituted" is taken to mean that the groups may be substituted from 1 to 3 times independently selected from the groups consisting of hydroxy, halogen (in particular Cl, Br, F), $C_{1-6}$ alkyl, $C_{1-6}$ alkoxy, $C_{2-6}$ alkenyl, $C_{1-6}$ haloalkyl (in particular —$CF_3$), $C_{1-6}$ haloalkoxy (such as —$OCF_3$), arylalkyl (wherein alkyl is $C_{1-6}$), arylalkoxy (wherein alkyl is $C_{1-6}$), aryl, cyano, nitro, heteroaryl, trialkylsilyl, amino, mono- and di-alkylamino, mono- and di-(substituted alkyl)amino, and mono- and di-arylamino.

In still further embodiments, the term "optionally substituted" is taken to mean that the groups may be substituted from 1 to 3 times independently selected from the groups consisting of hydroxy, halogen (in particular Cl, Br, F), hydroxethyl, hydroxpropyl, methyl, methoxy, cyano, pyridinyl, pyridinylmethyl, pyrazinyl, methylphenyl, benzyl, trimethylsilyl, phenyl, methylpyrazoyl, dimethylamino, fluorophenyl, tert-butyloxycarbonyl, amino or morpholinyl.

In the context of $R^1$ and $R^2$ together being an "optionally substituted" 5-membered O-containing heteroarylene, for instance, the present invention contemplates embodiments where $R^1$ and $R^2$ together are an optionally substituted furanylene ring. In an embodiment $R^1$ and $R^2$ together are an optionally substituted furanylene ring wherein the optional substituents are selected from F, $CH_3$ and $CF_3$. In an embodiment $R^1$ and $R^2$ together represent a moiety of formula (IIa-IIf):

(II)

(a) 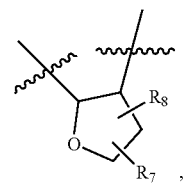

(b) 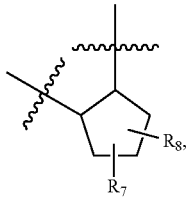

(c) 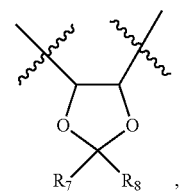

(d) 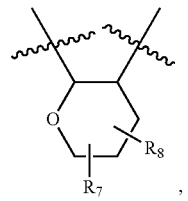

(e) 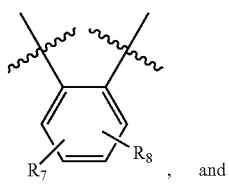, and (f) 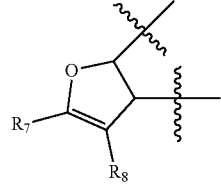

wherein $R_7$ and $R_8$ are independently selected from H, F, $CH_3$ and $CF_3$.

In a further embodiment and with reference to subformulae II(a)-II(f), $R_7$ and $R_8$ are independently selected from F, $CH_3$ and $CF_3$.

In an embodiment $R_1$ is $CH_3$.
In an embodiment $R_1$ is $OCH_3$.
In an embodiment $R_2$ is $CH_3$.
In an embodiment $R_2$ is $OCH_3$.
In an embodiment $R^1$ and $R^2$ together is an optionally substituted furanylene ring.
In an embodiment $R^1$ and $R^2$ together is an optionally substituted furanylene ring of formula II(f) wherein $R_7$ and $R_8$ are $CH_3$ and $CF_3$.
In an embodiment $R_4$ is $CH_3$ and $R_5$ is $CH_3$.
In an embodiment $R_4$ is $CH_3$ and $R_5$ is H.
In an embodiment $R_4$ is $CH_2CH_3$ and $R_5$ is H.
In an embodiment $R_4$ is $CH_2CH_3$ and $R_5$ is $CH_3$.
In an embodiment n is 1 and $R_6$ is F.
In a particular embodiment $R_1$ is disposed para to the ether moiety as represented below:

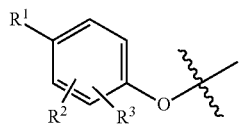

In certain other embodiments and with reference to compounds of formula (I), (I'), (I'a), (I'b) (I'c) or (I'd):
$R_1$ represents $OCH_3$ or $CH_3$;
$R_2$ represents $CH_3$ or $OCH_3$;
$R_3$ represents H;
$R_4$ represents $CH_3$ or $CH_2CH_3$;
$R_5$ is $CH_3$ or H; or
$R_4$ and $R_5$ together represent cyclopropylene, cyclobutylene, cyclopentylene or cyclohexylene; and
n is 1 and $R_6$ is F.

In certain embodiments representative

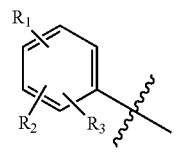

groups include:

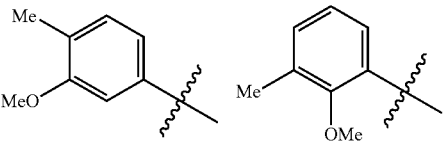

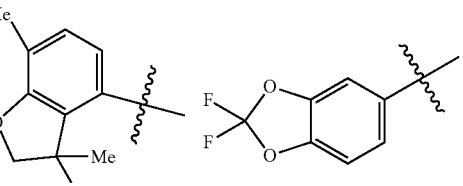

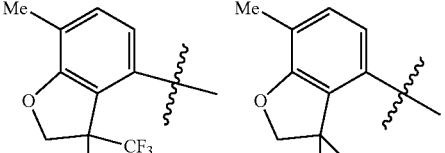

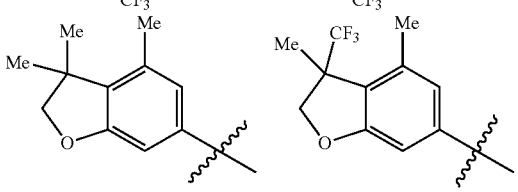

-continued

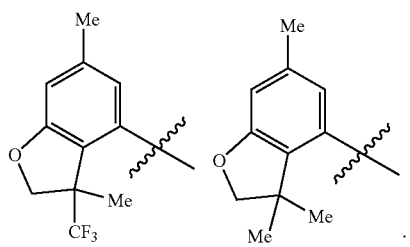

In a further embodiment the invention contemplates compounds of formula (II):

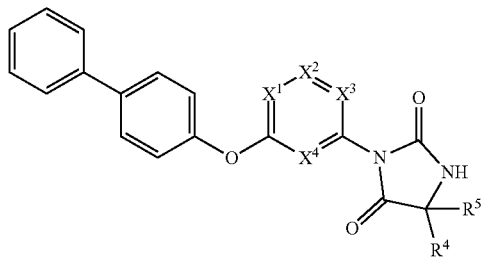

(II)

wherein $X^1$-$X^4$ and $R^4$ and $R^5$ are as defined for compounds of formula (I).

In a further embodiment the compounds of formula (I) are compounds of formula (I'a):

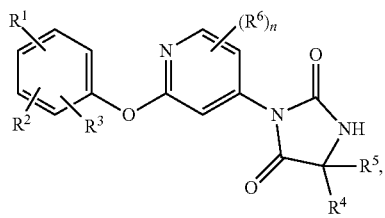

(I'a)

wherein $R^1$-$R^6$ and n are as defined above.

In still a further embodiment the compounds of formula (I) are compounds of formula (I"a):

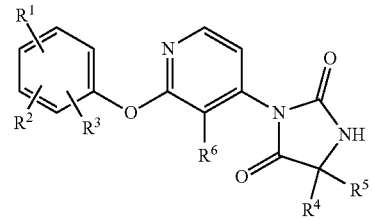

(I"a)

wherein $R^1$-$R^6$ are as defined above.

In yet still a further embodiment the compounds of formula (I) are compounds of formula (I"b):

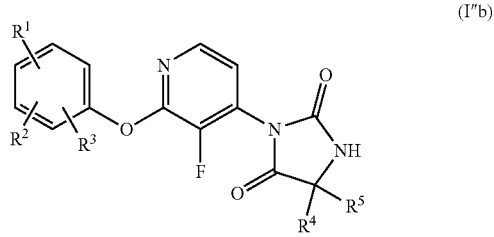

(I"b)

wherein $R^1$-$R^5$ are as defined above.

Representative compounds of the present invention and compounds which can be used in the methods of the present invention include as well as those exemplified herein:

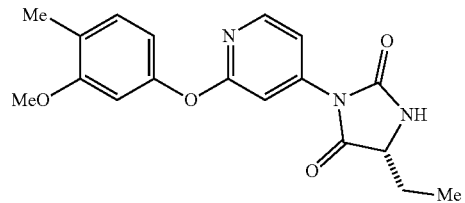

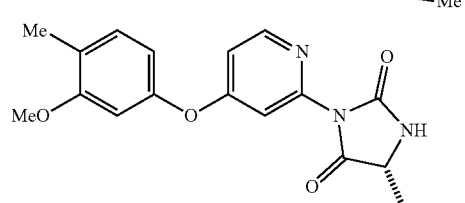

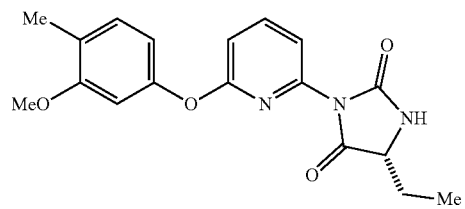

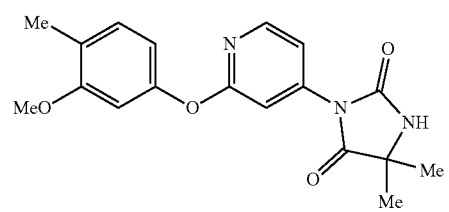

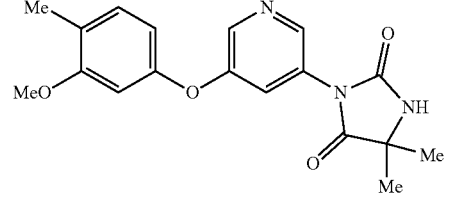

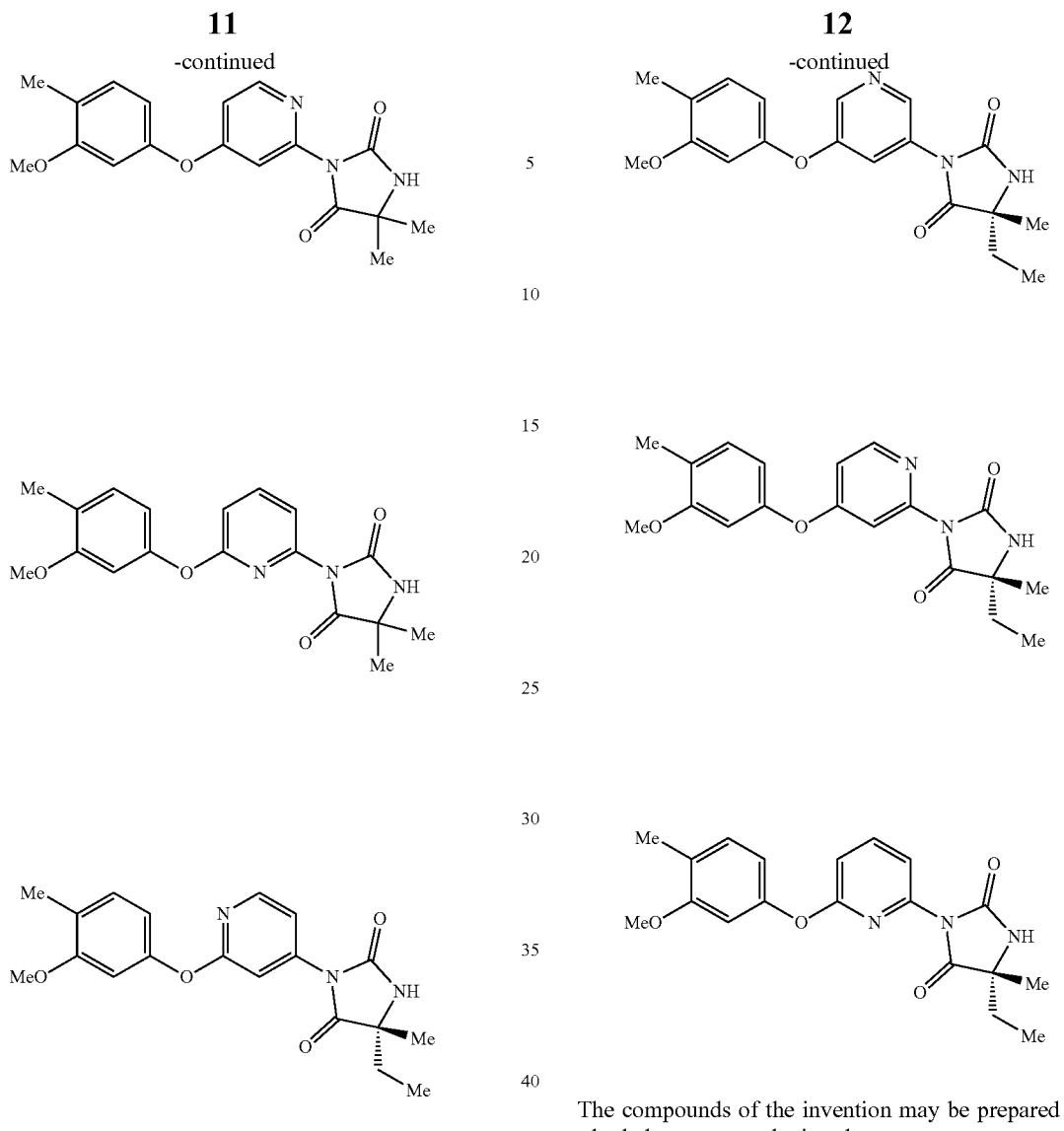
The compounds of the invention may be prepared based on the below retrosynthetic schemes.
Scheme 1
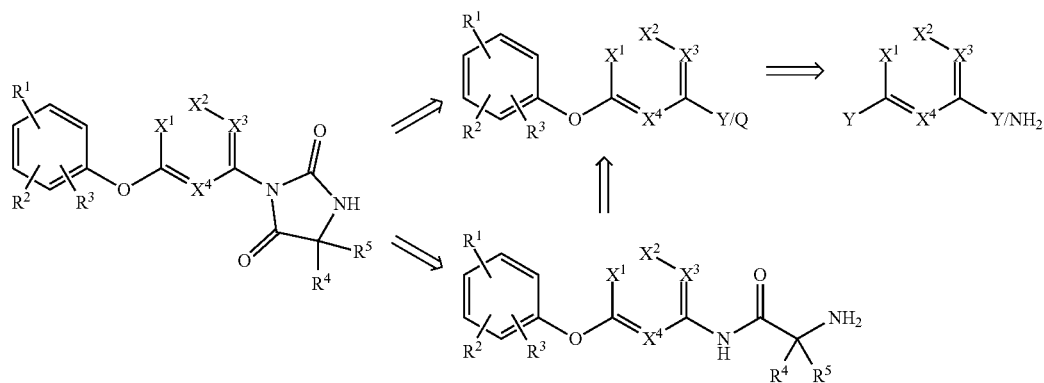
Y is a halgogen (F, Cl, Br or I)

Scheme 2

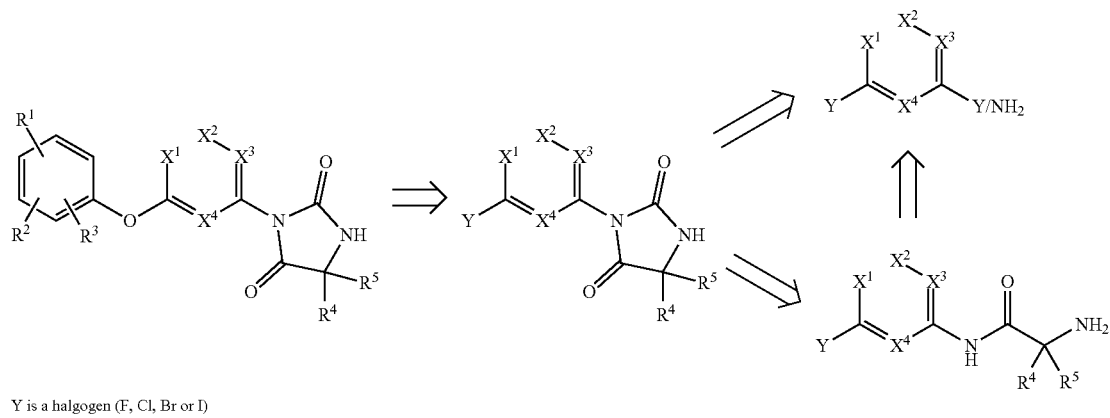

Y is a halgogen (F, Cl, Br or I)

Other compounds of formula (I) or (II) can be prepared by the addition, removal or modification of existing substituents. This could be achieved by using standard techniques for functional group inter-conversion that are well known in the industry, such as those described in "Comprehensive organic transformations: a guide to functional group preparations" by Larock R. C., New York, VCH Publishers, Inc. 1989.

One of ordinary skill in the art will appreciate that the synthetic methods, as described herein, may necessitate a variety of protecting groups. By the term "protecting group", as used herein, it is meant that a particular functional moiety, e.g., O, S, or N, is temporarily blocked so that a reaction can be carried out selectively at another reactive site in a multifunctional compound. Exemplary protecting groups are described in Protective Groups in Organic Synthesis, Third Ed. Greene, T. W. and Wuts, P. G., Eds., John Wiley & Sons, New York: 1999, the entire contents of which are hereby incorporated by reference.

In studies conducted by the inventors it has been demonstrated in animal models of spatial memory that compounds disclosed herein may be able to treat cognitive impairment (or dysfunction).

Taught herein, therefore, is the use of a compound of formula (I), (I'), (I'a), (I'b), (I'c) or (I'd) or an embodiment thereof described herein, or a pharmaceutically acceptable salt thereof, in the manufacture of a medicament for treating cognitive dysfunction and negative symptoms associated with CNS disorders where the circuitry involving fast spiking PV+ interneurons and the production of cortical gamma oscillations is disrupted in a subject in need thereof.

In other embodiments, the present compounds are administered to a subject in need thereof, together with traditional anti-psychotic drugs for a period of about 2-4 weeks, to address the symptoms of schizophrenia, with the option of discontinuing treatment with the present compounds whilst continuing with the traditional therapy. In other embodiments, the subject is treated with both a present compound and one or more traditional medications (administered sequentially or in combination) for the duration of the treatment period. Such combination therapy may be particularly useful, for example, where the combination of a present compound and one or more traditional anti-psychotic medications provides relief from schizophrenia in the acute lag phase of the treatment period and/or where an additive or synergistic antidepressant therapeutic effect is desired.

"Treat", "treating" or "treatment" with regard to the disorder refers to alleviating or abrogating the cause and/or the effects of the disorder. As used herein, the terms "treat", "treatment" and "treating" refer to the reduction or amelioration of the progression, severity and/or duration of condition, or the amelioration of one or more symptoms (e.g., one or more discernible symptoms) of said condition (i.e., "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of the disorder described herein. In other embodiments the terms "treat", "treatment" and "treating" refer to the inhibition of the progression of further cognitive impairment.

In certain embodiments, the present compounds of formula (I), (Ia), (Ib), (Ic), or (Id) or an embodiment thereof described herein, or a pharmaceutically acceptable salt thereof, are administered to said subject in combination with an anti-psychotic compound.

The compounds encompassed herein may also be used as a combination therapyacetylcholinesterase inhibitors (e.g., donepezil, galantamine, rivastigmine), atypical antipsychotics (e.g., risperidone, aripiprizole, quetiapine, olanzapine) and N-methyl-D-aspartate receptor (NMDAR) inhibitors (e.g., memantine).

The compounds enclosed herein are administered to the subject in a treatment effective amount. In some embodiments, a treatment effective amount is a therapeutically effective amount. The term "therapeutically effective amount" as used herein means that amount of active compound or pharmaceutical agent that elicits the biological or medicinal response in a tissue, system, animal or human that is being sought by a researcher, veterinarian, medical doctor, or other clinician. The therapeutically effective amount of the compound to be administered will be governed by such considerations, and is the minimum amount necessary to ameliorate, cure, or treat the disease or disorder or one or more of its symptoms. The term "prophylactically effective amount" refers to an amount effective in preventing or substantially lessening the chances of acquiring or in reducing the severity of the cognitive impairment before it is acquired or reducing the severity before the symptoms develop. secondary prophylaxis (whereby the disease or symptom has already developed and the patient is protected against worsening of this process).

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods.

In an embodiment, the method comprises administering to a subject in need thereof the present compound in a dosage to provide an effective amount in vivo that will improve cognition, including, but not limited to the acute stages of treatment (e.g., within 1, 2, 3, or 4 weeks from the commencement of treatment). Methods of determining an in vitro equivalent concentration of the present compounds would be familiar to the skilled artisan.

Thereafter, treatment with the present compounds may be continued throughout the treatment period or it may be ceased or replaced with traditional therapeutic compounds.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to, for example, a child or an adolescent (assuming it is approved for paediatric use) can be determined by a medical practitioner or person skilled in the art and can be lower or the same as that administered to an adult.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula (I), (Ia), (Ib), (Ic) or (Id) or a pharmaceutically acceptable salt thereof, and a second amount of an additional suitable therapeutic agent.

In certain embodiments, the compound of formula (I), (Ia), (Ib), (Ic) or (Id) as described herein, or a pharmaceutically acceptable salt thereof, and the additional therapeutic agent are each administered in an effective amount (i.e., each in an amount which would be therapeutically effective if administered alone). In other embodiments, the compound of formula ((I), (Ia), (Ib), (Ic) or (Id) as described herein, or a pharmaceutically acceptable salt thereof, and the additional therapeutic agent are each administered in an amount which alone does not provide a therapeutic effect (a sub-therapeutic dose). In yet other embodiments, the compound of formula (I), (Ia), (Ib), (Ic) or (Id) as described herein, or a pharmaceutically acceptable salt thereof can be administered in an effective amount, while the additional therapeutic agent is administered in a sub-therapeutic dose. In still other embodiments, the compound of formula (I), (Ia), (Ib), (Ic) or (Id) as described herein, or a pharmaceutically acceptable salt thereof, can be administered in a sub-therapeutic dose, while the additional therapeutic agent is administered in an effective amount.

As used herein, the terms "in combination" or "co-administration" can be used interchangeably to refer to the use of more than one therapy (e.g., one or more therapeutic agents). The use of the terms does not restrict the order in which therapies (e.g., therapeutic agents) are administered to a subject.

Examples of therapeutic agents that may be combined with a compound of this disclosure, either administered separately or in the same pharmaceutical composition, include, but are not limited to, muscle relaxants, anticonvulsants, hypnotics, anaesthetics, analgesics, cholinergics, antidepressants, mood stabilisers, anxiolytics, etc.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous, and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., inert diluent, preservative disintegrant (e.g., sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

The active ingredient can be in micro-encapsulated form with one or more excipients. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch.

Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™ alcohols, oils, modified oils, glycols, polysorbates, cyclodextrins, polymers, and mixtures thereof.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol, and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described. An injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In certain embodiments, unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring.

Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The phrase "pharmaceutically acceptable salt," as used herein, refers to pharmaceutically acceptable organic or inorganic salts of a provided compound. For use in medicine, the salts of the provided compounds will be pharmaceutically acceptable salts. Other salts may, however, be useful in the preparation of provided compounds or of their pharmaceutically acceptable salts. Pharmaceutically acceptable salts are well known in the art. For example, Berge et al., describe pharmaceutically acceptable salts in detail in *J. Pharm. Sci.* (1977) 66:1-19, incorporated herein by reference in its entirety. A pharmaceutically acceptable salt involves the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. When multiple charged atoms are present in the parent drug, its pharmaceutically acceptable salts will have multiple counter ions and these can be several instances of the same counter ion or different counter ions. Hence, a pharmaceutically acceptable salt can have one or more charged atoms in the parent compound and/or one or more counter ions.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When a provided compound is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. Quaternary ammonium salts such as $N^+(C_{1-4}$ alkyl$)_4$ are also included.

When a provided compound is basic or contains a sufficiently basic bioisostere, salts may be prepared from pharmaceutically acceptable non-toxic acids, including inorganic and organic acids. Such acids include, but are not limited to, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, carbonic, boric, sulfamic, propionic, butyric, hydroxymaleic, mucic, phenylacetic, sulfanilic, aspartic, edetic, stearic, palmitic, oleic, lauric, ascorbic, valeric, perchloric, malonic, p-toluenesulfonic acid and the like. Particular embodiments include citric, hydrobromic, hydrochloric, maleic, phosphoric, sulfuric and tartaric acids. Other exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, palmoate (i.e., 1,1'-methylene-bis-(2-hydroxy-3-naphthoate)), adipate, alginate, ascorbate, aspartate, cyclopentanepropionate, borate, butyrate, camphorate, digluconate, dodecylsulfate, ethanesulfonate, glucoheptonate, glycerophosphate, hemisulfate, heptanoate, hexanoate, 2-hydroxyethanesulfonate, lactobionate, laurate, lauryl sulphate, malonate, 2-naphthalenesulfonate, nicotinate, pectinate, persulfate, 3-phenylpropionate, picrate, pivalate, propionate, stearate, thiocyanate, undecanoate, and valerate salts.

The preparation of the pharmaceutically acceptable salts described above and other typical pharmaceutically acceptable salts is more fully described by Berge et al., "Pharmaceutical Salts," *J. Pharm. Sci.,* 1977:66:1-19.

Basic nitrogen-containing groups may be quarternized with such agents as lower alkyl halide, such as methyl, ethyl, propyl, and butyl chlorides, bromides and iodides; dialkyl sulfates like dimethyl and diethyl sulfate; and others.

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

It will be appreciated that any compound that is a prodrug of a compound of formula (I), (Ia), (Ib), (Ic) or (Id) is also within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester, such as an acetate or phosphate ester, or where a free amino group is converted into an amide (e.g., α-amino acid amide). Procedures for esterifying, e.g., acylating, the compounds of the invention are well known in the art and may include treatment of the compound with an appropriate carboxylic acid, anhydride or chloride in the presence of a suitable catalyst or base.

The compounds of the invention may be in crystalline form either as the free compounds or as solvates (e.g., hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, e.g., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

The synthetic methods and processes described herein to prepare the compounds of the present invention are amenable to solid phase synthetic techniques and/or combinatorial chemistry to produce individual compounds or libraries of compounds.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Certain embodiments of the invention will now be described with reference to the following examples which are intended for the purpose of illustration only and are not intended to limit the scope of the generality hereinbefore described.

EXAMPLES

Chemical Synthesis

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), methoxy (MeO), ethoxy (EtO), trimethylsilyl (TMS), tert-butyloxycarbonyl (Boc), and acetyl (Ac).

For convenience, many chemical compounds are represented using well known abbreviations, including but not limited to, methanol (MeOH), ethanol (EtOH), ether or diethyl ether (Et$_2$O), ethyl acetate (EtOAc), triethylamine (TEA, Et$_3$N), N,N-diisopropyl-N-ethylamine (DIEA), dichloromethane (methylene chloride, DCM), trifluoroacetic acid (TFA), trifluoroethanol (TFE), dimethylformamide (DMF), sodium sulphate (Na$_2$SO$_4$), tetrahydrofuran (THF), meta-chloroperbenzoic acid (mCPBA), hexamethyldisilazane sodium salt (NaHMDS), O-(7-azabenzotriazol-1-yl)-N,N,N',N'-tetramethyluronium hexafluorophosphate (HATU), dimethylsulfoxide (DMSO), magnesium sulphate (MgSO$_4$), sodium hydrogen carbonate (NaHCO$_3$), tert-butanol (t-BuOH), 1-ethyl-3-(3-dimethylaminopropyl) carbodiimide hydrochloride salt (EDCl·HCl), tetra-n-butylammonium fluoride (TBAF), N,N-diisopropylethylamine (DIPEA), 1-hydroxybenzotriazole (HOBt), hexafluorophosphate benzotriazole tetramethyl uronium (HBTU), trans-dichlorobis(triphenylphosphine)palladium(II) (PdCl$_2$(PPh$_3$)$_2$), tetrakis(triphenylphosphine)palladium(0) (Pd(PPh$_3$)$_4$) tris(dibenzylideneacetone) dipalladium(0) (Pd$_2$ (dba)₃), tri-t-butyl phosphonium tetrafluoroborate (t-Bu₃PH·BF₄), 4,5-bis(diphenylphosphino)-9,9-dimethylxanthene (Xantphos), triphenylphosphine (PPh₃), diisopropyl azodicarboxylate (DIAD), pyridinium chlorochromate (PCC), borane dimethylsulfide (BMS), titanium isopropoxide (TiOiPr₄), sodium triacetoxyborohydride (NaBH(OAc)₃), sodium cyanoborohydride (NaBH₃(CN)), ammonium chloride (NH₄Cl), chloroform (CHCl₃), manganese dioxide (MnO₂), potassium carbonate (K₂CO₃) and 1,2-dichloroethane (DCE), sodium hydride (NaH), dimethylacetamide (DMA), copper(II) oxide (Cu₂O), N-methyl-2-pyrrolidone (NMP), cesium carbonate (Cs₂CO₃), hydrochloric acid (HCl).

General Experimental

Analytical thin-layer chromatography (TLC) was performed on Merck silica gel 60F254 aluminium-backed plates which were visualized using fluorescence quenching under UV light. Flash chromatography was performed using a Biotage Isolera One and standard cartridges. Semi-preparative HPLC purification was performed using a Gilson PLC2020 and a Princeton SPHER-60, C8, 10 μm, 30×150 mm as column.

Intermediate 1-1: 3-methoxy-4-methyl-phenol

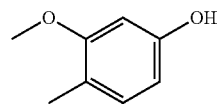

To a solution of 4-hydroxy-2-methoxy-benzaldehyde (1.8 g, 11.8 mmol) in ethanol/acetic acid (50 mL/7.5 mL) was added 10% palladium on activated carbon (500 mg). The mixture was evacuated and back-filled with H₂ (×3) and was left under 4 bars of H₂, stirring at room temperature for 18 h. The reaction mixture was filtered through Celite, rinsing with EtOAc before concentration in vacuo. The crude product thus obtained was purified by silica gel flash chromatography eluting with a gradient of cyclohexane:ethyl acetate—100:0 to 50:50 to give the title compound as a colorless gum (1.4 g, 85% yield). ¹H NMR (300 MHz, DMSO-d₆) 9.14 (s, 1H), 6.86 (d, J=8.0 Hz, 1H), 6.33 (d, J=2.2 Hz, 1H), 6.22 (dd, J=2.2 and 8.0 Hz, 1H), 3.70 (s, 3H), 2.00 (s, 3H).

Synthesis of Example 1

Intermediate 1-2: 4-iodo-2-(3-methoxy-4-methyl-phenoxy)pyridine

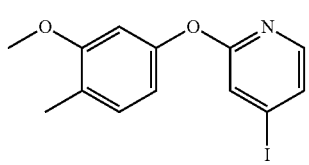 [SMILES: COc1cc(Oc2cc(I)ccn2)ccc1C]

NaH (91 mg, 2.39 mmol) was added dropwise to a stirred solution of 3-methoxy-4-methyl-phenol (300 mg, 2.17 mmol) in DMF (5 mL) at 0° C. under nitrogen. The resulting solution was stirred 0° C. for 30 min before 2-fluoro-4-iodopyridine (726 mg, 3.26 mmol) was added. The ice bath was removed, and the mixture was left to stir at room temperature for 4 h. The mixture was hydrolyzed with water, extracted with Et₂O, the organics were washed with brine, dried over MgSO₄ and concentrated in vacuo before purification by silica gel flash chromatography eluting with a gradient of cyclohexane:ethyl acetate—100:0 to 50:50 to give the title compound as a yellow oil (730 mg, 99% yield). ESIMS m/z [M+H]⁺ 342.0

Example 1: 3-[2-(3-methoxy-4-methyl-phenoxy)-4-pyridyl]-5,5-dimethyl-imidazolidine-2,4-dione

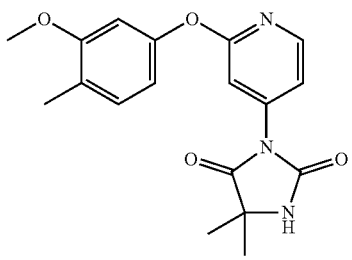 [SMILES: COc1cc(Oc2cc(N3C(=O)NC(C)(C)C3=O)ccn2)ccc1C]

To a reaction vessel charged with 4-iodo-2-(3-methoxy-4-methyl-phenoxy)pyridine (200 mg, 0.59 mmol), 5,5-dimethyl hydantoin (225 mg, 1.76 mmol) in DMA (4 mL) was added Cu₂O (84 mg, 0.59 mmol). The vessel was sealed and the mixture allowed to stir for 18 h at 150° C. The reaction mixture was directly adsorbed onto silica and concentrated in vacuo before purification by silica gel flash chromatography eluting with a gradient of cyclohexane:ethyl acetate—100:0 to 0:100. The product obtained was submitted to semi-preparative HPLC, gradient elution with 5%-100% acetonitrile/water mixtures and 0.1% formic acid to give after lyophilization using acetonitrile/water the title compound as a white foam (24 mg, 14% yield). ¹H NMR (300 MHz, DMSO-d₆) 8.74 (bs, 1H), 8.21 (d, J=5.5 Hz, 1H), 7.30 (dd, J=1.5 and 5.5 Hz, 1H), 7.13 (m, 2H), 6.73 (d, J=2.2 Hz, 1H), 6.59 (dd, J=2.2 and 8.0 Hz, 1H), 3.73 (s, 3H), 2.12 (s, 3H), 1.38 (s, 6H). ESIMS m/z [M+H]⁺ 342.25

Synthesis of Example 2

Intermediate 1-3: 2-(benzofuran-6-yloxy)-4-iodo-pyridine

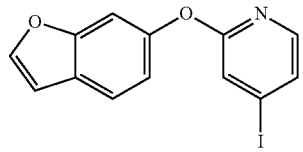 [SMILES: Ic1ccnc(Oc2ccc3ccoc3c2)c1]

Essentially following the procedures described for intermediate 1-2, using benzofuran-6-ol (132 mg, 0.99 mmol) to afford, after purification by silica gel flash chromatography eluting with a gradient of cyclohexane:ethyl acetate—100:0 to 50:50 the title compound as a white foam (110 mg, 36% yield). ESIMS m/z [M+H]⁺ 337.92.

Example 2: 3-[2-(benzofuran-6-yloxy)-4-pyridyl]-5,5-dimethyl-imidazolidine-2,4-dione

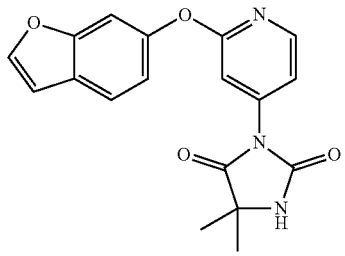 [SMILES: CC1(C)NC(=O)N(c2ccnc(Oc3ccc4ccoc4c3)c2)C1=O]

To a reaction vessel charged with intermediate 1-3 (100 mg, 0.30 mmol), 5,5-dimethyl hydantoin (38 mg, 0.30 mmol) and potassium carbonate (82 mg, 0.60 mmol) in DMF (5 mL) was added copper (I) iodide (56 mg, 0.30 mmol). The mixture was degazed using argon for 30 minutes and then trans-N,N'-dimethylcyclohexane-1,2-diamine (17 mg, 0.12 mmol) was added. The vessel was sealed and the mixture allowed to stir for 18 h at 90° C. The mixture was hydrolyzed with water, extracted with $Et_2O$, the organics were washed with brine, dried over $MgSO_4$ and concentrated in vacuo before purification by silica gel flash chromatography eluting with a gradient of cyclohexane:ethyl acetate—100:0 to 20:80 the title compound as a white solid (45 mg, 45% yield). $^1$H NMR (300 MHz, DMSO-$d_6$) 8.75 (bs, 1H), 8.19 (d, J=5.5 Hz, 1H), 8.00 (d, J=2.2 Hz, 1H), 7.66 (d, J=8.4 Hz, 1H), 7.45 (d, J=1.5 Hz, 1H), 7.32 (dd, J=1.5 and 5.5 Hz, 1H), 7.20 (d, J=1.5 Hz, 1H), 7.05 (dd, J=2.1 and 8.4 Hz, 1H), 6.97 (d, J=2.2 Hz, 1H), 1.38 (s, 6H). ESIMS m/z [M+H]$^+$ 338.17.

Synthesis of Example 3

Intermediate 1-4: 2-indan-5-yloxy-4-iodo-pyridine

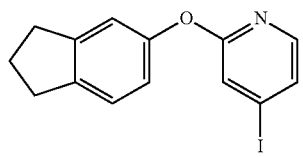

Essentially following the procedures described for intermediate 1-2, using 5-hydroxyindan (200 mg, 1.48 mmol) to afford, after purification by silica gel flash chromatography eluting with a gradient of cyclohexane:ethyl acetate—100:0 to 50:50 the title compound as a white foam (300 mg, 66% yield). $^1$H NMR (300 MHz, CHCl$_3$-d) 7.85 (d, J=5.2 Hz, 1H), 7.35-7.28 (m, 2H), 7.22 (d, J=8.1 Hz, 1H), 6.96 (s, 1H), 6.86 (dd, J=2.1 and 8.1 Hz, 1H), 3.01-2.82 (m, 4H), 2.20-2.04 (m, 2H).

Example 3: 3-(2-indan-5-yloxy-4-pyridyl)-5,5-dimethyl-imidazolidine-2,4-dione

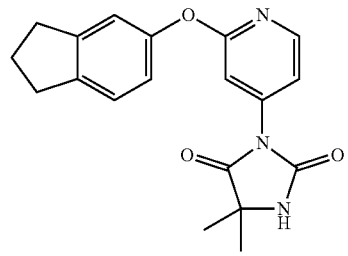 [SMILES: CC1(C)NC(=O)N(c2ccnc(Oc3ccc4c(c3)CCC4)c2)C1=O]

Essentially following the procedures described for example 2, using intermediate 1-4 (300 mg, 0.89 mmol) to afford, after purification by silica gel flash chromatography eluting with a gradient of cyclohexane:ethyl acetate—100:0 to 20:80 the title compound as a white solid (120 mg, 40% yield). $^1$H NMR (300 MHz, DMSO-$d_6$) 8.75 (bs, 1H), 8.18 (d, J=5.5 Hz, 1H), 7.28 (dd, J=1.6 and 5.5 Hz, 1H), 7.22 (d, J=8.1 Hz, 1H), 7.14 (d, J=1.5 Hz, 1H), 6.97 (m, 1H), 6.85 (dd, J=2.1 and 8.1 Hz, 1H), 2.90-2.85 (m, 4H), 2.10-1.92 (m, 2H), 1.38 (s, 6H). ESIMS m/z [M+H]$^+$ 338.25.

Synthesis of Example 4

Intermediate 1-5: 4-iodo-2-[3-methoxy-4-(trifluoromethyl)phenoxy]pyridine

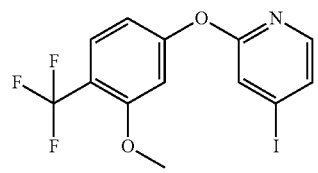 [SMILES: COc1cc(Oc2cc(I)ccn2)ccc1C(F)(F)F]

Essentially following the procedures described for intermediate 1-2, using 3-methoxy-4-(trifluoromethyl)phenol (380 mg, 1.97 mmol) to afford, after purification by silica gel flash chromatography eluting with a gradient of cyclohexane:ethyl acetate—100:0 to 50:50 the title compound as a white foam (100 mg, 14% yield). ESIMS m/z [M+H]$^+$ 396.25.

Example 4: 3-[2-[3-methoxy-4-(trifluoromethyl)phenoxy]-4-pyridyl]-5,5-dimethyl-imidazolidine-2,4-dione

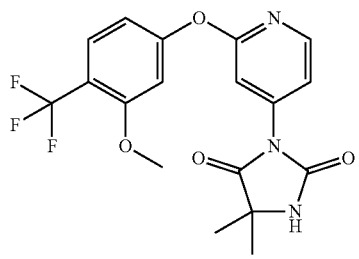 [SMILES: COc1cc(Oc2cc(N3C(=O)NC(C)(C)C3=O)ccn2)ccc1C(F)(F)F]

Essentially following the procedures described for example 2, using intermediate 1-5 (100 mg, 0.89 mmol) to afford, after purification by silica gel flash chromatography eluting with a gradient of cyclohexane:ethyl acetate—100:0 to 20:80, semi-preparative HPLC and lyophilization using water and methanol, the title compound as a white solid (6 mg, 6% yield). $^1$H NMR (300 MHz, DMSO-d$_6$) 8.78 (bs, 1H), 8.26 (d, J=5.5 Hz, 1H), 7.63 (d, J=8.6 Hz, 1H), 7.40 (dd, J=1.6 and 5.5 Hz, 1H), 7.30 (d, J=1.6 Hz, 1H), 7.10-7.06 (m, 1H), 6.84-6.78 (m, 1H), 3.85 (s, 3H), 1.39 (s, 6H). ESIMS m/z [M+H]$^+$ 396.25.

Synthesis of Example 5

Intermediate 1-6: 2-(3-fluoro-4-methyl-phenoxy)-4-iodo-pyridine

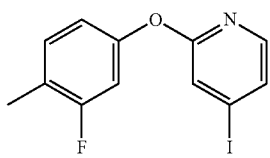 [SMILES: Cc1ccc(Oc2cc(I)ccn2)cc1F]

Cesium carbonate (1.17 g, 3.59 mmol) was added dropwise to a stirred solution of 3-fluoro-4-methylphenol (250 mg, 1.97 mmol) in DMF (10 mL) at 0° C. under nitrogen. The resulting solution was stirred 0° C. for 30 min before 2-fluoro-4-iodopyridine (400 mg, 1.80 mmol) was added. The ice bath was removed, and the mixture was left to stir at room temperature for 18 h. The mixture was hydrolyzed with water, extracted with Et$_2$O, the organics were washed with brine, dried over MgSO$_4$ and concentrated in vacuo to afford, after purification by silica gel flash chromatography eluting with a gradient of cyclohexane:ethyl acetate—100:0 to 70:30 the title compound as a white foam (420 mg, 72% yield). ESIMS m/z [M+H]$^+$ 330.18.

Example 5: 3-[2-(3-fluoro-4-methyl-phenoxy)-4-pyridyl]-5,5-dimethyl-imidazolidine-2,4-dione

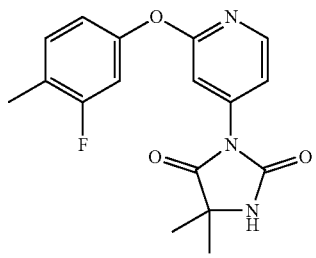 [SMILES: Cc1ccc(Oc2cc(N3C(=O)NC(C)(C)C3=O)ccn2)cc1F]

Essentially following the procedures described for example 2, using intermediate 1-6 (420 mg, 1.28 mmol) to afford, after purification by silica gel flash chromatography eluting with a gradient of cyclohexane:ethyl acetate—100:0 to 20:80, semi-preparative HPLC and lyophilization using water and methanol, the title compound as a white solid (70 mg, 16% yield). $^1$H NMR (300 MHz, DMSO-d$_6$) 8.77 (bs, 1H), 8.20 (d, J=5.6 Hz, 1H), 7.37-7.25 (m, 2H), 7.20 (d, J=1.4 Hz, 1H), 7.02 (dd, J=2.3 and 10.7 Hz, 1H), 6.69 (dd, J=2.3 and 8.4 Hz, 1H), 2.22 (d, J=1.6 Hz, 3H), 1.38 (s, 6H). ESIMS m/z [M+H]$^+$ 330.25.

Synthesis of Example 6

Intermediate 1-7: 4-iodo-2-[3-methoxy-4-fluorophenyl]pyridine

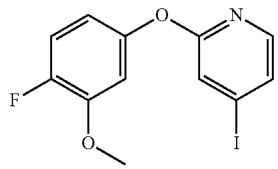 [SMILES: COc1cc(Oc2cc(I)ccn2)ccc1F]

Essentially following the procedures described for intermediate 1-6, using 3-methoxy-4-fluorophenol (380 mg, 2.67 mmol) to afford, after purification by silica gel flash chromatography eluting with a gradient of cyclohexane:dichloromethane—100:0 to 20:80 the title compound as a colorless oil (160 mg, 17% yield). $^1$H NMR (300 MHz, CHCl$_3$-d) 7.85 (d, J=5.3 Hz, 1H), 7.40-7.28 (m, 2H), 7.09 (dd, J=8.8 and 10.9 Hz, 1H), 6.75 (dd, J=2.7 and 7.2 Hz, 1H), 6.70-6.58 (m, 1H), 3.86 (s, 3H).

Example 6: 3-[2-[3-methoxy-4-fluorophenoxy]-4-pyridyl]-5,5-dimethyl-imidazolidine-2,4-dione

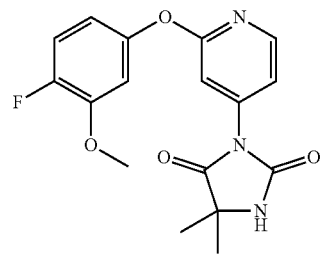 [SMILES: COc1cc(Oc2cc(N3C(=O)NC(C)(C)C3=O)ccn2)ccc1F]

Essentially following the procedures described for example 2, using intermediate 1-7 (160 mg, 0.46 mmol) to afford, after purification by silica gel flash chromatography eluting with a gradient of cyclohexane:ethyl acetate—100:0 to 20:80 and lyophilization using water and methanol, the title compound as a white solid (110 mg, 67% yield). $^1$H NMR (300 MHz, DMSO-d$_6$) 8.76 (bs, 1H), 8.20 (d, J=5.5 Hz, 1H), 7.31 (dd, J=1.7 and 5.5 Hz, 1H), 7.28-7.15 (m, 2H) 7.01 (dd, J=2.8 and 7.5 Hz, 1H), 6.72-6.65 (m, 1H), 3.79 (s, 3H), 1.38 (s, 6H). ESIMS m/z [M+H]$^+$ 346.25.

Synthesis of Example 7

Intermediate 1-8: 2-(1,3-benzodioxol-5-yloxy)-4-iodo-pyridine

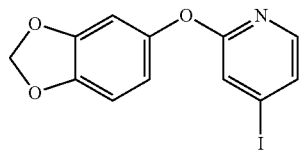 [SMILES: Ic1ccnc(Oc2ccc3c(c2)OCO3)c1]

Essentially following the procedures described for intermediate 1-2, using sesamol (204 mg, 1.48 mmol) to afford, after purification by silica gel flash chromatography eluting with a gradient of cyclohexane:ethyl acetate—100:0 to 60:40 the title compound as a colorless oil (170 mg, 38% yield). $^1$H NMR (300 MHz, CHCl$_3$-d) 7.85 (d, J=5.3 Hz, 1H), 7.36-7.26 (m, 2H), 6.80 (d, J=8.3 Hz, 1H), 6.65-6.53 (m, 2H), 6.00 (s, 2H).

Example 7: 3-[2-(1,3-benzodioxol-5-yloxy)-4-pyridyl]-5,5-dimethyl-imidazolidine-2,4-dione

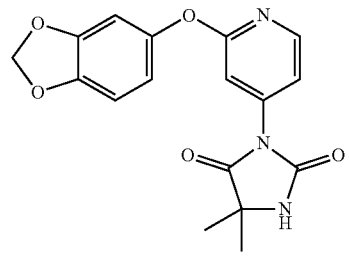

Essentially following the procedures described for example 2, using intermediate 1-8 (170 mg, 0.50 mmol) to afford, after purification by silica gel flash chromatography eluting with a gradient of cyclohexane:ethyl acetate—100:0 to 0:100, the title compound as a white solid (115 mg, 66% yield). $^1$H NMR (300 MHz, DMSO-d$_6$) 8.74 (bs, 1H), 8.19 (d, J=5.6 Hz, 1H), 7.29 (dd, J=1.7 and 5.6 Hz, 1H), 7.13 (d, J=1.6 Hz, 1H), 6.91 (d, J=8.4 Hz, 1H), 6.80 (d, J=2.4 Hz, 1H), 6.58 (dd, J=2.4 and 8.4 Hz, 1H), 6.04 (s, 2H), 1.38 (s, 6H). ESIMS m/z [M+H]$^+$ 342.25.

Synthesis of Example 8

Intermediate 1-9: 2-(4-chloro-3-methoxy-phenoxy)-4-iodo-pyridine

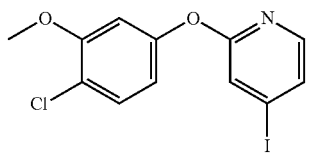 [SMILES: COc1cc(Oc2cc(I)ccn2)ccc1Cl]

Essentially following the procedures described for intermediate 1-2, using 4-chloro-3-methoxyphenol (234 mg, 1.48 mmol) to afford, after purification by silica gel flash chromatography eluting with a gradient of cyclohexane:ethyl acetate—100:0 to 50:50 the title compound as a white foam (100 mg, 21% yield). $^1$H NMR (300 MHz, CHCl$_3$-d) 7.85 (d, J=5.3 Hz, 1H), 7.40-7.30 (m, 3H), 6.73 (d, J=2.5 Hz, 1H), 6.66 (dd, J=2.6 and 8.5 Hz, 1H), 3.87 (s, 3H).

Example 8: 3-[2-(4-chloro-3-methoxy-phenoxy)-4-pyridyl]-5,5-dimethyl-imidazolidine-2,4-dione

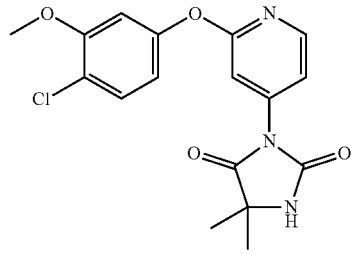 [SMILES: COc1cc(Oc2cc(N3C(=O)NC(C)(C)C3=O)ccn2)ccc1Cl]

Essentially following the procedures described for example 2, using intermediate 1-9 (90 mg, 0.25 mmol) to afford, after purification by silica gel flash chromatography eluting with a gradient of cyclohexane:ethyl acetate—100:0 to 0:100 and lyophilization using water and acetonitrile, the title compound as a white solid (64 mg, 69% yield). $^1$H NMR (300 MHz, DMSO-d$_6$) 8.77 (bs, 1H), 8.22 (d, J=5.5 Hz, 1H), 7.43 (d, J=8.6 Hz, 1H), 7.34 (dd, J=1.5 and 5.5 Hz, 1H), 7.21 (d, J=1.5 Hz, 1H), 6.99 (d, J=2.5 Hz, 1H), 6.73 (dd, J=2.5 and 8.6 Hz, 1H), 3.81 (s, 3H), 1.38 (s, 6H). ESIMS m/z [M+H]$^+$ 362.25.

Synthesis of Example 9

Intermediate 1-10: (2,2-difluoro-1,3-benzodioxol-5-yl)boronic Acid

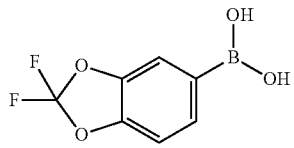 [SMILES: OB(O)c1ccc2c(c1)OC(F)(F)O2]

n-Butyl lithium 2.5M in hexane (11.36 mL, 28.40 mmol) was added dropwise to a stirred solution of 5-bromo-2,2-difluoro-1,3-benzodioxole (5.0 g, 21.10 mmol) and triisopropyl borate (6.3 g, 33.50 mmol) in THF (60 mL) at −78° C. under nitrogen. The resulting solution was stirred at −78° C. for 1 h and at room temperature for 3 h. The mixture was hydrolyzed with a saturated aqueous solution of ammonium chloride (20 mL), stirred 30 minutes, an aqueous solution of 3N HCl (20 mL) was then added and the mixture was extracted with Et$_2$O. The organics were washed with brine, dried over MgSO$_4$ and concentrated in vacuo to afford the title compound as a yellow oil which was used directly for next step.

Intermediate 1-11: 2,2-difluoro-1,3-benzodioxol-5-ol

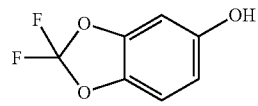

Hydrogen peroxide 30% in water (40 mL) was added dropwise to a stirred solution of crude intermediate 1-10 in THF (100 mL) at room temperature. The resulting solution was stirred 20 h and carefully hydrolyzed with a saturated aqueous solution of Na$_2$S2O3 (50 mL). The mixture was extracted with ethylacetate (3×50 mL), the organics were washed with brine, dried over MgSO$_4$ and concentrated in vacuo to afford, after purification by silica gel flash chromatography eluting with a gradient of cyclohexane:ethyl acetate—100:0 to 50:50 the title compound as a yellow oil (3.2 g, 80% yield). $^1$H NMR (300 MHz, CHCl$_3$-d) 9.77 (s, 1H), 7.14 (d, J=8.8 Hz, 1H), 6.76 (d, J=2.4 Hz, 1H), 6.51 (dd, J=2.4 and 8.8 Hz, 1H).

Intermediate 1-12: 2-[(2,2-difluoro-1,3-benzodioxol-5-yl)oxy]-4-iodo-pyridine

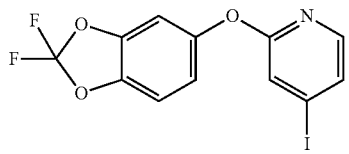 [SMILES: FC1(F)Oc2ccc(Oc3cc(I)ccn3)cc2O1]

Essentially following the procedures described for intermediate 1-2, using intermediate 1-11 (160 mg, 0.92 mmol) to afford, after purification by silica gel flash chromatography eluting with a gradient of cyclohexane:ethyl acetate—100:0 to 50:50 the title compound as a colorless oil (67 mg, 19% yield). ESIMS m/z [M+H]$^+$ 378.1.

Example 9: 3-[2-[(2,2-difluoro-1,3-benzodioxol-5-yl)oxy]-4-pyridyl]-5,5-dimethyl-imidazolidine-2,4-dione

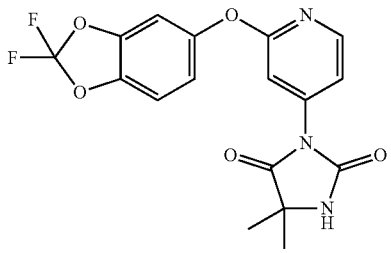 [SMILES: CC1(C)NC(=O)N(c2ccnc(Oc3ccc4c(c3)OC(F)(F)O4)c2)C1=O]

Essentially following the procedures described for example 2, using intermediate 1-12 (64 mg, 0.17 mmol) to afford, after purification by silica gel flash chromatography eluting with a gradient of cyclohexane:ethyl acetate—100:0 to 0:100 and semi-preparative HPLC, the title compound as a white solid (34 mg, 53% yield). $^1$H NMR (300 MHz, DMSO-d$_6$) 8.77 (bs, 1H), 8.19 (d, J=5.6 Hz, 1H), 7.46-7.38 (m, 2H), 7.34 (dd, J=1.7 and 5.6 Hz, 1H), 7.23 (d, J=1.5 Hz, 1H), 6.99 (dd, J=2.4 and 8.8 Hz, 1H), 1.39 (s, 6H). ESIMS m/z [M+H]$^+$ 378.33.

Intermediate 2-1:
(5R)-5-ethyl-5-methyl-imidazolidine-2,4-dione

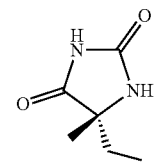

To a suspension of (2R)-2-amino-2-methyl-butanoic acid (500 mg, 4.27 mmol) in water (20 mL) was added potassium cyanate (450 mg, 5.55 mmol). The mixture was stirred at 90° C. for 2 h and cooled to room temperature. Hydrochloric acid 37% in water (20 mL) was added and the mixture was stirred at 90° C. for 1 h. The solvents were evaporated under reduced pressure, the white solid was taken in DCM/MeOH (20/4 mL) and filtered to give the title compound as a white solid (460 mg, 76% yield). $^1$H NMR (300 MHz, DMSO-d$_6$) 10.54 (bs, 1H), 7.85 (bs, 1H), 1.68-1.43 (m, 2H), 1.20 (s, 3H), 0.74 (t, J=7.4 Hz, 3H).

Synthesis of Example 10

Example 10: (5R)-5-ethyl-3-[2-(3-methoxy-4-methyl-phenoxy)-4-pyridyl]-5-methyl-imidazolidine-2,4-dione

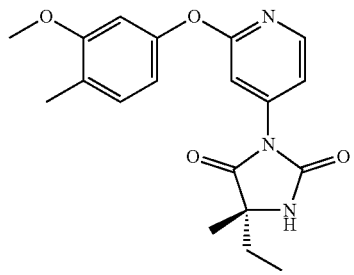

Essentially following the procedures described for example 1-1, using intermediate 1-2 (170 mg, 0.50 mmol) and intermediate 2-1 (212 mg, 1.50 mmol) to afford, after purification by silica gel flash chromatography eluting with a gradient of cyclohexane:ethyl acetate—100:0 to 0:100, semi-preparative HPLC and lyophilization using water and methanol, the title compound as a white solid (66 mg, 37% yield). $^1$H NMR (300 MHz, DMSO-d$_6$) 8.72 (bs, 1H), 8.20 (d, J=5.5 Hz, 1H), 7.28 (dd, J=1.7 and 5.5 Hz, 1H), 7.18-7.10 (m, 2H), 6.74 (d, J=2.2 Hz, 1H), 6.59 (dd, J=2.2 and 8.0 Hz, 1H), 3.73 (s, 3H), 2.12 (s, 3H), 1.83-1.68 (m, 2H), 1.36 (s, 3H), 0.82 (t, J=7.4 Hz, 3H). ESIMS m/z [M+H]$^+$ 356.42.

Synthesis of Example 11

Example 11: (5R)-5-ethyl-3-[2-(3-methoxy-4-fluoro-phenoxy)-4-pyridyl]-5-methyl-imidazolidine-2,4-dione

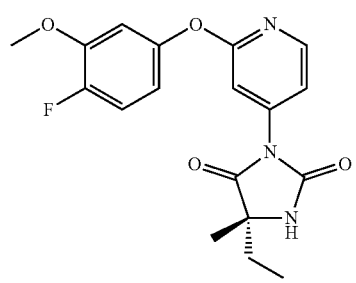 [SMILES: CC[C@@]1(C)NC(=O)N(c2ccnc(Oc3ccc(C)c(OC)c3)c2)C1=O]

Essentially following the procedures described for example 2, using intermediate 1-7 (170 mg, 0.50 mmol) and intermediate 2-1 (91 mg, 0.64 mmol) to afford, after purification by silica gel flash chromatography eluting with a gradient of cyclohexane:ethyl acetate—100:0 to 0:100 and lyophilization using water and acetonitrile, the title compound as a white solid (90 mg, 50% yield). $^1$H NMR (300 MHz, DMSO-$d_6$) 8.74 (bs, 1H), 8.20 (d, J=5.5 Hz, 1H), 7.32-7.10 (m, 3H), 7.01 (dd, J=2.7 and 7.5 Hz, 1H), 6.73-6.60 (m, 1H), 3.79 (s, 3H), 1.83-1.68 (m, 2H), 1.37 (s, 3H), 0.82 (t, J=7.4 Hz, 3H). ESIMS m/z [M+H]$^+$ 360.42.

Synthesis of Example 12

Example 12: (5R)-5-ethyl-3-[2-(3-fluoro-4-methyl-phenoxy)-4-pyridyl]-5-methyl-imidazolidine-2,4-dione

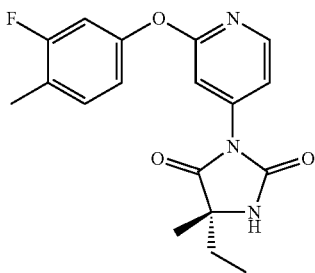 [SMILES: CC[C@@]1(C)NC(=O)N(c2ccnc(Oc3ccc(C)c(F)c3)c2)C1=O]

Essentially following the procedures described for example 2, using intermediate 1-5 (280 mg, 0.85 mmol) and intermediate 2-1 (157 mg, 1.11 mmol) to afford, after purification by silica gel flash chromatography eluting with a gradient of cyclohexane:ethyl acetate—100:0 to 0:100, Sephadex column (eluant DCM/MeOH, 75/25) and lyophilization using water and acetonitrile, the title compound as a white solid (95 mg, 32% yield). $^1$H NMR (300 MHz, DMSO-$d_6$) 8.74 (bs, 1H), 8.20 (d, J=5.5 Hz, 1H), 7.35-7.28 (m, 2H), 7.19 (d, J=1.5 Hz, 1H), 7.03 (dd, J=2.2 and 10.7 Hz, 1H), 6.89 (dd, J=2.2 and 8.3 Hz, 1H), 2.21 (s, 3H), 1.83-1.58 (m, 2H), 1.37 (s, 3H), 0.82 (t, J=7.4 Hz, 3H). ESIMS m/z [M+H]$^+$ 344.25.

Synthesis of Example 13

Example 13: (5R)-5-ethyl-3-(2-indan-5-yloxy-4-pyridyl)-5-methyl-imidazolidine-2,4-dione

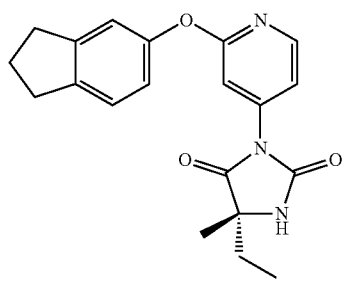 [SMILES: CC[C@@]1(C)NC(=O)N(c2ccnc(Oc3ccc4c(c3)CCC4)c2)C1=O]

Essentially following the procedures described for example 2, using intermediate 1-4 (220 mg, 0.65 mmol) and intermediate 2-1 (102 mg, 0.72 mmol) to afford, after purification by silica gel flash chromatography eluting with a gradient of cyclohexane:ethyl acetate—100:0 to 0:100, the title compound as a white solid (150 mg, 65% yield). $^1$H NMR (300 MHz, DMSO-$d_6$) 8.73 (bs, 1H), 8.18 (d, J=5.5 Hz, 1H), 7.30-7.19 (m, 2H), 7.13 (d, J=1.5 Hz, 1H), 6.97 (s, 1H), 6.85 (dd, J=2.2 and 8.0 Hz, 1H), 2.90-2.78 (m, 4H), 2.10-1.95 (m, 2H), 1.83-1.55 (m, 2H), 1.37 (s, 3H), 0.82 (t, J=7.4 Hz, 3H). ESIMS m/z [M+H]$^+$ 352.33.

Synthesis of Example 14

Example 14: (5R)-3-[2-(benzofuran-6-yloxy)-4-pyridyl]-5-ethyl-5-methyl-imidazolidine-2,4-dione

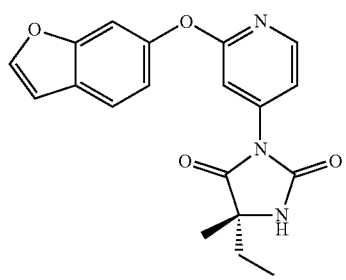 [SMILES: CC[C@@]1(C)NC(=O)N(c2ccnc(Oc3ccc4ccoc4c3)c2)C1=O]

Essentially following the procedures described for example 2, using intermediate 1-3 (200 mg, 0.60 mmol) and intermediate 2-1 (101 mg, 0.71 mmol) to afford, after purification by silica gel flash chromatography eluting with a gradient of cyclohexane:ethyl acetate—100:0 to 0:100 and lyophilization using water and acetonitrile, the title compound as a white solid (100 mg, 47% yield). $^1$H NMR (300 MHz, DMSO-$d_6$) 8.74 (bs, 1H), 8.19 (d, J=5.5 Hz, 1H), 8.00 (d, J=2.2 Hz, 1H), 7.66 (d, J=8.5 Hz, 1H), 7.46 (s, 1H), 7.30 (dd, J=1.5 and 5.5 Hz, 1H), 7.19 (d, J=1.5 Hz, 1H), 7.05 (dd, J=2.0 and 8.4 Hz, 1H), 6.97 (d, J=1.5 Hz, 1H), 1.83-1.68 (m, 2H), 1.37 (s, 3H), 0.82 (t, J=7.4 Hz, 3H). ESIMS m/z [M+H]$^+$ 352.25.

Synthesis of Example 15

Example 15: (5R)-5-ethyl-3-[2-(3-methoxy-4-chloro-phenoxy)-4-pyridyl]-5-methyl-imidazolidine-2,4-dione

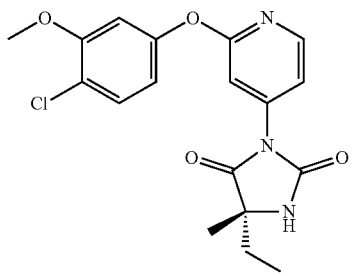 [SMILES: CC[C@@]1(C)NC(=O)N(c2ccnc(Oc3ccc(Cl)c(OC)c3)c2)C1=O]

Essentially following the procedures described for example 2, using intermediate 1-9 (143 mg, 0.40 mmol) and intermediate 2-1 (68 mg, 0.47 mmol) to afford, after two purifications by silica gel flash chromatography eluting with a gradient of cyclohexane:ethyl acetate—100:0 to 0:100 and lyophilization using water and methanol, the title compound as a white solid (80 mg, 53% yield). $^1$H NMR (300 MHz, DMSO-$d_6$) 8.75 (bs, 1H), 8.22 (d, J=5.5 Hz, 1H), 7.43 (d, J=8.6 Hz, 1H), 7.32 (dd, J=1.6 and 5.5 Hz, 1H), 7.20 (d, J=1.3 Hz, 1H), 7.00 (d, J=2.5 Hz, 1H), 6.73 (dd, J=2.5 and 8.6 Hz, 1H), 3.80 (s, 3H), 1.83-1.68 (m, 2H), 1.37 (s, 3H), 0.82 (t, J=7.4 Hz, 3H). ESIMS m/z [M+H]$^+$ 376.0.

Synthesis of Example 16

Example 16: (5R)-3-[2-[(2,2-difluoro-1,3-benzodioxol-5-yl)oxy]-4-pyridyl]-5-ethyl-5-methyl-imidazolidine-2,4-dione

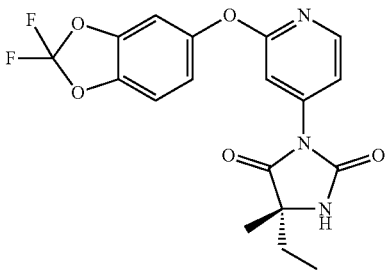 [SMILES: CC[C@@]1(C)NC(=O)N(c2ccnc(Oc3ccc4c(c3)OC(F)(F)O4)c2)C1=O]

Essentially following the procedures described for example 2, using intermediate 1-12 (280 mg, 0.74 mmol) and intermediate 2-1 (130 mg, 0.91 mmol) to afford, after purification by silica gel flash chromatography eluting with a gradient of cyclohexane:dichloromethane—100:0 to 0:100 and a gradient of dichloromethane:ethylacetate—100:0 to 50:50 and lyophilization using water and acetonitrile, the title compound as a white solid (64 mg, 22% yield). $^1$H NMR (300 MHz, DMSO-$d_6$) 8.77 (bs, 1H), 8.21 (d, J=5.5 Hz, 1H), 7.50-7.40 (m, 2H), 7.34 (dd, J=1.7 and 5.6 Hz, 1H), 7.24 (d, J=1.5 Hz, 1H), 7.02 (dd, J=2.4 and 8.7 Hz, 1H), 1.90-1.60 (m, 2H), 1.40 (s, 3H), 0.84 (t, J=7.4 Hz, 3H). ESIMS m/z [M+H]$^+$ 391.9.

Synthesis of Example 17

Intermediate 2-2: 2-(3,4-dimethylphenoxy)-4-iodo-pyridine

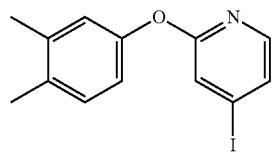 [SMILES: Cc1ccc(Oc2cc(I)ccn2)cc1C]

Essentially following the procedures described for intermediate 1-2, using 3,4-dimethylphenol (135 mg, 1.10 mmol) to afford, after purification by silica gel flash chromatography eluting with a gradient of cyclohexane:ethyl acetate—100:0 to 80:20 the title compound as a white powder (300 mg, 84% yield). $^1$H NMR (300 MHz, CHCl$_3$-d) 7.83 (d, J=5.3 Hz, 1H), 7.47 (dd, J=1.2 and 5.3 Hz, 1H), 7.38 (s, 1H), 7.13 (d, J=8.1 Hz, 1H), 6.89 (d, J=2.3 Hz, 1H), 6.81 (dd, J=2.4 and 8.1 Hz, 1H), 2.19 (s, 6H).

Example 17: (5R)-3-[2-(3,4-dimethylphenoxy)-4-pyridyl]-5-ethyl-5-methyl-imidazolidine-2,4-dione

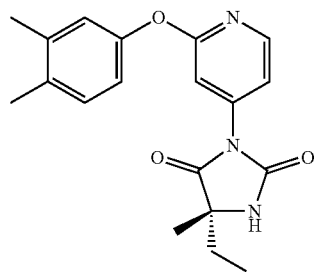 [SMILES: CC[C@@]1(C)NC(=O)N(c2ccnc(Oc3ccc(C)c(C)c3)c2)C1=O]

Essentially following the procedures described for example 2, using intermediate 2-2 (200 mg, 0.62 mmol) and intermediate 2-1 (105 mg, 0.74 mmol) to afford, after purification by silica gel flash chromatography eluting with a gradient of cyclohexane:ethyl acetate—100:0 to 0:100 and lyophilization using water and acetonitrile, the title compound as a white solid (130 mg, 61% yield). $^1$H NMR (300 MHz, DMSO-$d_6$) 8.72 (bs, 1H), 8.17 (d, J=5.5 Hz, 1H), 7.26 (dd, J=1.7 and 5.5 Hz, 1H), 7.17-7.10 (m, 2H), 6.91 (d, J=2.5 Hz, 1H), 6.83 (dd, J=2.5 and 8.1 Hz, 1H), 2.19 (s, 6H), 1.85-1.58 (m, 2H), 1.36 (s, 3H), 0.83 (t, J=7.4 Hz, 3H). ESIMS m/z [M+H]$^+$ 340.33.

Synthesis of Example 18

Intermediate 2-3: 2-indan-4-yloxy-4-iodo-pyridine

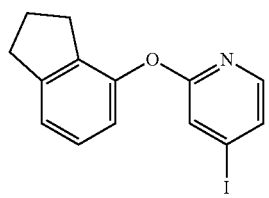 [SMILES: Ic1ccnc(Oc2cccc3c2CCC3)c1]

Essentially following the procedures described for intermediate 1-2, using indan-4-ol (160 mg, 1.20 mmol) to afford, after purification by silica gel flash chromatography eluting with a gradient of cyclohexane:dichloromethane—100:0 to 0:100 the title compound as a white powder (315 mg, 76% yield). ESIMS m/z [M+H]$^+$ 338.08.

Example 18: (5R)-5-ethyl-3-(2-indan-4-yloxy-4-pyridyl)-5-methyl-imidazolidine-2,4-dione

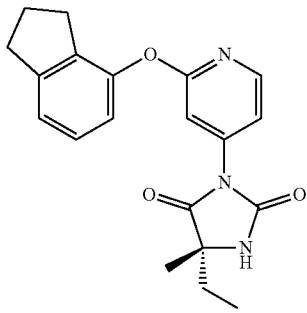 [SMILES: CC[C@@]1(C)NC(=O)N(c2ccnc(Oc3cccc4c3CCC4)c2)C1=O]

Essentially following the procedures described for example 2, using intermediate 2-3 (200 mg, 0.60 mmol) and intermediate 2-1 (142 mg, 0.71 mmol) to afford, after purification by silica gel flash chromatography eluting with a gradient of cyclohexane:ethyl acetate—100:0 to 0:100 and lyophilization using water and acetonitrile, the title compound as a white solid (113 mg, 54% yield). $^1$H NMR (300 MHz, DMSO-d$_6$) 8.73 (bs, 1H), 8.16 (d, J=5.5 Hz, 1H), 7.26 (dd, J=1.7 and 5.5 Hz, 1H), 7.20-7.05 (m, 3H), 6.87 (d, J=8.0 Hz, 1H), 2.89 (app. t, J=7.4 Hz, 2H), 2.62 (app. t, J=7.4 Hz, 2H), 1.96 (app. quint, J=7.4 Hz, 2H), 1.85-1.58 (m, 2H), 1.37 (s, 3H), 0.83 (t, J=7.4 Hz, 3H). ESIMS m/z [M+H]$^+$ 352.25.

Synthesis of Example 19

Intermediate 2-4:
2-chroman-7-yloxy-4-iodo-pyridine

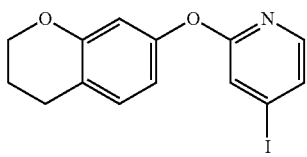 [SMILES: Ic1ccnc(Oc2ccc3c(c2)OCCC3)c1]

Essentially following the procedures described for intermediate 1-2, using chroman-7-ol (200 mg, 1.33 mmol) to afford, after purification by silica gel flash chromatography eluting with a gradient of cyclohexane:ethyl acetate—100:0 to 0:100 the title compound as a colorless oil (148 mg, 32% yield). ESIMS m/z [M+H]$^+$ 354.08.

Example 19: (5R)-3-(2-chroman-7-yloxy-4-pyridyl)-5-ethyl-5-methyl-imidazolidine-2,4-dione

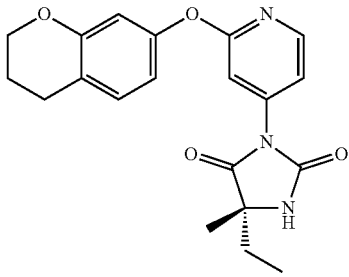 [SMILES: CC[C@@]1(C)NC(=O)N(c2ccnc(Oc3ccc4c(c3)OCCC4)c2)C1=O]

Essentially following the procedures described for example 2, using intermediate 2-4 (134 mg, 0.38 mmol) and intermediate 2-1 (54 mg, 0.38 mmol) to afford, after purification by silica gel flash chromatography eluting with a gradient of cyclohexane:ethyl acetate—100:0 to 0:100, the title compound as a white solid (77 mg, 54% yield). $^1$H NMR (300 MHz, DMSO-d$_6$) 8.73 (bs, 1H), 8.18 (d, J=5.5 Hz, 1H), 7.27 (dd, J=1.7 and 5.5 Hz, 1H), 7.12 (d, J=1.7 Hz, 1H), 7.05 (d, J=8.2 Hz, 1H), 6.56 (dd, J=2.4 and 8.2 Hz, 1H), 6.48 (d, J=2.3 Hz, 1H), 4.20-4.08 (m, 2H), 2.71 (app. t, J=6.2 Hz, 2H), 2.03-1.88 (m, 2H), 1.83-1.58 (m, 2H), 1.36 (s, 3H), 0.82 (t, J=7.4 Hz, 3H). ESIMS m/z [M+H]$^+$ 368.17.

Synthesis of Example 20

Intermediate 2-5:
2-(2,3-dihydrobenzofuran-6-yloxy)-4-iodo-pyridine

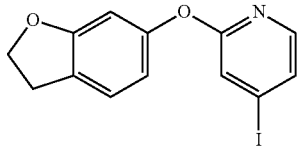 [SMILES: Ic1ccnc(Oc2ccc3c(c2)OCC3)c1]

Essentially following the procedures described for intermediate 1-6, using 2,3-dihydrobenzofuran-6-ol (216 mg, 1.60 mmol) to afford, after purification by silica gel flash chromatography eluting with a gradient of cyclohexane:ethyl acetate—100:0 to 70:30 the title compound as a white solid (100 mg, 21% yield). ESIMS m/z [M+H]$^+$ 340.00.

Example 20: (5R)-3-[2-(2,3-dihydrobenzofuran-6-yloxy)-4-pyridyl]-5-ethyl-5-methyl-imidazolidine-2,4-dione

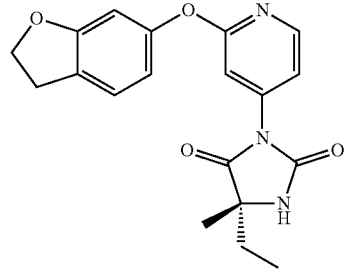 [SMILES: CC[C@@]1(C)NC(=O)N(c2ccnc(Oc3ccc4c(c3)OCC4)c2)C1=O]

Essentially following the procedures described for example 2, using intermediate 2-5 (100 mg, 0.30 mmol) and intermediate 2-1 (52 mg, 0.36 mmol) to afford, after purification by silica gel flash chromatography eluting with a gradient of cyclohexane:ethyl acetate—100:0 to 30:70, the title compound as a white solid (52 mg, 49% yield). $^1$H NMR (300 MHz, DMSO-$d_6$) 8.73 (bs, 1H), 8.19 (d, J=5.5 Hz, 1H), 7.28 (dd, J=1.1 and 5.5 Hz, 1H), 7.21 (d, J=8.4 Hz, 1H), 7.12 (d, J=1.1 Hz, 1H), 6.60-6.52 (m, 2H), 4.56 (t, J=8.6 Hz, 2H), 3.15 (t, J=8.6 Hz, 2H), 1.88-1.58 (m, 2H), 1.36 (s, 3H), 0.82 (t, J=7.4 Hz, 3H). ESIMS m/z [M+H]$^+$ 354.25.

Synthesis of Example 21

Intermediate 2-6: 2-indan-2-yloxy-4-iodo-pyridine

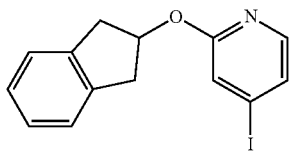 [SMILES: Ic1ccnc(OC2Cc3ccccc3C2)c1]

Essentially following the procedures described for intermediate 1-2, using 2-indanol (160 mg, 1.20 mmol) to afford, after purification by silica gel flash chromatography eluting with a gradient of cyclohexane:ethyl acetate—100:0 to 0:100 the title compound as a white solid (237 mg, 59% yield). ESIMS m/z [M+H]$^+$ 338.17.

Example 21: (5R)-5-ethyl-3-(2-indan-2-yloxy-4-pyridyl)-5-methyl-imidazolidine-2,4-dione

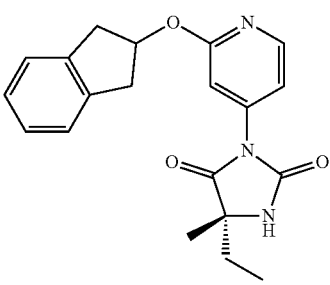 [SMILES: CC[C@@]1(C)NC(=O)N(c2ccnc(OC3Cc4ccccc4C3)c2)C1=O]

Essentially following the procedures described for example 2, using intermediate 2-6 (220 mg, 0.65 mmol) and intermediate 2-1 (102 mg, 0.72 mmol) to afford, after purification by silica gel flash chromatography eluting with a gradient of cyclohexane:ethyl acetate—100:0 to 0:100, the title compound as a white solid (165 mg, 72% yield). $^1$H NMR (300 MHz, DMSO-$d_6$) 8.66 (bs, 1H), 8.25 (d, J=5.6 Hz, 1H), 7.30-7.18 (m, 2H), 7.18-7.03 (m, 3H), 6.84 (d, J=1.5 Hz, 1H), 5.80-5.68 (m, 1H), 3.36 (dd, J=6.1 and 17.0 Hz, 2H), 3.00 (dd, J=2.6 and 17.0 Hz, 2H), 1.80-1.50 (m, 2H), 1.34 (s, 3H), 0.79 (t, J=7.4 Hz, 3H). ESIMS m/z [M+H]$^+$ 352.17.

Intermediate 2-7: (5S)-5-ethyl-5-methyl-imidazolidine-2,4-dione

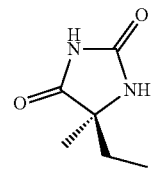

Essentially following the procedures described for intermediate 2-1, using (2S)-2-amino-2-methyl-butanoic acid (1.0 g, 6.51 mmol) to afford after trituration in DCM/MeOH (20/4 mL) and filtration the title compound as a white solid (920 mg, 99% yield). $^1$H NMR (300 MHz, DMSO-$d_6$) 10.55 (bs, 1H), 7.88 (bs, 1H), 1.65-1.42 (m, 2H), 1.20 (s, 3H), 0.74 (t, J=7.4 Hz, 3H).

Synthesis of Example 22

Example 22: (5S)-5-ethyl-3-[2-(3-methoxy-4-methyl-phenoxy)-4-pyridyl]-5-methyl-imidazolidine-2,4-dione

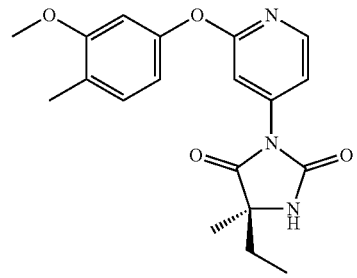 [SMILES: CC[C@]1(C)NC(=O)N(c2ccnc(Oc3ccc(C)c(OC)c3)c2)C1=O]

Essentially following the procedures described for example 1-1, using intermediate 1-2 (224 mg, 0.66 mmol) and intermediate 2-7 (280 mg, 1.97 mmol) to afford, after purification by silica gel flash chromatography eluting with a gradient of cyclohexane:ethyl acetate—100:0 to 0:100, semi-preparative HPLC and lyophilization using water and methanol, the title compound as a white solid (20 mg, 9% yield). $^1$H NMR (300 MHz, DMSO-$d_6$) 8.73 (bs, 1H), 8.20 (d, J=5.5 Hz, 1H), 7.27 (dd, J=1.7 and 5.5 Hz, 1H), 7.18-7.10 (m, 2H), 6.74 (d, J=2.2 Hz, 1H), 6.59 (dd, J=2.2 and 8.0 Hz, 1H), 3.73 (s, 3H), 2.12 (s, 3H), 1.83-1.68 (m, 2H), 1.36 (s, 3H), 0.82 (t, J=7.4 Hz, 3H). ESIMS m/z [M+H]$^+$ 356.42.

Intermediate 2-8: (5R)-5-ethylimidazolidine-2,4-dione

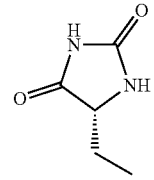

Essentially following the procedures described for intermediate 2-1, using (2R)-2-amino-butanoic acid (300 mg, 2.91 mmol) to afford after trituration in DCM/MeOH (20/4 mL) and filtration the title compound as a white solid (370 mg, 99% yield). $^1$H NMR (300 MHz, DMSO-$d_6$) 10.56 (bs, 1H), 7.90 (bs, 1H), 4.05-3.89 (m, 1H), 1.78-1.44 (m, 2H), 0.83 (t, J=7.4 Hz, 3H).

Synthesis of Example 23

Example 23: (5R)-5-ethyl-3-[2-(3-methoxy-4-methyl-phenoxy)-4-pyridyl]imidazolidine-2,4-dione

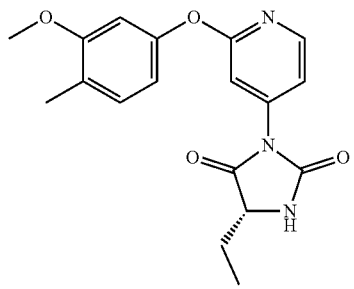 [SMILES: CC[C@H]1NC(=O)N(c2ccnc(Oc3ccc(C)c(OC)c3)c2)C1=O]

Essentially following the procedures described for example 1-1, using intermediate 1-2 (200 mg, 0.59 mmol) and intermediate 2-8 (280 mg, 1.76 mmol) to afford, after purification by silica gel flash chromatography eluting with a gradient of cyclohexane:ethyl acetate—100:0 to 0:100, semi-preparative HPLC and lyophilization using water and methanol, the title compound as a white solid (60 mg, 30% yield). $^1$H NMR (300 MHz, DMSO-$d_6$) 8.74 (bs, 1H), 8.20 (d, J=5.5 Hz, 1H), 7.27 (dd, J=1.7 and 5.5 Hz, 1H), 7.16-7.08 (m, 2H), 6.74 (d, J=2.2 Hz, 1H), 6.59 (dd, J=2.2 and 8.0 Hz, 1H), 4.25-4.12 (m, 1H), 3.73 (s, 3H), 2.12 (s, 3H), 1.87-1.60 (m, 2H), 0.91 (t, J=7.4 Hz, 3H). ESIMS m/z [M+H]$^+$ 342.25.

Synthesis of Example 24

Example 24: 3-[2-(3-methoxy-4-methyl-phenoxy)-4-pyridyl]-1,3-diazaspiro[4.5]decane-2,4-dione

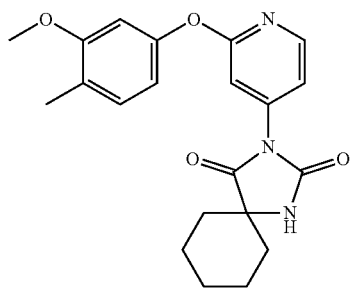 [SMILES: COc1cc(Oc2cc(N3C(=O)NC4(CCCCC4)C3=O)ccn2)ccc1C]

Essentially following the procedures described for example 2, using intermediate 1-2 (150 mg, 0.44 mmol) and 1,3-diazaspiro[4.5]decane-2,4-dione (89 mg, 0.53 mmol) to afford, after purification by silica gel flash chromatography eluting with a gradient of cyclohexane:ethyl acetate—100:0 to 0:100, the title compound as a white solid (21 mg, 12% yield). $^1$H NMR (300 MHz, DMSO-$d_6$) 9.14 (bs, 1H), 8.20 (d, J=5.5 Hz, 1H), 7.29 (dd, J=1.7 and 5.5 Hz, 1H), 7.16-7.10 (m, 2H), 6.73 (d, J=2.2 Hz, 1H), 6.59 (dd, J=2.2 and 8.0 Hz, 1H), 3.73 (s, 3H), 2.12 (s, 3H), 1.80-1.45 (m, 9H), 1.38-1.23 (m, 1H). ESIMS m/z [M+H]$^+$ 382.25.

Synthesis of Example 25

Example 25: 3-[2-[(2,2-difluoro-1,3-benzodioxol-5-yl)oxy]-4-pyridyl]-1,3-diazaspiro[4.5]decane-2,4-dione

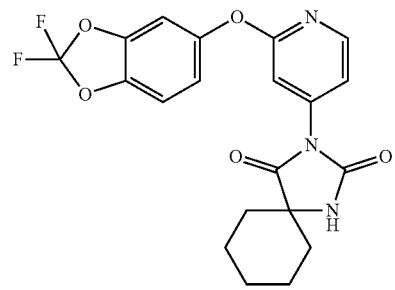

Essentially following the procedures described for example 2, using intermediate 1-12 (250 mg, 0.66 mmol) and 1,3-diazaspiro[4.5]decane-2,4-dione (112 mg, 0.66 mmol) to afford, after purification by silica gel flash chromatography eluting with a gradient of dichloromethane:ethyl acetate—100:0 to 60:40, the title compound as a white solid (178 mg, 64% yield). $^1$H NMR (300 MHz, DMSO-$d_6$) 9.17 (bs, 1H), 8.18 (d, J=5.5 Hz, 1H), 7.43 (d, J=8.7 Hz, 1H), 7.40 (d, J=2.4 Hz, 1H), 7.33 (dd, J=1.6 and 5.5 Hz, 1H), 7.23 (d, J=1.6 Hz, 1H), 6.99 (dd, J=2.4 and 8.7 Hz, 1H), 1.80-1.45 (m, 9H), 1.38-1.23 (m, 1H). ESIMS m/z [M+H]$^+$ 418.17.

Synthesis of Example 26

Example 26: 3-[2-(4-fluoro-3-methoxy-phenoxy)-4-pyridyl]-1,3-diazaspiro[4.5]decane-2,4-dione

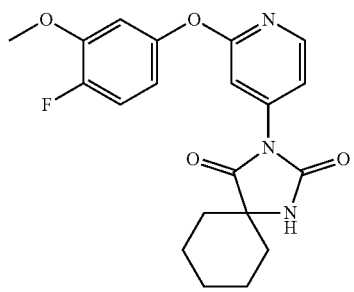 [SMILES: COc1cc(Oc2cc(N3C(=O)NC4(CCCCC4)C3=O)ccn2)ccc1F]

Essentially following the procedures described for example 2, using intermediate 1-7 (260 mg, 0.75 mmol) and 1,3-diazaspiro[4.5]decane-2,4-dione (127 mg, 0.75 mmol) to afford, after purification by silica gel flash chromatography eluting with a gradient of dichloromethane:ethyl acetate—100:0 to 60:40 and lyophilization using water and methanol, the title compound as a white solid (155 mg, 53% yield). $^1$H NMR (300 MHz, DMSO-$d_6$) 9.16 (bs, 1H), 8.20 (d, J=5.5 Hz, 1H), 7.37-7.16 (m, 3H), 7.00 (dd, J=2.7 and 7.5 Hz, 1H), 6.73-6.64 (m, 1H), 3.79 (s, 3H), 1.80-1.45 (m, 9H), 1.38-1.23 (m, 1H). ESIMS m/z [M+H]$^+$ 386.33.

Synthesis of Example 27

Intermediate 3-1: 2-(2,3-dihydro-1,4-benzodioxin-6-yloxy)-4-iodo-pyridine

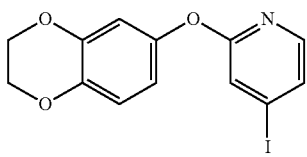 [SMILES: Ic1ccnc(Oc2ccc3c(c2)OCCO3)c1]

Essentially following the procedures described for intermediate 1-2, using 2,3-dihydro-1,4-benzodioxin-6-ol (490 mg, 3.22 mmol) to afford, after purification by silica gel flash chromatography eluting with a gradient of cyclohexane:ethyl acetate—100:0 to 75:25 the title compound as a colorless gum (720 mg, 66% yield). $^1$H NMR (300 MHz, CHCl$_3$-d) 7.86 (d, J=5.3 Hz, 1H), 7.31 (dd, J=1.3 and 5.3 Hz, 1H), 7.26 (dd, J=1.3 and 5.8 Hz, 1H), 6.87 (d, J=8.7 Hz, 1H), 6.66 (d, J=2.7 Hz, 1H), 6.60 (dd, J=2.7 and 8.7 Hz, 1H), 4.33-4.19 (m, 4H).

Example 27: 3-[2-(2,3-dihydro-1,4-benzodioxin-6-yloxy)-4-pyridyl]-1,3-diazaspiro[4.5]decane-2,4-dione

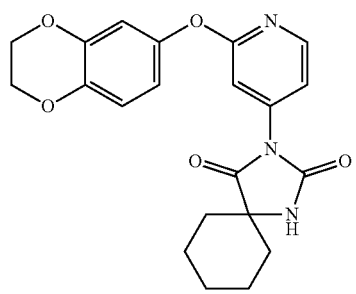 [SMILES: O=C1NC2(CCCCC2)C(=O)N1c1ccnc(Oc2ccc3c(c2)OCCO3)c1]

Essentially following the procedures described for example 2, using intermediate 3-1 (270 mg, 0.76 mmol) and 1,3-diazaspiro[4.5]decane-2,4-dione (128 mg, 0.76 mmol) to afford, after purification by silica gel flash chromatography eluting with a gradient of cyclohexane:ethyl acetate—100:0 to 0:100 and lyophilization using water and methanol, the title compound as a white solid (188 mg, 62% yield). $^1$H NMR (300 MHz, DMSO-d$_6$) 9.17 (bs, 1H), 8.19 (d, J=5.5 Hz, 1H), 7.29 (dd, J=1.7 and 5.5 Hz, 1H), 7.14 (d, J=1.7 Hz, 1H), 6.87 (d, J=8.7 Hz, 1H), 6.67 (d, J=2.7 Hz, 1H), 6.60 (dd, J=2.7 and 8.7 Hz, 1H), 4.33-4.19 (m, 4H), 1.80-1.50 (m, 9H), 1.38-1.23 (m, 1H). ESIMS m/z [M+H]$^+$ 396.33.

Synthesis of Example 28

Intermediate 3-2: 2-(3,4-dimethoxyphenoxy)-4-iodo-pyridine

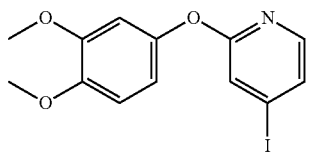

Essentially following the procedures described for intermediate 1-2, using 3,4-dimethoxy phenol (1.0 g, 6.49 mmol) to afford, after purification by silica gel flash chromatography eluting with a gradient of cyclohexane:ethyl acetate—100:0 to 75:25 the title compound as a colorless gum (1.52 g, 85% yield). $^1$H NMR (300 MHz, CHCl$_3$-d) 7.86 (d, J=5.3 Hz, 1H), 7.31 (dd, J=1.3 and 5.3 Hz, 1H), 7.28 (d, J=1.3 Hz, 1H), 6.95-6.82 (m, 1H), 6.75-6.61 (m, 2H), 3.88 (s, 3H), 3.85 (s, 3H).

Example 28: 3-[2-(3,4-dimethoxyphenoxy)-4-pyridyl]-1,3-diazaspiro[4.5]decane-2,4-dione

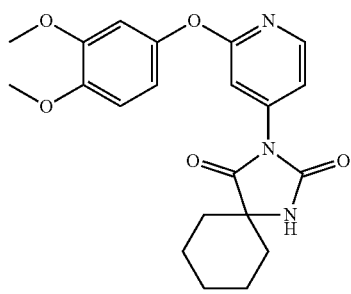 [SMILES: COc1ccc(Oc2cc(N3C(=O)NC4(CCCCC4)C3=O)ccn2)cc1OC]

Essentially following the procedures described for example 2, using intermediate 3-2 (400 mg, 1.12 mmol) and 1,3-diazaspiro[4.5]decane-2,4-dione (188 mg, 1.12 mmol) to afford, after purification by silica gel flash chromatography eluting with a gradient of cyclohexane:ethyl acetate—100:0 to 0:100 and lyophilization using water and methanol, the title compound as a white solid (290 mg, 64% yield). $^1$H NMR (300 MHz, DMSO-d$_6$) 9.14 (bs, 1H), 8.19 (d, J=5.5 Hz, 1H), 7.27 (dd, J=1.7 and 5.5 Hz, 1H), 7.11 (d, J=1.7 Hz, 1H), 6.95 (d, J=8.7 Hz, 1H), 6.78 (d, J=2.7 Hz, 1H), 6.63 (dd, J=2.7 and 8.7 Hz, 1H), 3.74 (s, 3H), 3.70 (s, 3H), 1.80-1.40 (m, 9H), 1.38-1.23 (m, 1H). ESIMS m/z [M+H]$^+$ 398.33.

Synthesis of Example 29

Intermediate 3-3: 4-methyl-3-(trifluoromethoxy)phenol

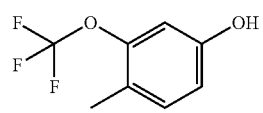

Essentially following the procedures described for intermediate 1-1, using 4-hydroxy-2-(trifluoromethoxy)benzaldehyde (1.44 g, 7.00 mmol) in ethanol/aqueous 12N HCl (50 mL/1.5 mL) to afford, after purification by silica gel flash chromatography eluting with a gradient of cyclohexane: ethyl acetate—100:0 to 60:40 the title compound as a pale yellow oil (1.04 g, 78% yield). $^1$H NMR (300 MHz, CHCl$_3$-d) 7.08 (d, J=8.3 Hz, 1H), 6.73 (d, J=1.4 Hz, 1H), 6.68 (dd, J=2.5 and 8.3 Hz, 1H), 2.22 (s, 3H).

Intermediate 3-4: 4-iodo-2-[4-methyl-3-(trifluoromethoxy)phenoxy]pyridine

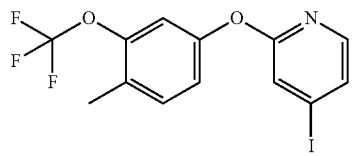 [SMILES: Cc1ccc(Oc2cc(I)ccn2)cc1OC(F)(F)F]

Essentially following the procedures described for intermediate 1-6, using intermediate 3-3 (500 mg, 2.60 mmol) to afford, after purification by silica gel flash chromatography eluting with a gradient of cyclohexane:ethyl acetate—100:0 to 75:25 the title compound as a colorless oil (475 mg, 69% yield). $^1$H NMR (300 MHz, CHCl$_3$-d) 7.84 (d, J=5.3 Hz, 1H), 7.40-7.33 (m, 2H), 7.27 (d, J=8.1 Hz, 1H), 7.03-6.95 (m, 2H), 2.31 (s, 3H).

Example 29: 3-[2-[4-methyl-3-(trifluoromethoxy)phenoxy]-4-pyridyl]-1,3-diazaspiro[4.5]decane-2,4-dione

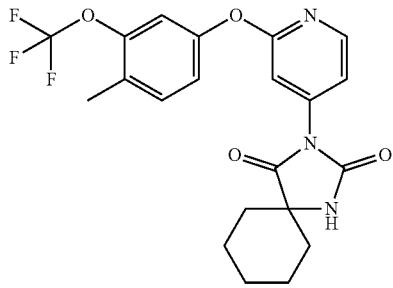 [SMILES: Cc1ccc(Oc2cc(N3C(=O)NC4(CCCCC4)C3=O)ccn2)cc1OC(F)(F)F]

Essentially following the procedures described for example 2, using intermediate 3-4 (245 mg, 0.62 mmol) and 1,3-diazaspiro[4.5]decane-2,4-dione (105 mg, 0.62 mmol) to afford, after purification by silica gel flash chromatography eluting with a gradient of cyclohexane:ethyl acetate—100:0 to 50:50 and lyophilization using water and methanol, the title compound as a white foam (115 mg, 42% yield). $^1$H NMR (300 MHz, DMSO-d$_6$) 9.17 (bs, 1H), 8.20 (d, J=5.5 Hz, 1H), 7.42 (d, J=8.4 Hz, 1H), 7.35 (dd, J=1.7 and 5.5 Hz, 1H), 7.24 (d, J=1.7 Hz, 1H), 7.17-7.7.08 (m, 2H), 2.26 (s, 3H), 1.80-1.45 (m, 9H), 1.38-1.25 (m, 1H). ESIMS m/z [M+H]$^+$ 436.25.

Synthesis of Example 30

Example 30: 3-[2-(3-methoxy-4-methyl-phenoxy)-4-pyridyl]-8-methyl-1,3,8-triazaspiro[4.5]decane-2,4-dione

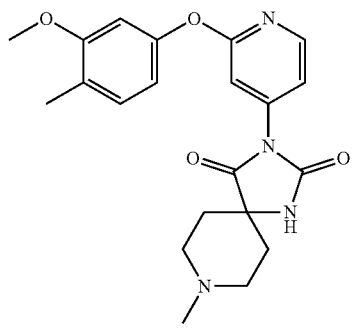 [SMILES: COc1cc(Oc2cc(N3C(=O)NC4(CCN(C)CC4)C3=O)ccn2)ccc1C]

Essentially following the procedures described for example 2, using intermediate 1-2 (200 mg, 0.59 mmol) and 8-methyl-1,3,8-triazaspiro[4.5]decane-2,4-dione (130 mg, 0.70 mmol) to afford, after purification by silica gel flash chromatography eluting with a gradient of dichloromethane:methanol—100:0 to 80:20, the title compound as a white solid (92 mg, 38% yield). $^1$H NMR (300 MHz, DMSO-d$_6$) 9.15 (bs, 1H), 8.20 (d, J=5.5 Hz, 1H), 7.29 (dd, J=1.7 and 5.5 Hz, 1H), 7.16-7.10 (m, 2H), 6.73 (d, J=2.2 Hz, 1H), 6.59 (dd, J=2.2 and 8.0 Hz, 1H), 3.73 (s, 3H), 2.77-2.61 (m, 2H), 2.35-2.26 (m, 2H), 2.25 (s, 3H), 2.20 (s, 3H), 1.97-1.82 (m, 2H), 1.79-1.63 (m, 2H). ESIMS m/z [M+H]$^+$ 397.42.

Synthesis of Example 31

Example 31: 3-[2-(3-methoxy-4-methyl-phenoxy)-4-pyridyl]-8-thia-1,3-diazaspiro[4.5]decane-2,4-dione

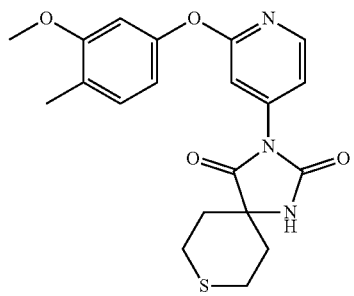 [SMILES: COc1cc(Oc2cc(N3C(=O)NC4(CCSCC4)C3=O)ccn2)ccc1C]

Essentially following the procedures described for example 2, using intermediate 1-2 (200 mg, 0.59 mmol) and 8-thia-1,3-diazaspiro[4.5]decane-2,4-dione (130 mg, 0.70 mmol) to afford, after purification by silica gel flash chromatography eluting with a gradient of cyclohexane:ethyl acetate—100:0 to 0:100, the title compound as a white solid (102 mg, 43% yield). $^1$H NMR (300 MHz, DMSO-d$_6$) 9.22 (bs, 1H), 8.21 (d, J=5.5 Hz, 1H), 7.28 (dd, J=1.7 and 5.5 Hz, 1H), 7.16-7.10 (m, 2H), 6.73 (d, J=2.2 Hz, 1H), 6.59 (dd, J=2.2 and 8.0 Hz, 1H), 3.73 (s, 3H), 2.90-2.78 (m, 2H), 2.74-2.58 (m, 2H), 2.12 (s, 3H), 2.08-1.92 (m, 4H). ESIMS m/z [M+H]$^+$ 400.33.

Synthesis of Example 32

Intermediate 3-5: 8-oxa-1,3-diazaspiro[4.5]decane-2,4-dione

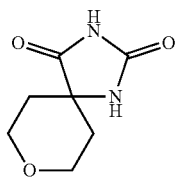 [SMILES: O=C1NC(=O)C2(CCOCC2)N1]

To a suspension of tetrahydro-4H-pyran-4-one (1.0 g, 10.00 mmol) in methanol/water (6 mL/6 mL) was added potassium cyanide (976 mg, 15.00 mmol) and ammonium carbonate (2.88 g, 30.00 mmol). The mixture was stirred in a micro-wave at 90° C. for 30 minutes and let at room temperature for 18 h. The precipitate formed was filtered and washed with water to give the title compound as a white solid (620 mg, 37% yield). $^1$H NMR (300 MHz, DMSO-$d_6$) 10.64 (bs, 1H), 8.55 (bs, 1H), 3.83-3.74 (m, 2H), 3.62-3.50 (m, 2H), 1.90-1.75 (m, 2H), 1.54-1.38 (m, 2H).

Example 32: 3-[2-(3-methoxy-4-methyl-phenoxy)-4-pyridyl]-8-oxa-1,3-diazaspiro[4.5]decane-2,4-dione

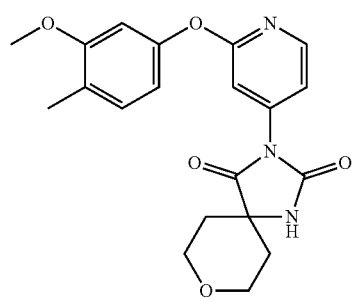 [SMILES: COc1cc(Oc2cc(N3C(=O)NC4(CCOCC4)C3=O)ccn2)ccc1C]

Essentially following the procedures described for example 2, using intermediate 1-2 (300 mg, 0.88 mmol) and 8-oxa-1,3-diazaspiro[4.5]decane-2,4-dione (180 mg, 1.06 mmol) to afford, after purification by silica gel flash chromatography eluting with a gradient of cyclohexane:ethyl acetate—100:0 to 0:100 and lyophilization using water and methanol, the title compound as a white foam (43 mg, 13% yield). $^1$H NMR (300 MHz, DMSO-$d_6$) 9.33 (bs, 1H), 8.21 (d, J=5.5 Hz, 1H), 7.30 (dd, J=1.7 and 5.5 Hz, 1H), 7.16-7.10 (m, 2H), 6.73 (d, J=2.2 Hz, 1H), 6.59 (dd, J=2.2 and 8.0 Hz, 1H), 3.90-3.78 (m, 2H), 3.74 (s, 3H), 3.72-3.58 (m, 2H), 2.12 (s, 3H), 2.02-1.88 (m, 2H), 1.78-1.60 (m, 2H). ESIMS m/z [M+H]$^+$ 384.33.

Synthesis of Example 33

Example 33: 3-[2-(3-methoxy-4-methyl-phenoxy)-4-pyridyl]-1,3-diazaspiro[4.4]nonane-2,4-dione

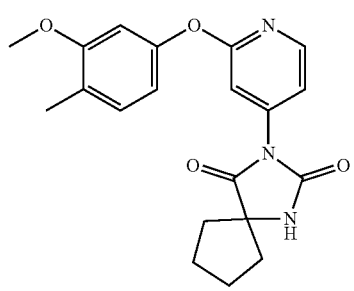 [SMILES: COc1cc(Oc2cc(N3C(=O)NC4(CCCC4)C3=O)ccn2)ccc1C]

Essentially following the procedures described for example 2, using intermediate 1-2 (200 mg, 0.59 mmol) and 1,3-diazaspiro[4.4]nonane-2,4-dione (110 mg, 0.70 mmol) to afford, after purification by silica gel flash chromatography eluting with a gradient of cyclohexane:ethyl acetate—100:0 to 0:100, semi-preparative HPLC and lyophilization using water and methanol, the title compound as a white foam (26 mg, 12% yield). $^1$H NMR (300 MHz, DMSO-$d_6$) 8.95 (bs, 1H), 8.21 (d, J=5.5 Hz, 1H), 7.30 (dd, J=1.7 and 5.5 Hz, 1H), 7.16-7.10 (m, 2H), 6.73 (d, J=2.2 Hz, 1H), 6.59 (dd, J=2.2 and 8.0 Hz, 1H), 3.73 (s, 3H), 2.12 (s, 3H), 2.10-1.96 (m, 2H), 1.88-1.68 (m, 6H). ESIMS m/z [M+H]$^+$ 368.33.

Synthesis of Example 34

Intermediate 3-6: 5,7-diazaspiro[3.4]octane-6,8-dione

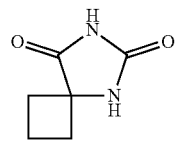

Essentially following the procedures described for example 2-1, using 1-amino-1-cyclobutanecarboxylic acid (300 mg, 0.88 mmol) to afford, after purification by silica gel flash chromatography eluting with a gradient of cyclohexane:ethyl acetate—100:0 to 0:100, the title compound as a white solid (910 mg, 50% yield). ESIMS m/z [M+H]$^+$ 141.00.

Example 34: 7-[2-(3-methoxy-4-methyl-phenoxy)-4-pyridyl]-5,7-diazaspiro[3.4]octane-6,8-dione

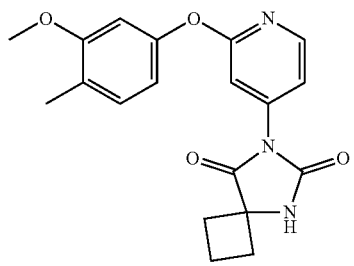 [SMILES: COc1cc(Oc2cc(N3C(=O)NC4(CCC4)C3=O)ccn2)ccc1C]

Essentially following the procedures described for example 2, using intermediate 1-2 (200 mg, 0.59 mmol) and intermediate 3-6 (99 mg, 0.70 mmol) to afford, after purification by silica gel flash chromatography eluting with a gradient of cyclohexane:ethyl acetate—100:0 to 0:100, semi-preparative HPLC and lyophilization using water and methanol, the title compound as a white foam (14 mg, 7% yield). $^1$H NMR (300 MHz, MeOH-d) 8.19 (d, J=5.5 Hz, 1H), 7.39 (dd, J=1.7 and 5.5 Hz, 1H), 7.19-7.10 (m, 2H), 6.71 (d, J=2.2 Hz, 1H), 6.30 (dd, J=2.2 and 8.1 Hz, 1H), 3.80 (s, 3H), 3.69-3.52 (m, 2H), 2.51-2.38 (m, 2H), 2.18 (s, 3H), 2.17-2.01 (m, 1H), 1.98-1.80 (m, 1H). ESIMS m/z [M+H]$^+$ 354.25.

Synthesis of Example 35

Example 35: 3-[2-(1,3-benzodioxol-5-yloxy)-4-pyridyl]-1,3-diazaspiro[4.5]decane-2,4-dione

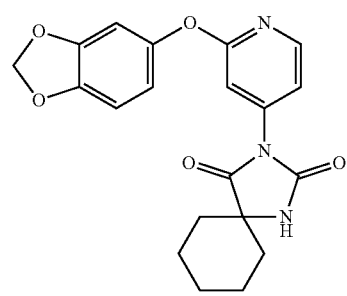 [SMILES: O=C1NC2(CCCCC2)C(=O)N1c1ccnc(Oc2ccc3c(c2)OCO3)c1]

Essentially following the procedures described for example 2, using intermediate 1-8 (270 mg, 0.79 mmol) and 1,3-diazaspiro[4.5]decane-2,4-dione (133 mg, 0.79 mmol) to afford, after purification by silica gel flash chromatography eluting with a gradient of cyclohexane:ethyl acetate—100:0 to 50:50, the title compound as a white foam (115 mg, 38% yield). $^1$H NMR (300 MHz, DMSO-d$_6$) 9.15 (bs, 1H), 8.18 (d, J=5.5 Hz, 1H), 7.28 (dd, J=1.4 and 5.5 Hz, 1H), 7.13 (d, J=1.4 Hz, 1H), 6.91 (d, J=8.4 Hz, 1H), 6.80 (d, J=2.3 Hz, 1H), 6.58 (dd, J=2.3 and 8.4 Hz, 1H), 6.04 (s, 2H), 1.80-1.45 (m, 9H), 1.38-1.23 (m, 1H). ESIMS m/z [M+H]$^+$ 382.25.

Synthesis of Example 36

Example 36: 3-[2-[(2,2-difluoro-1,3-benzodioxol-5-yl)oxy]-4-pyridyl]-1,3-diazaspiro[4.4]nonane-2,4-dione

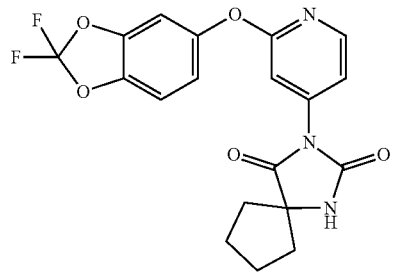 [SMILES: O=C1NC2(CCCC2)C(=O)N1c1ccnc(Oc2ccc3c(c2)OC(F)(F)O3)c1]

Essentially following the procedures described for example 2, using intermediate 1-12 (184 mg, 0.49 mmol) and 1,3-diazaspiro[4.4]nonane-2,4-dione (75 mg, 0.49 mmol) to afford, after purification by silica gel flash chromatography eluting with a gradient of cyclohexane:ethyl acetate—100:0 to 50:50, the title compound as a white solid (136 mg, 67% yield). $^1$H NMR (300 MHz, DMSO-d$_6$) 8.97 (bs, 1H), 8.18 (d, J=5.6 Hz, 1H), 7.43 (d, J=8.7 Hz, 1H), 7.40 (d, J=2.3 Hz, 1H), 7.35 (dd, J=1.7 and 5.6 Hz, 1H), 7.24 (d, J=1.6 Hz, 1H), 6.99 (dd, J=2.4 and 8.7 Hz, 1H), 2.16-1.98 (m, 2H), 1.89-1.68 (m, 6H). ESIMS m/z [M+H]$^+$ 404.42.

Synthesis of Example 37

Example 37: 7-[2-[(2,2-difluoro-1,3-benzodioxol-5-yl)oxy]-4-pyridyl]-5,7-diazaspiro[3.4]octane-6,8-dione

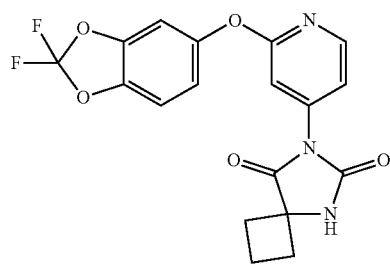 [SMILES: O=C1NC2(CCC2)C(=O)N1c1ccnc(Oc2ccc3c(c2)OC(F)(F)O3)c1]

Essentially following the procedures described for example 2, using intermediate 1-12 (200 mg, 0.53 mmol) and 5,7-diazaspiro[3.4]octane-2,4-dione (75 mg, 0.53 mmol) to afford, after purification by silica gel flash chromatography eluting with a gradient of cyclohexane:ethyl acetate—100:0 to 50:50, the title compound as a white solid (146 mg, 70% yield). $^1$H NMR (300 MHz, DMSO-d$_6$) 9.10 (bs, 1H), 8.18 (d, J=5.6 Hz, 1H), 7.43 (d, J=8.7 Hz, 1H), 7.40 (d, J=2.3 Hz, 1H), 7.33 (dd, J=1.6 and 5.6 Hz, 1H), 7.22 (d, J=1.6 Hz, 1H), 6.99 (dd, J=2.4 and 8.7 Hz, 1H), 2.60-2.50 (m, 2H), 2.41-2.26 (m, 2H), 2.07-1.89 (m, 1H), 1.89-1.70 (m, 1H). ESIMS m/z [M+H]$^+$ 390.17.

Synthesis of Example 38

Intermediate 4-1: 3-brome-5-(3-methoxy-4-methyl-phenoxy)pyridine

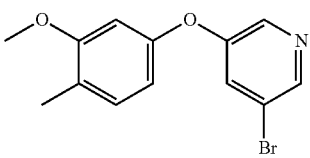 [SMILES: COc1cc(Oc2cncc(Br)c2)ccc1C]

To a reaction vessel charged with intermediate 1-1 (528 mg, 3.82 mmol) and 3,5-dibromopyridine (905 mg, 3.82 mmol) in NMP (15 mL) was added $Cs_2CO_3$ (1.24 g, 3.82 mmol). The vessel was sealed and the mixture allowed to stir for 24 h at 100° C. The mixture was diluted with EtOAc, washed with a saturated aqueous solution of $NH_4Cl$ and brine, dried over $MgSO_4$ and concentrated in vacuo before purification by flash chromatography on silica, eluting with cyclohexane then gradient elution with 0%-50% EtOAc/Cyclohexane mixtures to give the title compound as a colorless oil (440 mg, 39% yield). $^1$H NMR (300 MHz, DMSO-$d_6$) 8.45 (d, J=2.0 Hz, 1H), 8.35 (d, J=2.4 Hz, 1H), 7.62 (dd, J=2.0 and 2.4 Hz, 1H), 7.18 (dd, J=0.7 and 8.1 Hz, 1H), 6.80 (d, J=2.3 Hz, 1H), 6.58 (dd, J=2.3 and 8.1 Hz, 1H), 3.77 (s, 3H), 2.13 (s, 3H).

Intermediate 4-2: tert-butyl N-[5-(3-methoxy-4-methyl-phenoxy)-3-pyridyl]carbamate

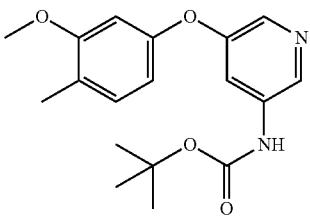 [SMILES: COc1cc(Oc2cncc(NC(=O)OC(C)(C)C)c2)ccc1C]

To a reaction vessel charged with intermediate 4-1 (430 mg, 1.46 mmol) in dioxane (15 mL) was added tert-butyl carbamate (205 mg, 1.75 mmol) and $Cs_2CO_3$ (666 mg, 2.04 mmol). The mixture was degazed with argon for 15 min and then XantPhos (12 mg, 0.02 mmol) and tris(dibenzylideneacetone)dipalladium(0)-chloroform adduct (7.5 mg, 0.007 mmol) were added. The vessel was sealed and the mixture allowed to stir for 24 h at 100° C. The mixture was hydrolyzed with water, extracted with EtOAc, the organics were washed with brine, dried over $MgSO_4$ and concentrated in vacuo before purification by flash chromatography on silica, eluting with cyclohexane then gradient elution with 0%-100% EtOAc/Cyclohexane mixtures to give the title compound as a yellow gum (460 mg, 92% yield). $^1$H NMR (300 MHz, $CHCl_3$-d) 8.19 (d, J=2.0 Hz, 1H), 8.03 (d, J=2.5 Hz, 1H), 7.65 (bs, 1H), 7.08 (bs, 1H), 7.06 (d, J=8.0 Hz, 1H), 6.56 (d, J=2.3 Hz, 1H), 6.49 (dd, J=2.3 and 8.0 Hz, 1H), 3.77 (s, 3H), 2.17 (s, 3H), 1.47 (s, 9H).

Intermediate 4-3: 5-(3-methoxy-4-methyl-phenoxy)pyridin-3-amine Hydrochloride

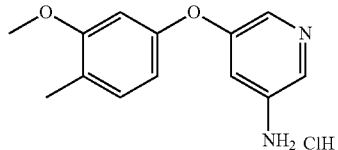 [SMILES: COc1cc(Oc2cncc(N)c2)ccc1C ; Cl]

To a solution of intermediate 4-2 (455 mg, 1.41 mmol) in methanol (10 mL) at room temperature was added 4.0N HCl in dioxane (3.0 mL) and the mixture allowed to stir for 18 h at rt. The mixture was concentrated in vacuo to give the title compound as a pale yellow solid (365 mg, 97% yield). $^1$H NMR (300 MHz, DMSO-$d_6$) 7.86 (d, J=2.0 Hz, 1H), 7.77 (d, J=2.0 Hz, 1H), 7.24 (d, J=8.7 Hz, 1H), 7.05 (m, 1H), 6.85 (d, J=2.2 Hz, 1H), 6.68 (dd, J=2.3 and 8.1 Hz, 1H), 3.78 (s, 3H), 2.15 (s, 3H).

Intermediate 4-4: tert-butyl N-[(1R)-1-[[5-(3-methoxy-4-methyl-phenoxy)-3-pyridyl]carbamoyl]propyl]carbamate

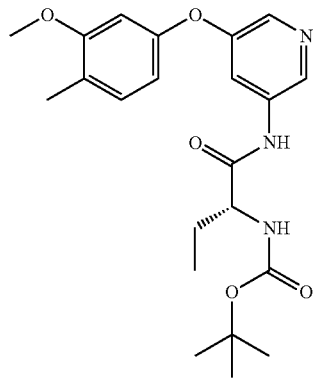 [SMILES: CC[C@@H](NC(=O)OC(C)(C)C)C(=O)Nc1cncc(Oc2ccc(C)c(OC)c2)c1]

To a solution of Boc-D-Abu-OH (341 mg, 1.68 mmol) in DMF (3 mL) was added DIEA (735 μL, 4.2 mmol) followed by HATU (640 mg, 1.68 mmol) and the mixture allowed to stir for 15 min at rt. Then a solution of intermediate 4-3 (365 mg, 1.40 mmol) and DIEA (735 μL, 4.2 mmol) in THF (2 mL) was added and the mixture allowed to stir for 24 h at rt. The mixture was hydrolyzed with a saturated aqueous solution of $NH_4Cl$, extracted with EtOAc, the organics were washed with brine, dried over $MgSO_4$ and concentrated in vacuo before purification by flash chromatography on silica, eluting with cyclohexane then gradient elution with 0%-75% EtOAc/Cyclohexane mixtures to give the title compound as a colorless oil (370 mg, 63% yield). $^1$H NMR (300 MHz, $CHCl_3$-d) 9.17 (bs, 1H), 8.26 (d, J=2.0 Hz, 1H), 8.05 (d, J=2.2 Hz, 1H), 7.79 (d, J=2.0 Hz, 1H), 7.05 (d, J=8.0 Hz, 1H), 6.57 (d, J=2.2 Hz, 1H), 6.49 (dd, J=2.2 and 8.0 Hz, 1H), 5.35 (d, J=6.3 Hz, 1H), 4.23 (m, 1H), 3.77 (s, 3H), 2.17 (s, 3H), 1.94-1.82 (m, 1H), 1.76-1.61 (m, 1H), 1.49 (s, 9H), 1.25 (t, J=7.1 Hz, 3H).

Intermediate 4-5: (2R)-2-amino-N-[5-(3-methoxy-4-methyl-phenoxy)-3-pyridyl]butanamide

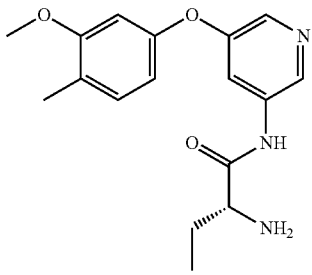 [SMILES: CC[C@@H](N)C(=O)Nc1cncc(Oc2ccc(C)c(OC)c2)c1]

To a solution of intermediate 4-4 (370 mg, 0.88 mmol) in DCM (25 mL) at 0° C. was added TFA (4 mL) and the mixture allowed to stir for 2 h at rt. The mixture made basic using NaHCO$_3$, extracted with DCM, dried over MgSO$_4$ and concentrated in vacuo to give the title compound as a colorless oil (280 mg, Quant.). $^1$H NMR (300 MHz, CHCl$_3$-d) 9.71 (bs, 1H), 8.37 (d, J=2.0 Hz, 1H), 8.11 (d, J=2.5 Hz, 1H), 7.92 (m, 1H), 7.08 (d, J=8.0 Hz, 1H), 6.58 (d, J=2.3 Hz, 1H), 6.52 (dd, J=2.3 and 8.0 Hz, 1H), 3.79 (s, 3H), 3.42 (m, 1H), 2.19 (s, 3H), 2.05-1.90 (m, 1H), 1.77-1.55 (m, 1H), 1.01 (t, J=7.4 Hz, 3H).

Example 38: (5R)-5-ethyl-3-[5-(3-methoxy-4-methyl-phenoxy)-3-pyridyl]imidazolidine-2,4-dione

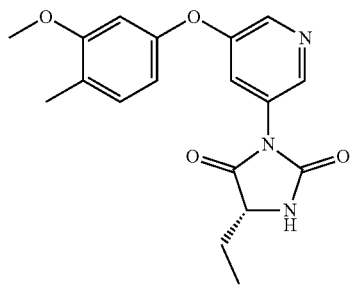 [SMILES: CC[C@H]1NC(=O)N(c2cncc(Oc3ccc(C)c(OC)c3)c2)C1=O]

To a solution of intermediate 4-5 (280 mg, 0.88 mmol) in DCM (20 mL) at 0° C. was added TEA (617 μL, 4.43 mmol) and a solution of triphosgene (127 mg, 0.39 mmol) in DCM (6 mL). The mixture was allowed to stir for 30 min at 0° C. The mixture was hydrolyzed with water, extracted with DCM, dried over MgSO$_4$ and concentrated in vacuo. The residue was triturated in EtOAc/MeOH (1 mL/1 mL) and Et$_2$O was added until precipitation occurred. After filtration the title compound was obtained as a beige solid (85 mg, 28% yield). $^1$H NMR (300 MHz, DMSO-d$_6$) 8.66 (bs, 1H), 8.37 (d, J=2.4 Hz, 1H), 7.45 (m, 1H), 7.18 (d, J=8.1 Hz, 1H), 6.78 (d, J=2.3 Hz, 1H), 6.58 (dd, J=2.3 and 8.1 Hz, 1H), 4.16 (t, J=2.9 Hz, 1H), 3.77 (s, 3H), 2.13 (s, 3H), 1.84-1.62 (m, 2H), 0.93 (t, J=7.4 Hz, 3H). ESIMS m/z [M+H]$^+$ 342.17.

Synthesis of Example 39

Example 39: 3-[5-(3-methoxy-4-methyl-phenoxy)-3-pyridyl]-5,5-dimethyl-imidazolidine-2,4-dione

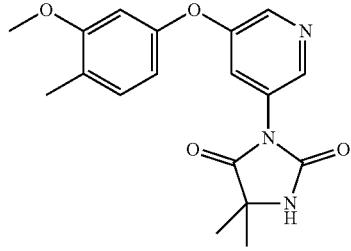 [SMILES: COc1cc(Oc2cncc(N3C(=O)NC(C)(C)C3=O)c2)ccc1C]

Essentially following the procedures described for example 2, using intermediate 4-1 (190 mg, 0.65 mmol) to afford, after purification by silica gel flash chromatography eluting with a gradient of cyclohexane:ethyl acetate—100:0 to 0:100, the title compound as a white foam (28 mg, 13% yield). $^1$H NMR (300 MHz, DMSO-d$_6$) 8.63 (bs, 1H), 8.45-8.25 (m, 2H), 7.48 (bs, 1H), 7.16 (d, J=7.9 Hz, 1H), 6.88-6.70 (m, 1H), 6.56 (d, J=8.1 Hz, 1H), 3.74 (s, 3H), 2.11 (s, 3H), 1.36 (s, 6H). ESIMS m/z [M+H]$^+$ 342.33.

Synthesis of Example 40

Example 40: (5R)-5-ethyl-3-[5-(3-methoxy-4-methyl-phenoxy)-3-pyridyl]-5-methyl-imidazolidine-2,4-dione

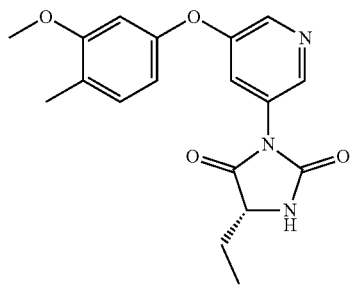 [SMILES: CC[C@H]1NC(=O)N(c2cncc(Oc3ccc(C)c(OC)c3)c2)C1=O]

Essentially following the procedures described for example 2, using intermediate 4-1 (340 mg, 1.16 mmol) and intermediate 2-1 (181 mg, 1.27 mmol) to afford, after purification by silica gel flash chromatography eluting with a gradient of cyclohexane:ethyl acetate—100:0 to 0:100, the title compound as a white solidified oil (230 mg, 56% yield). $^1$H NMR (300 MHz, DMSO-d$_6$) 8.63 (bs, 1H), 8.38-8.33 (m, 2H), 7.50-7.45 (m, 1H), 7.16 (d, J=8.1 Hz, 1H), 6.76 (d, J=2.3 Hz, 1H), 6.56 (dd, J=2.3 and 8.1 Hz, 1H), 3.75 (s, 3H), 2.11 (s, 3H), 1.80-1.55 (m, 2H), 1.20 (s, 3H), 0.82 (t, J=7.4 Hz, 3H). ESIMS m/z [M+H]$^+$ 356.33.

Synthesis of Example 41

Intermediate 5-1: 4-(3-methoxy-4-methyl-phenoxy)pyridin-2-amine

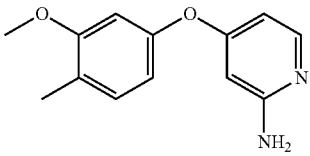 [SMILES: COc1cc(Oc2ccnc(N)c2)ccc1C]

To a microwave reaction vessel charged with intermediate 1-1 (450 mg, 3.24 mmol), 2-amino-4-chloropyridine (500 mg, 3.89 mmol) in NMP (7 mL) was added $Cs_2CO_3$ (1.27 g, 3.89 mmol). The vessel was sealed and the mixture heated in a microwave oven for 1 h at 220° C. The mixture was diluted with $Et_2O$, washed with $H_2O$ and brine, dried over $MgSO_4$ and concentrated in vacuo before purification by flash chromatography on silica, eluting with cyclohexane then gradient elution with 0%-100% EtOAc/Cyclohexane mixtures to give the title compound as a yellow oil (190 mg, 41% yield). ESIMS m/z [M+H]$^+$ 231.0

Intermediate 5-2: tert-butyl N-[(1R)-1-[[4-(3-methoxy-4-methyl-phenoxy)-2-pyridyl]carbamoyl]propyl]carbamate

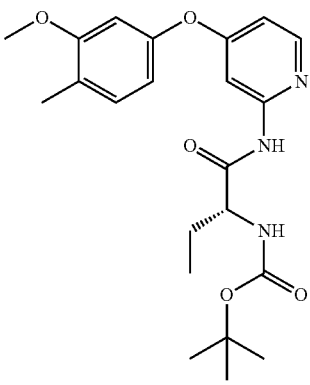 [SMILES: CC[C@@H](NC(=O)OC(C)(C)C)C(=O)Nc1cc(Oc2ccc(C)c(OC)c2)ccn1]

To a solution of Boc-D-Abu-OH (335 mg, 1.65 mmol) in DMF (3 mL) was added DIEA (430 μL, 2.48 mmol) followed by HBTU (750 mg, 1.98 mmol) and the mixture allowed to stir for 30 min at rt. Then a solution of intermediate 5-1 (190 mg, 0.82 mmol) in DMF (2 mL) was added and the mixture allowed to stir for 18 h at 110° C. The mixture was hydrolyzed with water, extracted with $Et_2O$, the organics were washed with brine, dried over $MgSO_4$ and concentrated in vacuo before purification by flash chromatography on silica, eluting with cyclohexane then gradient elution with 0%-50% EtOAc/Cyclohexane mixtures to give the title compound as a yellow oil (290 mg, 84% yield). ESIMS m/z [M+H]$^+$ 416.1

Intermediate 5-3: (2R)-2-amino-N-[4-(3-methoxy-4-methyl-phenoxy)-2-pyridyl]butanamide

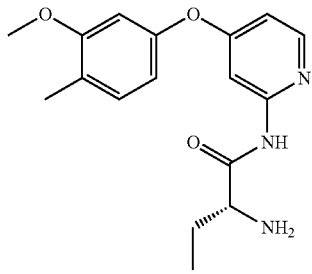 [SMILES: CC[C@@H](N)C(=O)Nc1cc(Oc2ccc(C)c(OC)c2)ccn1]

Essentially following the procedures described for example 4-5, using intermediate 5-2 (290 mg, 0.69 mmol) to afford the title compound as a yellow oil (160 mg, 73% yield). $^1$H NMR (300 MHz, CHCl$_3$-d) 8.11 (d, J=5.7 Hz, 1H), 7.88 (d, J=2.2 Hz, 1H), 7.12 (d, J=7.5 Hz, 1H), 6.60 (m, 3H), 3.79 (s, 3H), 3.46 (m, 1H), 2.20 (s, 3H), 1.93 (m, 1H), 1.64 (m, 1H), 1.00 (t, J=7.5 Hz, 3H).

Example 41: (5R)-5-ethyl-3-[4-(3-methoxy-4-methyl-phenoxy)-2-pyridyl]imidazolidine-2,4-dione

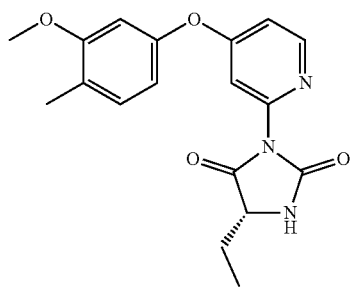 [SMILES: CC[C@H]1NC(=O)N(c2cc(Oc3ccc(C)c(OC)c3)ccn2)C1=O]

To a solution of intermediate 5-3 (160 mg, 0.51 mmol) in DCM (10 mL) at room temperature was added TEA (430 μL, 3.04 mmol) and carbonyl diimidazole (250 mg, 1.52 mmol). The mixture was allowed to stir for 3 h at rt. The mixture was hydrolyzed with water, extracted with DCM, dried over $MgSO_4$ and concentrated in vacuo before purification by flash chromatography on silica, eluting with cyclohexane then gradient elution with 0%-100% EtOAc/Cyclohexane mixtures to give the title compound as a white foam (85 mg, 49% yield). $^1$H NMR (300 MHz, DMSO-d$_6$) 8.49 (bs, 1H), 8.39 (d, J=5.7 Hz, 1H), 7.22 (d, J=8.6 Hz, 1H), 6.96 (m, 1H), 6.91 (d, J=2.3 Hz, 1H), 6.81 (d, J=2.3 Hz, 1H), 6.67 (dd, J=2.3 and 8.0 Hz, 1H), 4.15 (m, 1H), 3.75 (s, 3H), 2.13 (s, 3H), 1.76-1.61 (m, 2H), 0.91 (t, J=7.4 Hz, 3H). ESIMS m/z [M+H]$^+$ 342.0

Synthesis of Example 42

Intermediate 5-4: 4-(2-naphthyloxy)pyridin-2-amine

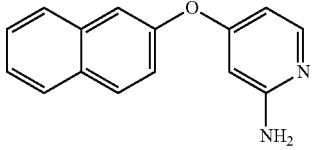 [SMILES: Nc1cc(Oc2ccc3ccccc3c2)ccn1]

Essentially following the procedures described for example 5-1, using naphtalene-2-ol (467 mg, 3.24 mmol) to afford, after purification by silica gel flash chromatography eluting with a gradient of cyclohexane:ethyl acetate—100:0 to 0:100, the title compound as a white powder (580 mg, 75% yield). ESIMS m/z [M+H]+ 237.3.

Intermediate 5-5: tert-butyl N-[(1R)-1-[[4-(2-naphthyloxy)-2-pyridyl]carbamoyl]propyl]carbamate

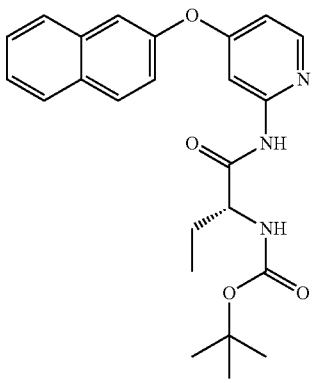

To a solution of intermediate 5-4 (580 mg, 2.40 mmol) in DMF (20 mL) was added Boc-D-Abu-OH (490 mg, 2.40 mmol), 1-hydroxybenzotriazole (442 mg, 2.89 mmol), EDC (553 mg, 2.89 mmol) and DIEA (930 μL, 9.62 mmol). The mixture was allowed to stir for 48 h at 80° C. The mixture was hydrolyzed with water, extracted with Et2O, the organics were washed with brine, dried over MgSO4 and concentrated in vacuo before purification by silica gel flash chromatography eluting with a gradient of cyclohexane:ethyl acetate—100:0 to 30:70 to give the title compound as a yellow oil (233 mg, 23% yield). ESIMS m/z [M+H]+ 422.2

Intermediate 5-6: (2R)-2-amino-N-[4-(2-naphthyloxy)-2-pyridyl]butanamide

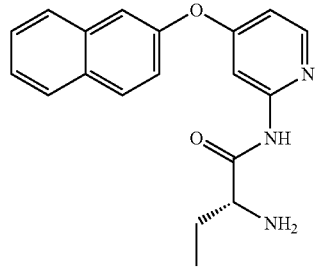 [SMILES: CC[C@@H](N)C(=O)Nc1cc(Oc2ccc3ccccc3c2)ccn1]

Essentially following the procedures described for example 4-5, using intermediate 5-5 (230 mg, 0.55 mmol) to afford the title compound as a yellow solid (142 mg, 81% yield). ESIMS m/z [M+H]+ 322.3

Example 42: (5R)-5-ethyl-3-[4-(2-naphthyloxy)-2-pyridyl]imidazolidine-2,4-dione

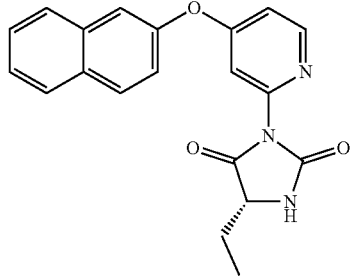 [SMILES: CC[C@H]1NC(=O)N(c2cc(Oc3ccc4ccccc4c3)ccn2)C1=O]

Essentially following the procedures described for example 5-1, using intermediate 5-6 (140 mg, 0.44 mmol) to afford, after purification by silica gel flash chromatography eluting with a gradient of ethyl acetate:methanol—100:0 to 95:5, the title compound as a white foam (104 mg, 65% yield). 1H NMR (300 MHz, DMSO-d6) 8.48 (bs, 1H), 8.43 (d, J=5.7 Hz, 1H), 8.06 (d, J=8.8 Hz, 1H), 8.02-7.88 (m, 2H), 7.76 (d, J=2.3 Hz, 1H), 7.60-7.48 (m, 2H), 7.38 (dd, J=2.5 and 8.8 Hz, 1H), 7.05 (dd, J=2.3 and 5.7 Hz, 1H), 6.98 (d, J=2.3 Hz, 1H), 4.16-4.10 (m, 1H), 1.82-1.55 (m, 2H), 0.89 (t, J=7.4 Hz, 3H). ESIMS m/z [M+H]+ 348.33

Synthesis of Example 43

Intermediate 5-7: 4-(2-phenylphenoxy)pyridin-2-amine

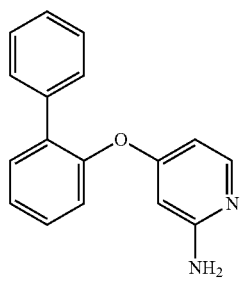 [SMILES: Nc1cc(Oc2ccccc2-c2ccccc2)ccn1]

Essentially following the procedures described for example 5-1, using 2-phenylphenol (550 mg, 3.24 mmol) to afford, after purification by silica gel flash chromatography eluting with a gradient of cyclohexane:ethyl acetate—100:0 to 0:100, the title compound as a white solid (600 mg, 70% yield). ESIMS m/z [M+H]$^+$ 236.3.

Intermediate 5-8: tert-butyl N-[(1R)-1-[[4-(2-phenylphenoxy)-2-pyridyl]carbamoyl]propyl]carbamate

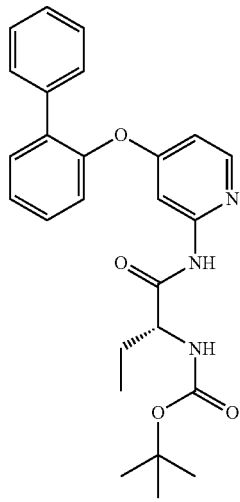 [SMILES: CC[C@@H](NC(=O)OC(C)(C)C)C(=O)Nc1cc(Oc2ccccc2-c2ccccc2)ccn1]

Essentially following the procedures described for intermediate 5-5, using intermediate 5-7 (600 mg, 2.29 mmol) to afford, after purification by silica gel flash chromatography eluting with a gradient of cyclohexane:ethyl acetate—100:0 to 70:30, the title compound as a white solid (200 mg, 17% yield). ESIMS m/z [M+H]$^+$ 448.4

Intermediate 5-9: (2R)-2-amino-N-[4-(2-phenylphenoxy)-2-pyridyl]butanamide

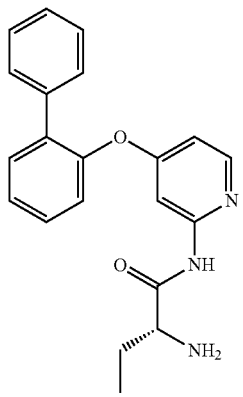 [SMILES: CC[C@@H](N)C(=O)Nc1cc(Oc2ccccc2-c2ccccc2)ccn1]

Essentially following the procedures described for example 4-5, using intermediate 5-8 (200 mg, 0.45 mmol) to afford the title compound as a yellow solid (137 mg, 88% yield). ESIMS m/z [M+H]$^+$ 348.3

Example 5-3: (5R)-5-ethyl-3-[4-(2-phenylphenoxy)-2-pyridyl]imidazolidine-2,4-dione

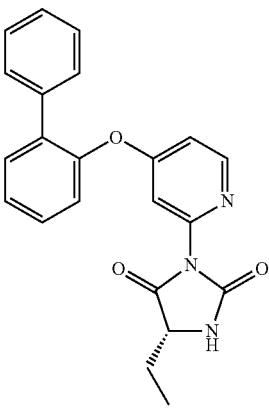 [SMILES: CC[C@H]1NC(=O)N(c2cc(Oc3ccccc3-c3ccccc3)ccn2)C1=O]

Essentially following the procedures described for example 5-1, using intermediate 5-9 (140 mg, 0.44 mmol) to afford, after purification by silica gel flash chromatography eluting with a gradient of ethyl acetate:methanol—100:0 to 95:5 and lyophilization using water and methanol, the title compound as a white solid (83 mg, 54% yield). $^1$H NMR (300 MHz, DMSO-d$_6$) 8.47 (bs, 1H), 8.34-8.28 (m, 1H), 7.59-7.23 (m, 9H), 6.87-6.81 (m, 2H), 4.16-4.10 (m, 1H), 1.82-1.55 (m, 2H), 0.89 (t, J=7.4 Hz, 3H). ESIMS m/z [M+H]$^+$ 374.33

Synthesis of Example 44

Intermediate 5-10: 2-bromo-4-(3-bromo-5-methoxy-4-methyl-phenoxy)pyridine

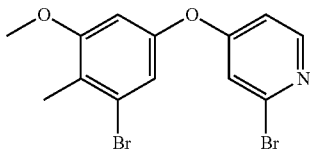 [SMILES: COc1cc(Oc2ccnc(Br)c2)cc(Br)c1C]

To a solution of intermediate 5-1 (500 mg, 2.17 mmol) in HBr 48% in water (5 mL) cooled at 0° C. was added dropwise bromine (335 μL, 6.51 mmol) followed by a solution of sodium nitrite (750 mg, 10.85 mmol) in water (10 mL). The reaction mixture was stirred at 0° C. for 1 h and the pH was adjusted to 13 using 5N NaOH. The mixture was extracted with EtOAc, washed with a saturated aqueous solution of Na₂S203 and brine, dried over MgSO₄ and concentrated in vacuo before purification by silica gel flash chromatography eluting with a gradient of cyclohexane:ethyl acetate—100:0 to 60:40, the title compound as an orange oil (475 mg, 58% yield). ESIMS m/z [M+H]⁺ 374.2.

Intermediate 5-11: 3-[4-(3-bromo-5-methoxy-4-methyl-phenoxy)-2-pyridyl]-5,5-dimethyl-imidazolidine-2,4-dione

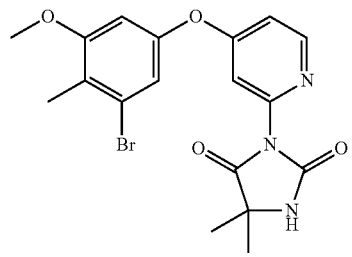 [SMILES: COc1cc(Oc2ccnc(N3C(=O)NC(C)(C)C3=O)c2)cc(Br)c1C]

Essentially following the procedures described for example 2, using intermediate 5-10 (475 mg, 1.27 mmol) to afford, after purification by silica gel flash chromatography eluting with a gradient of cyclohexane:ethyl acetate—100:0 to 0:100 and semi-preparative HPLC, the title compound as a white solid (60 mg, 11% yield). ESIMS m/z [M+H]⁺ 420.42

Example 44: 3-[4-(3-methoxy-4-methyl-phenoxy)-2-pyridyl]-5,5-dimethyl-imidazolidine-2,4-dione

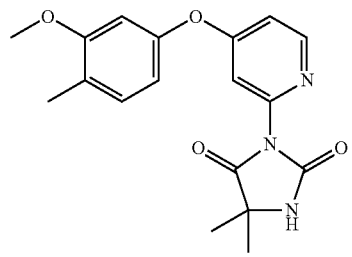 [SMILES: COc1cc(Oc2ccnc(N3C(=O)NC(C)(C)C3=O)c2)ccc1C]

To a solution of intermediate 5-11 (65 mg, 0.15 mmol) in methanol (15 mL) was added 10% palladium on activated carbon (17 mg). The mixture was evacuated and back-filled with H₂ (×3) and was left under 4 bars of H₂, stirring at room temperature for 7 h. The reaction mixture was filtered through Celite, rinsing with EtOAc before concentration in vacuo. The crude product thus obtained was purified by silica gel flash chromatography eluting with a gradient of cyclohexane:ethyl acetate—100:0 to 0:100 to give the title compound as a white foam (28 mg, 52% yield). ¹H NMR (300 MHz, DMSO-d₆) 8.52 (bs, 1H), 8.39 (d, J=5.5 Hz, 1H), 7.22 (d, J=8.0 Hz, 1H), 7.01-6.93 (m, 2H), 6.81 (d, J=2.2 Hz, 1H), 6.67 (dd, J=2.2 and 8.0 Hz, 1H), 3.76 (s, 3H), 2.14 (s, 3H), 1.35 (s, 6H). ESIMS m/z [M+H]⁺ 342.33

Synthesis of Example 45

Intermediate 5-12: (5R)-3-[4-(3-bromo-5-methoxy-4-methyl-phenoxy)-2-pyridyl]-5-ethyl-5-methyl-imidazolidine-2,4-dione

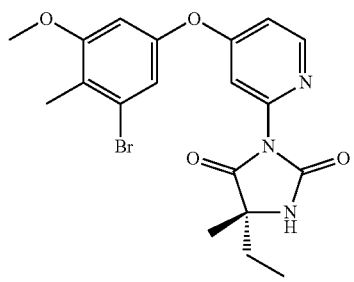 [SMILES: CC[C@@]1(C)NC(=O)N(c2cc(Oc3cc(Br)c(C)c(OC)c3)ccn2)C1=O]

Essentially following the procedures described for example 2, using intermediate 5-10 (200 mg, 0.54 mmol) and intermediate 2-1 (80 mg, 0.56 mmol) to afford, after purification by silica gel flash chromatography eluting with a gradient of dichloromethane:ethyl acetate—100:0 to 0:100, the title compound as a mixture with an unidentified by-product (140 mg, est. purity=80%, 48% est. yield). ESIMS m/z [M+H]⁺ 434.0

Example 45: (5R)-5-ethyl-3-[4-(3-methoxy-4-methyl-phenoxy)-2-pyridyl]-5-methyl-imidazolidine-2,4-dione

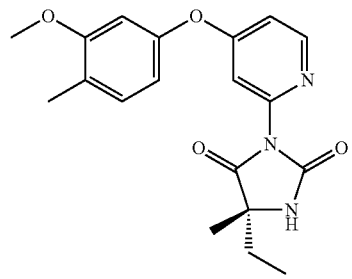 [SMILES: CC[C@@]1(C)NC(=O)N(c2cc(Oc3ccc(C)c(OC)c3)ccn2)C1=O]

Essentially following the procedures described for example 5-4, using intermediate 5-12 (130 mg, 0.30 mmol) to afford, after purification by silica gel flash chromatography eluting with a gradient of cyclohexane:ethyl acetate—100:0 to 0:100, the title compound as a white solid (80 mg, 72% yield). ¹H NMR (300 MHz, DMSO-d₆) 8.47 (bs, 1H), 8.42-8.36 (m, 1H), 7.22 (d, J=8.2 Hz, 1H), 6.98-6.90 (m, 2H), 6.81 (d, J=2.2 Hz, 1H), 6.67 (dd, J=2.2 and 8.2 Hz, 1H), 3.76 (s, 3H), 2.14 (s, 3H), 1.80-1.55 (m, 2H), 1.33 (s, 3H), 0.83 (t, J=7.4 Hz, 3H). ESIMS m/z [M+H]$^+$ 356.25

Synthesis of Example 46

Intermediate 5-13: (5S)-3-[4-(3-bromo-5-methoxy-4-methyl-phenoxy)-2-pyridyl]-5-ethyl-5-methyl-imidazolidine-2,4-dione

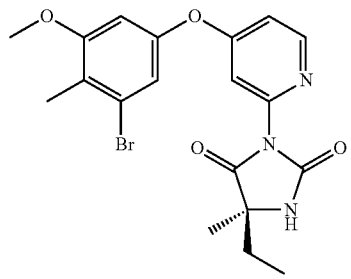 [SMILES: CC[C@]1(C)NC(=O)N(c2cc(Oc3cc(Br)c(C)c(OC)c3)ccn2)C1=O]

Essentially following the procedures described for example 2, using intermediate 5-10 (300 mg, 0.81 mmol) and intermediate 2-7 (120 mg, 0.86 mmol) to afford, after purification by silica gel flash chromatography eluting with a gradient of dichloromethane:ethyl acetate—100:0 to 0:100, the title compound as a yellow oil (150 mg, est. purity=60%, 26% est. yield). ESIMS m/z [M+H]$^+$ 434.0

Example 46: (5S)-5-ethyl-3-[4-(3-methoxy-4-methyl-phenoxy)-2-pyridyl]-5-methyl-imidazolidine-2,4-dione

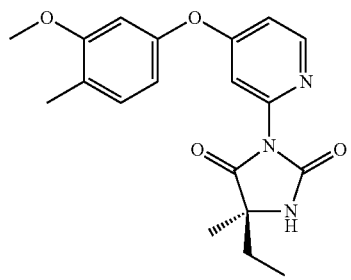 [SMILES: CC[C@]1(C)NC(=O)N(c2cc(Oc3ccc(C)c(OC)c3)ccn2)C1=O]

Essentially following the procedures described for example 5-4, using intermediate 5-13 (est. 95 mg, 0.22 mmol) to afford, after purification by silica gel flash chromatography eluting with a gradient of ethyl acetate:methanol—100:0 to 95:5, the title compound as a yellow oil (35 mg, 41% yield). $^1$H NMR (300 MHz, DMSO-d$_6$) 8.47 (bs, 1H), 8.42-8.36 (m, 1H), 7.22 (d, J=8.2 Hz, 1H), 6.98-6.90 (m, 2H), 6.81 (d, J=2.2 Hz, 1H), 6.67 (dd, J=2.2 and 8.2 Hz, 1H), 3.76 (s, 3H), 2.14 (s, 3H), 1.80-1.55 (m, 2H), 1.34 (s, 3H), 0.83 (t, J=7.4 Hz, 3H). ESIMS m/z [M+H]$^+$ 356.33

Synthesis of Example 47

Intermediate 5-14: 4-hydroxy-2-isopropyl-benzonitrile

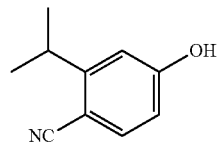

A solution of 4-iodo-3-isopropyl-phenol (900 mg, 3.43 mmol) in NMP (15 mL) was treated with cyanocopper (400 mg, 4.46 mmol) and stirred at 180° C. for 1.5 hours. The reaction mixture was cooled to 20° C. and diluted with 200 mL of diethylether. The resulting suspension was filtered through celite. The filtrate was washed with water, the organic extract was dried over MgSO$_4$, filtered and the solvent was evaporated in vacuo. The residue was purified by silica gel flash chromatography eluting with a gradient of cyclohexane:ethyl acetate—100:0 to 50:50, the title compound as a white solid (454 mg, 82% yield). $^1$H NMR (300 MHz, CHCl$_3$-d) 7.46 (d, J=8.4 Hz, 1H), 6.82 (d, J=2.5 Hz, 1H), 6.71 (dd, J=2.5 and 8.4 Hz, 1H), 5.51 (s, 1H), 3.32 (sept., J=6.8 Hz, 1H), 1.28 (d, J=6.8 Hz, 6H).

Intermediate 5-15: 3-(4-chloro-2-pyridyl)-5,5-dimethyl-imidazolidine-2,4-dione

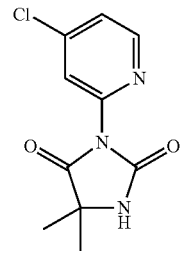 [SMILES: CC1(C)NC(=O)N(c2cc(Cl)ccn2)C1=O]

Essentially following the procedures described for example 2, using 2-bromo-4-chloropyridine (300 mg, 1.56 mmol) to afford, after purification by silica gel flash chromatography eluting with a gradient of cyclohexane:ethyl acetate—100:0 to 0:100, the title compound as a colorless oil (187 mg, 47% yield). ESIMS m/z [M+H]$^+$ 240.25.

Example 47: 4-[[2-(4,4-dimethyl-2,5-dioxo-imidazolidin-1-yl)-4-pyridyl]oxy]-2-isopropyl-benzonitrile

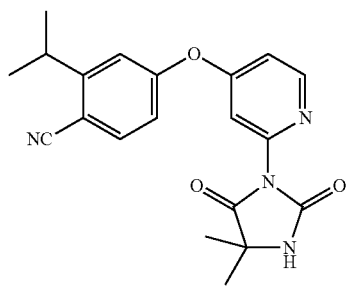 [SMILES: CC(C)c1cc(Oc2ccnc(N3C(=O)NC(C)(C)C3=O)c2)ccc1C#N]

To a solution of Intermediate 5-14 (117 mg, 0.73 mmol) in DMSO (5 mL) was added potassium tert-butoxide (164 mg, 1.46 mmol) and the mixture was stirred 15 minutes at room temperature. Intermediate 5-15 (185 mg, 0.73 mmol) was added and the mixture was stirred 6 h at 160° C. The reaction mixture was hydrolyzed using an aqueous saturated solution of NH$_4$Cl and extracted with Et2O (2×50 mL) and EtOAc (1×50 mL). The combined organic extracts were dried over magnesium sulfate, filtered and the solvent was evaporated in vacuo. The residue was purified by silica gel flash chromatography eluting with a gradient of cyclohexane:ethyl acetate—100:0 to 0:100, a semi-preparative HPLC and lyophilization using water and methanol, to afford the title compound as a white foam (11 mg, 4% yield). $^1$H NMR (300 MHz, DMSO-d$_6$) 8.56 (bs, 1H), 8.49 (d, J=5.6 Hz, 1H), 7.29 (dd, J=1.7 and 5.6 Hz, 1H), 7.90 (d, J=8.5 Hz, 1H), 7.37 (d, J=2.4 Hz, 1H), 7.19 (dd, J=2.4 and 8.5 Hz, 1H), 7.14 (d, J=2.2 Hz, 1H), 7.11 (dd, J=2.4 and 5.6 Hz, 1H), 3.23 (sept., J=6.8 Hz, 1H), 1.36 (s, 6H), 1.25 (d, J=6.8 Hz, 6H). ESIMS m/z [M+H]$^+$ 365.33.

Synthesis of Example 48

Intermediate 6-1: 6-(3-methoxy-4-methyl-phenoxy)pyridin-2-amine

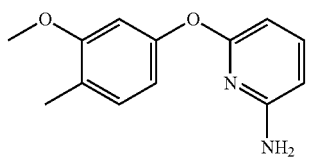 [SMILES: COc1cc(Oc2cccc(N)n2)ccc1C]

To a microwave reaction vessel charged with 3-methoxy-4-methyl-phenol (200 mg, 1.44 mmol), 2-amino-6-fluoropyridine (200 mg, 1.73 mmol) in NMP (3 mL) was added Cs$_2$CO$_3$ (565 mg, 1.73 mmol). The vessel was sealed and the mixture allowed to stir for 1 h at 220° C. The mixture was diluted with Et$_2$O, washed with H$_2$O and brine, dried over MgSO$_4$ and concentrated in vacuo before purification by flash chromatography on silica, eluting with cyclohexane then gradient elution with 0%-50% EtOAc/Cyclohexane mixtures to give the title compound as a yellow oil (300 mg, 90% yield). $^1$H NMR (300 MHz, CHCl$_3$-d) 7.38 (app. t, J=7.9 Hz, 1H), 7.09 (d, J=8.3 Hz, 1H), 6.62 (m, 2H), 6.19 (d, J=7.9 Hz, 1H), 6.02 (d, J=7.9 Hz, 1H), 3.78 (s, 3H), 2.19 (s, 3H).

Intermediate 6-2: tert-butyl N-[(1R)-1-[[6-(3-methoxy-4-methyl-phenoxy)-2-pyridyl]carbamoyl]propyl]carbamate

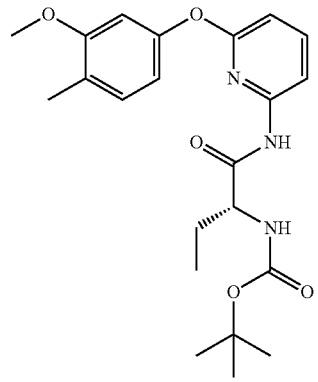 [SMILES: CC[C@@H](NC(=O)OC(C)(C)C)C(=O)Nc1cccc(Oc2ccc(C)c(OC)c2)n1]

To a solution of Boc-D-Abu-OH (1.14 g, 5.63 mmol) in DMF (10 mL) was added DIEA (1.9 mL, 11.26 mmol) followed by HATU (2.14 g, 5.63 mmol) and the mixture allowed to stir for 30 min at rt. Then a solution of 6-(3-methoxy-4-methyl-phenoxy)pyridin-2-amine (865 mg, 3.76 mmol) in THF (10 mL) was added and the mixture allowed to stir for 24 h at 50° C. An extra amount of Boc-D-Abu-OH (1.14 g, 5.63 mmol), DIEA (1.9 mL, 11.26 mmol) and HATU (2.14 g, 5.63 mmol) was added and the mixture allowed to stir for 24 h at 50° C. The mixture was hydrolyzed with a saturated aqueous solution of NH$_4$Cl, extracted with EtOAc, the organics were washed with brine, dried over MgSO$_4$ and concentrated in vacuo before purification by flash chromatography on silica, eluting with cyclohexane then gradient elution with 0%-60% EtOAc/Cyclohexane mixtures to give the title compound as a yellow oil (1.0 g, 68% yield). ESIMS m/z [M+H]$^+$ 416.1

Intermediate 6-3: (2R)-2-amino-N-[6-(3-methoxy-4-methyl-phenoxy)-2-pyridyl]butanamide trifluoroacetate

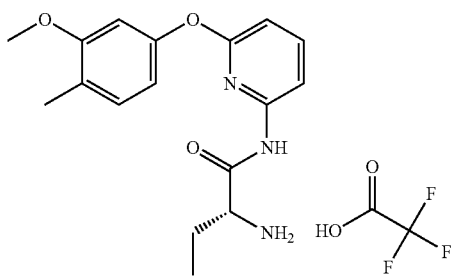 [SMILES: CC[C@@H](N)C(=O)Nc1cccc(Oc2ccc(C)c(OC)c2)n1 ; O=C(O)C(F)(F)F]

To a solution of tert-butyl N-[(1R)-1-[[6-(3-methoxy-4-methyl-phenoxy)-2-pyridyl]carbamoyl]propyl]carbamate (650 mg, 1.56 mmol) in DCM (10 mL) at 0° C. was added TFA (1.5 mL) and the mixture allowed to stir for 5 h at rt. The mixture was concentrated in vacuo to give the title compound as a beige foam (610 mg, 90% yield). ESIMS m/z [M+H]$^+$ 316.33

Example 48: (5R)-5-ethyl-3-[6-(3-methoxy-4-methyl-phenoxy)-2-pyridyl]imidazolidine-2,4-dione

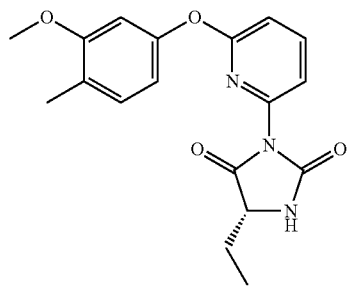 [SMILES: CC[C@H]1NC(=O)N(c2cccc(Oc3ccc(C)c(OC)c3)n2)C1=O]

To a solution of (2R)-2-amino-N-[6-(3-methoxy-4-methyl-phenoxy)-2-pyridyl]butanamide trifluoroacetate (610 mg, 1.44 mmol) in DCM (40 mL) at room temperature was added TEA (800 µL, 8.62 mmol) and mixture was allowed to stir for 30 min at rt. Carbonyl diimidazole (441 mg, 4.31 mmol) and TEA (400 µL, 4.31 mmol) were added at 0° C. and the mixture was allowed to stir for 2 h at rt. The mixture was hydrolyzed with an aqueous solution of hydrochloric acid (1.0 N), extracted with DCM, dried over MgSO$_4$ and concentrated in vacuo before purification by flash chromatography on silica, eluting with cyclohexane then gradient elution with 0%-100% EtOAc/Cyclohexane mixtures to give after lyophilization the title compound as a white solid (350 mg, 72% yield). $^1$H NMR (300 MHz, DMSO-d$_6$) 8.53 (bs, 1H), 7.99 (app. t, J=7.6 Hz, 1H), 7.12 (m, 2H), 6.99 (d, J=8.2 Hz, 1H), 6.82 (d, J=2.2 Hz, 1H), 6.64 (dd, J=2.2 and 8.1 Hz, 1H), 4.20 (t, J=5.7 Hz, 1H), 3.76 (s, 3H), 2.12 (s, 3H), 1.80-1.60 (m, 2H), 0.91 (t, J=7.3 Hz, 3H). ESIMS m/z [M+H]$^+$ 342.33

Synthesis of Example 49

Intermediate 6-4: 6-(2-naphthyloxy)pyridin-2-amine

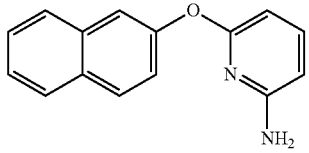 [SMILES: Nc1cccc(Oc2ccc3ccccc3c2)n1]

Essentially following the procedures described for intermediate 6-1, using naphtalene-2-ol (770 mg, 5.35 mmol) to afford, after purification by silica gel flash chromatography eluting with a gradient of cyclohexane:ethyl acetate—100:0 to 75:25, the title compound as a light brown solid (1.18 g, 93% yield). $^1$H NMR (300 MHz, CHCl$_3$-d) 7.90-7.73 (m, 3H), 7.55-7.38 (m, 4H), 7.29 (dd, J=2.4 and 8.9 Hz, 1H), 6.21 (d, J=7.9 Hz, 1H), 6.14 (d, J=7.9 Hz, 1H), 4.38 (bs, 2H).

Intermediate 6-5: tert-butyl N-[(1R)-1-[[6-(2-naphthyloxy)-2-pyridyl]carbamoyl]propyl]carbamate

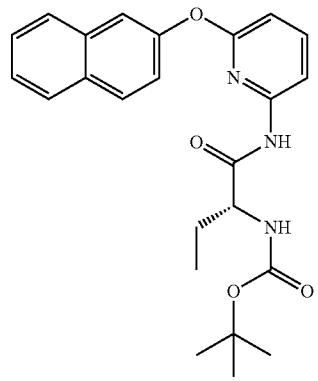 [SMILES: CC[C@@H](NC(=O)OC(C)(C)C)C(=O)Nc1cccc(Oc2ccc3ccccc3c2)n1]

Essentially following the procedures described for intermediate 6-2, using intermediate 6-4 (750 mg, 3.17 mmol) to afford, after purification by silica gel flash chromatography eluting with a gradient of cyclohexane:ethyl acetate—100:0 to 80:20, the title compound as a white foam (780 mg, 58% yield). $^1$H NMR (300 MHz, CHCl$_3$-d) 8.11 (bs, 1H), 7.79 (d, J=7.9 Hz, 1H), 7.56 (app. t, J=8.0 Hz, 1H), 7.61-7.20 (m, 6H), 7.14 (dd, J=1.4 and 7.9 Hz, 1H), 6.41 (d, J=8.0 Hz, 1H), 5.02-4.85 (m, 1H), 4.20-4.02 (m, 1H), 2.00-1.83 (m, 1H), 1.72-1.58 (m, 1H), 1.43 (s, 9H), 0.97 (t, J=7.4 Hz, 3H).

Intermediate 6-6: (2R)-2-amino-N-[6-(2-naphthyloxy)-2-pyridyl]butanamide

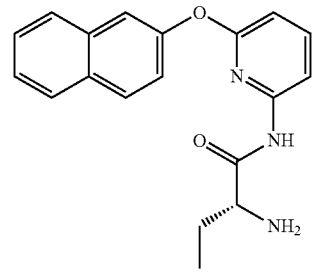 [SMILES: CC[C@@H](N)C(=O)Nc1cccc(Oc2ccc3ccccc3c2)n1]

Essentially following the procedures described for intermediate 6-3, using intermediate 6-5 (750 mg, 3.17 mmol) to afford, after hydrolysis with a saturated aqueous solution of NaHCO$_3$, extraction with DCM, drying over MgSO$_4$, filtration and evaporation under reduced pressure, the title compound as a colorless gum (400 mg, 68% yield). $^1$H NMR (300 MHz, CHCl$_3$-d) 8.02-7.79 (m, 5H), 7.63 (d, J=2.3 Hz, 1H), 7.58-7.42 (m, 2H), 7.33 (dd, J=2.4 and 8.8 Hz, 1H), 6.74 (dd, J=1.3 and 7.4 Hz, 1H), 3.30-3.18 (m, 1H), 1.72-1.56 (m, 1H), 1.49-1.32 (m, 1H), 0.84 (t, J=7.4 Hz, 3H).

Example 49: (5R)-5-ethyl-3-[6-(2-naphthyloxy)-2-pyridyl]imidazolidine-2,4-dione

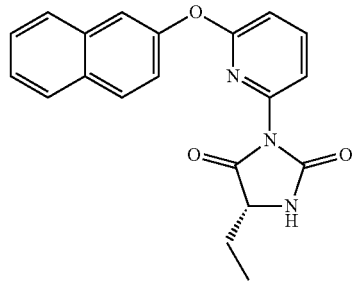 [SMILES: CC[C@H]1NC(=O)N(c2cccc(Oc3ccc4ccccc4c3)n2)C1=O]

Essentially following the procedures described for example 6-1, using intermediate 6-6 (395 mg, 1.23 mmol) to afford, after purification by silica gel flash chromatography eluting with a gradient of cyclohexane:ethyl acetate—100:0 to 50:50, the title compound as a colorless varnish (380 mg, 86% yield). $^1$H NMR (300 MHz, DMSO-$d_6$) 8.51 (bs, 1H), 8.09-7.83 (m, 4H), 7.75 (d, J=2.4 Hz, 1H), 7.57-7.45 (m, 2H), 7.37 (dd, J=2.4 and 8.9 Hz, 1H), 7.18 (d, J=7.5 Hz, 1H), 7.12 (d, J=7.6 Hz, 1H), 4.21-4.15 (m, 1H), 1.82-1.55 (m, 2H), 0.89 (t, J=7.3 Hz, 3H). ESIMS m/z [M+H]$^+$ 348.33

Synthesis of Example 50

Intermediate 6-7: 6-(2-phenylphenoxy)pyridin-2-amine

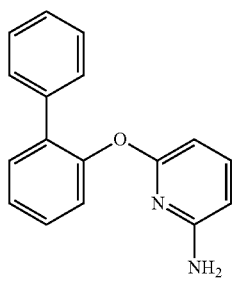 [SMILES: Nc1cccc(Oc2ccccc2-c2ccccc2)n1]

Essentially following the procedures described for intermediate 6-1, using 2-phenylphenol (910 mg, 5.35 mmol) to afford, after purification by silica gel flash chromatography eluting with a gradient of cyclohexane:ethyl acetate—100:0 to 75:25, the title compound as a beige solid (1.29 g, 92% yield). $^1$H NMR (300 MHz, CHCl$_3$-d) 7.55-7.42 (m, 3H), 7.38-7.23 (m, 6H), 7.17 (dd, J=1.4 and 8.0 Hz, 1H), 6.23 (d, J=7.9 Hz, 1H), 6.10 (d, J=7.9 Hz, 1H), 4.33 (bs, 2H).

Intermediate 6-8: tert-butyl N-[(1R)-1-[[6-(2-phenylphenoxy)-2-pyridyl]carbamoyl]propyl]carbamate

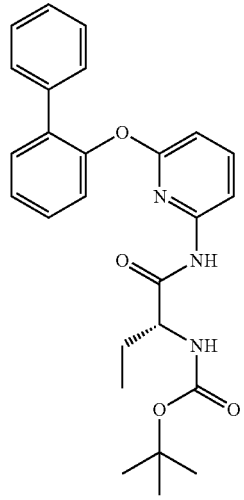 [SMILES: CC[C@@H](NC(=O)OC(C)(C)C)C(=O)Nc1cccc(Oc2ccccc2-c2ccccc2)n1]

Essentially following the procedures described for intermediate 6-2, using intermediate 6-7 (750 mg, 2.86 mmol) to afford, after purification by silica gel flash chromatography eluting with a gradient of cyclohexane:ethyl acetate—100:0 to 80:20, the title compound as a white foam (775 mg, 61% yield). $^1$H NMR (300 MHz, CHCl$_3$-d) 8.19 (bs, 1H), 7.92 (d, J=7.9 Hz, 1H), 7.89-7.82 (m, 2H), 7.81-7.74 (m, 1H), 7.14 (app. t, J=8.0 Hz, 1H), 7.55-7.41 (m, 3H), 7.30-7.23 (m, 2H), 6.52 (d, J=8.0 Hz, 1H), 5.03-4.82 (m, 1H), 4.25-4.03 (m, 1H), 2.03-1.87 (m, 1H), 1.75-1.56 (m, 1H), 1.58 (s, 1H), 1.38 (s, 9H), 0.96 (t, J=7.4 Hz, 3H).

Intermediate 6-9: (2R)-2-amino-N-[6-(2-phenylphenoxy)-2-pyridyl]butanamide

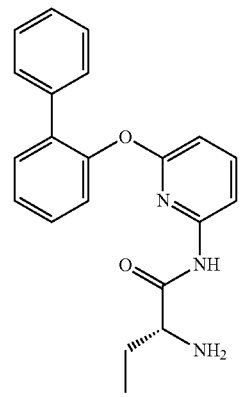 [SMILES: CC[C@@H](N)C(=O)Nc1cccc(Oc2ccccc2-c2ccccc2)n1]

Essentially following the procedures described for intermediate 6-6, using intermediate 6-8 (750 mg, 3.17 mmol) to afford, after evaporation under reduced pressure, the title compound as a colorless gum (530 mg, 88% yield). $^1$H NMR (300 MHz, DMSO-$d_6$) 7.81-7.62 (m, 2H), 7.50-7.30 (m, 8H), 7.14 (dd, J=1.3 and 8.0 Hz, 1H), 6.49 (dd, J=1.0 and 7.7 Hz, 1H), 3.28-3.18 (m, 1H), 1.70-1.52 (m, 1H), 1.49-1.30 (m, 1H), 0.84 (t, J=7.4 Hz, 3H).

Example 50: (5R)-5-ethyl-3-[6-(2-phenylphenoxy)-2-pyridyl]imidazolidine-2,4-dione Intermediate 6-11: tert-butyl N-[(1R)-1-[[6-(4-methoxy-3-methyl-phenoxy)-2-pyridyl]carbamoyl]propyl]carbamate

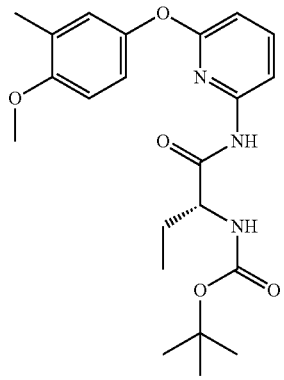

Essentially following the procedures described for intermediate 6-2, using intermediate 6-10 (275 mg, 1.19 mmol) to afford, after purification by silica gel flash chromatography eluting with a gradient of cyclohexane:ethyl acetate—100:0 to 60:40, the title compound as a colorless sticky solid (380 mg, 77% yield). ESIMS m/z [M+H]$^+$ 416.33

Intermediate 6-12: (2R)-2-amino-N-[6-(4-methoxy-3-methyl-phenoxy)-2-pyridyl]butanamide

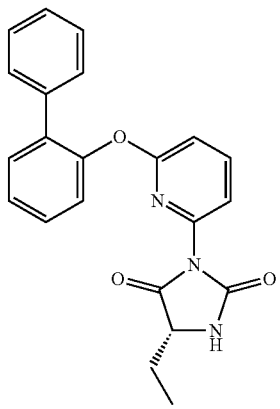 [SMILES: CC[C@H]1NC(=O)N(c2cccc(Oc3ccccc3-c3ccccc3)n2)C1=O]

Essentially following the procedures described for example 6-1, using intermediate 6-9 (530 mg, 1.52 mmol) to afford, after purification by silica gel flash chromatography eluting with a gradient of cyclohexane:ethyl acetate—100:0 to 50:50, the title compound as a colorless varnish (290 mg, 51% yield). $^1$H NMR (300 MHz, DMSO-d$_6$) 8.49 (bs, 1H), 7.91 (app. t, J=7.9 Hz, 1H), 7.49-7.23 (m, 8H), 7.18 (dd, J=1.1 and 8.0 Hz, 1H), 7.06 (d, J=7.5 Hz, 1H), 6.90 (d, J=8.2 Hz, 1H), 4.25-4.10 (m, 1H), 1.84-1.53 (m, 2H), 0.89 (t, J=7.4 Hz, 3H). ESIMS m/z [M+H]$^+$ 374.33

Synthesis of Example 51

Intermediate 6-10: 6-(4-methoxy-3-methyl-phenoxy)pyridin-2-amine

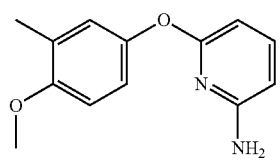 [SMILES: COc1ccc(Oc2cccc(N)n2)cc1C]

Essentially following the procedures described for intermediate 6-1, using 4-methoxy-3-methylphenol (200 mg, 1.45 mmol) to afford, after purification by silica gel flash chromatography eluting with a gradient of cyclohexane:ethyl acetate—100:0 to 50:50, the title compound as a white solid (280 mg, 83% yield). ESIMS m/z [M+H]$^+$ 231.25

Essentially following the procedures described for intermediate 6-6, using intermediate 6-11 (380 mg, 0.91 mmol) to afford, after evaporation under reduced pressure, the title compound as a yellow oil (265 mg, 92% yield). ESIMS m/z [M+H]$^+$ 316.33

Example 51: (5R)-5-ethyl-3-[6-(4-methoxy-3-methyl-phenoxy)-2-pyridyl]imidazolidine-2,4-dione

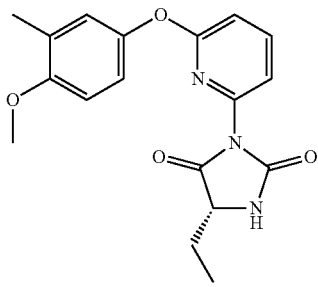 [SMILES: CC[C@H]1NC(=O)N(c2cccc(Oc3ccc(OC)c(C)c3)n2)C1=O]

Essentially following the procedures described for example 6-1, using intermediate 6-12 (265 mg, 0.84 mmol) to afford, after purification by silica gel flash chromatography eluting with a gradient of cyclohexane:ethyl acetate—100:0 to 30:70, the title compound as a colorless oil (230 mg, 81% yield). $^1$H NMR (300 MHz, DMSO-d$_6$) 8.51 (bs, 1H), 7.94 (app. t, J=8.0 Hz, 1H), 7.07 (d, J=7.5 Hz, 1H), 7.03-6.85 (m, 4H), 4.25-4.10 (m, 1H), 3.77 (s, 3H), 2.12 (s, 3H), 1.80-1.53 (m, 2H), 0.89 (t, J=7.4 Hz, 3H). ESIMS m/z [M+H]$^+$ 342.1

Synthesis of Example 52

Intermediate 6-13:
6-(5-methoxy-2-methyl-phenoxy)pyridin-2-amine

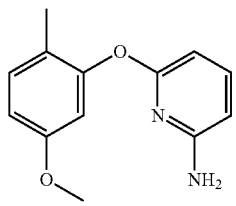 [SMILES: COc1ccc(C)c(Oc2cccc(N)n2)c1]

Essentially following the procedures described for intermediate 6-1, using 5-methoxy-2-methylphenol (500 mg, 3.62 mmol) to afford, after purification by silica gel flash chromatography eluting with a gradient of cyclohexane:ethyl acetate—100:0 to 50:50, the title compound as a yellow oil (530 mg, 64% yield). ESIMS m/z [M+H]$^+$ 231.17

Intermediate 6-14: tert-butyl N-[(1R)-1-[[6-(5-methoxy-2-methyl-phenoxy)-2-pyridyl]carbamoyl]propyl]carbamate

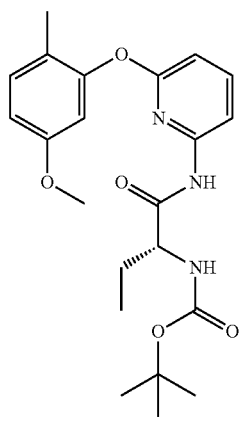 [SMILES: CC[C@@H](NC(=O)OC(C)(C)C)C(=O)Nc1cccc(Oc2cc(OC)ccc2C)n1]

Essentially following the procedures described for intermediate 6-2, using intermediate 6-13 (530 mg, 2.30 mmol) to afford, after purification by silica gel flash chromatography eluting with a gradient of cyclohexane:ethyl acetate—100:0 to 50:50, the title compound as a white foam (720 mg, 75% yield). ESIMS m/z [M+H]$^+$ 416.4

Intermediate 6-15: (2R)-2-amino-N-[6-(5-methoxy-2-methyl-phenoxy)-2-pyridyl]butanamide

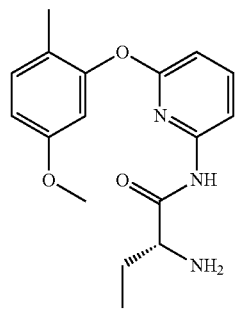 [SMILES: CC[C@@H](N)C(=O)Nc1cccc(Oc2cc(OC)ccc2C)n1]

Essentially following the procedures described for intermediate 6-6, using intermediate 6-14 (720 mg, 1.73 mmol) to afford, after evaporation under reduced pressure, the title compound as a yellow oil (490 mg, 89% yield). ESIMS m/z [M+H]$^+$ 316.33

Example 52: (5R)-5-ethyl-3-[6-(5-methoxy-2-methyl-phenoxy)-2-pyridyl]imidazolidine-2,4-dione

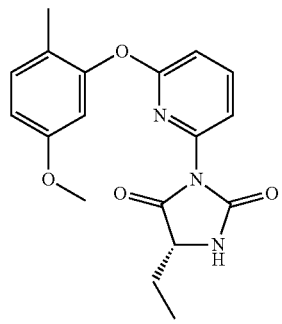 [SMILES: CC[C@H]1NC(=O)N(c2cccc(Oc3cc(OC)ccc3C)n2)C1=O]

Essentially following the procedures described for example 6-1, using intermediate 6-15 (490 mg, 1.55 mmol) to afford, after purification by silica gel flash chromatography eluting with a gradient of cyclohexane:ethyl acetate—100:0 to 0:100, the title compound as a white foam (220 mg, 41% yield). $^1$H NMR (300 MHz, DMSO-d$_6$) 8.49 (bs, 1H), 7.94 (app. t, J=7.9 Hz, 1H), 7.17 (d, J=8.2 Hz, 1H), 7.08 (d, J=7.4 Hz, 1H), 6.95 (d, J=8.2 Hz, 1H), 6.75-6.65 (m, 2H), 4.22-4.13 (m, 1H), 3.69 (s, 3H), 2.00 (s, 3H), 1.84-1.55 (m, 2H), 0.88 (t, J=7.4 Hz, 3H). ESIMS m/z [M+H]$^+$ 342.1

Synthesis of Example 53

Intermediate 6-16:
6-(4-methoxy-phenoxy)pyridin-2-amine

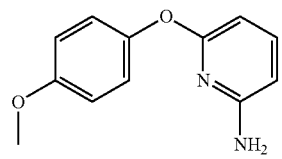 [SMILES: COc1ccc(Oc2cccc(N)n2)cc1]

Essentially following the procedures described for intermediate 6-1, using 4-methoxyphenol (1.0 g, 8.06 mmol) to afford, after purification by silica gel flash chromatography eluting with a gradient of cyclohexane:ethyl acetate—100:0 to 50:50, the title compound as a white solid (1.37 g, 79% yield). ESIMS m/z [M+H]+ 216.9

Intermediate 6-17: tert-butyl N-[(1R)-1-[[6-(4-methoxy-phenoxy)-2-pyridyl]carbamoyl]propyl]carbamate

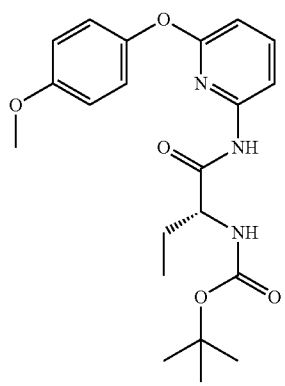 [SMILES: CC[C@@H](NC(=O)OC(C)(C)C)C(=O)Nc1cccc(Oc2ccc(OC)cc2)n1]

Essentially following the procedures described for intermediate 6-2, using intermediate 6-16 (1.37 g, 6.33 mmol) to afford, after purification by silica gel flash chromatography eluting with a gradient of cyclohexane:ethyl acetate—100:0 to 50:50, the title compound as a colorless sticky solid (1.76 g, 69% yield). ESIMS m/z [M+H]+ 402.42

Intermediate 6-18: (2R)-2-amino-N-[6-(4-methoxy-phenoxy)-2-pyridyl]butanamide

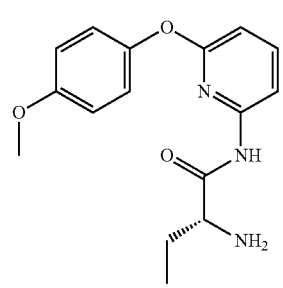 [SMILES: CC[C@@H](N)C(=O)Nc1cccc(Oc2ccc(OC)cc2)n1]

Essentially following the procedures described for intermediate 6-6, using intermediate 6-17 (1.76 g, 7.39 mmol) to afford, after evaporation under reduced pressure, the title compound as a yellow oil (820 mg, 62% yield). ESIMS m/z [M+H]+ 302.33

Example 53: (5R)-5-ethyl-3-[6-(4-methoxy-phenoxy)-2-pyridyl]imidazolidine-2,4-dione

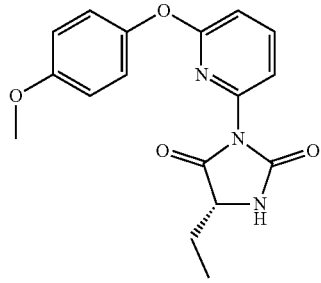 [SMILES: CC[C@H]1NC(=O)N(c2cccc(Oc3ccc(OC)cc3)n2)C1=O]

Essentially following the procedures described for example 6-1, using intermediate 6-18 (815 mg, 2.71 mmol) to afford, after purification by silica gel flash chromatography eluting with a gradient of cyclohexane:ethyl acetate—100:0 to 40:60, the title compound as a white foam (310 mg, 35% yield). 1H NMR (300 MHz, DMSO-d6) 8.50 (bs, 1H), 7.95 (app. t, J=8.0 Hz, 1H), 7.15-7.04 (m, 3H), 7.03-6.85 (m, 3H), 4.22-4.12 (m, 1H), 3.74 (s, 3H), 1.80-1.55 (m, 2H), 0.89 (t, J=7.4 Hz, 3H). ESIMS m/z [M+H]+ 328.0

Synthesis of Example 54

Intermediate 6-19: 6-(5-methoxy-3-methyl-phenoxy)pyridin-2-amine

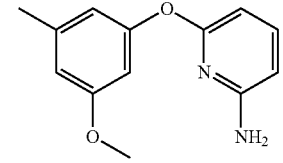 [SMILES: COc1cc(C)cc(Oc2cccc(N)n2)c1]

Essentially following the procedures described for intermediate 6-1, using 5-methoxy-3-methylphenol (500 mg, 3.62 mmol) to afford, after purification by silica gel flash chromatography eluting with a gradient of cyclohexane:ethyl acetate—100:0 to 50:50, the title compound as a yellow oil (520 mg, 62% yield). ESIMS m/z [M+H]+ 231.0

Intermediate 6-20: tert-butyl N-[(1R)-1-[[6-(5-methoxy-3-methyl-phenoxy)-2-pyridyl]carbamoyl]propyl]carbamate

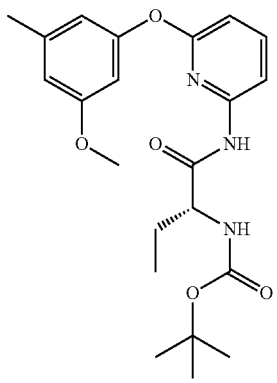 [SMILES: CC[C@@H](NC(=O)OC(C)(C)C)C(=O)Nc1cccc(Oc2cc(C)cc(OC)c2)n1]

Essentially following the procedures described for intermediate 6-2, using intermediate 6-19 (520 mg, 2.24 mmol) to afford, after purification by silica gel flash chromatography eluting with a gradient of cyclohexane:ethyl acetate—100:0 to 50:50, the title compound as a white foam (800 mg, 86% yield). ESIMS m/z [M+H]$^+$ 416.1

Intermediate 6-21: (2R)-2-amino-N-[6-(5-methoxy-3-methyl-phenoxy)-2-pyridyl]butanamide

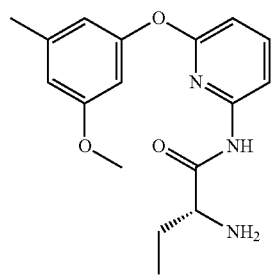 [SMILES: CC[C@@H](N)C(=O)Nc1cccc(Oc2cc(C)cc(OC)c2)n1]

Essentially following the procedures described for intermediate 6-6, using intermediate 6-20 (800 mg, 1.93 mmol) to afford, after evaporation under reduced pressure, the title compound as a yellow oil (570 mg, 94% yield). ESIMS m/z [M+H]$^+$ 316.1

Example 54: (5R)-5-ethyl-3-[6-(5-methoxy-3-methyl-phenoxy)-2-pyridyl]imidazolidine-2,4-dione

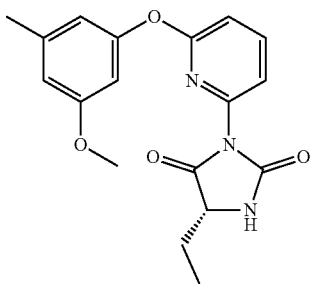 [SMILES: CC[C@H]1NC(=O)N(c2cccc(Oc3cc(C)cc(OC)c3)n2)C1=O]

Essentially following the procedures described for example 6-1, using intermediate 6-21 (570 mg, 1.80 mmol) to afford, after purification by silica gel flash chromatography eluting with a gradient of cyclohexane:ethyl acetate—100:0 to 0:100, the title compound as a white foam (244 mg, 39% yield). $^1$H NMR (300 MHz, DMSO-d$_6$) 8.54 (bs, 1H), 7.98 (app. t, J=7.9 Hz, 1H), 7.12 (d, J=7.5 Hz, 1H), 6.98 (d, J=8.2 Hz, 1H), 6.62-6.48 (m, 3H), 4.22-4.15 (m, 1H), 3.70 (s, 3H), 2.24 (s, 3H), 1.84-1.55 (m, 2H), 0.90 (t, J=7.4 Hz, 3H). ESIMS m/z [M+H]$^+$ 342.33

Synthesis of Example 55

Intermediate 6-22: 6-(3-methoxy-phenoxy)pyridin-2-amine

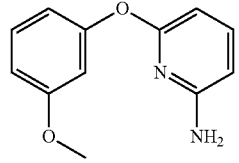 [SMILES: COc1cccc(Oc2cccc(N)n2)c1]

Essentially following the procedures described for intermediate 6-1, using 3-methoxyphenol (1.0 g, 8.06 mmol) to afford, after purification by silica gel flash chromatography eluting with a gradient of cyclohexane:ethyl acetate—100:0 to 40:60, the title compound as a colorless oil (1.24 g, 71% yield). ESIMS m/z [M+H]$^+$ 216.9

Intermediate 6-23: tert-butyl N-[(1R)-1-[[6-(3-methoxy-phenoxy)-2-pyridyl]carbamoyl]propyl]carbamate

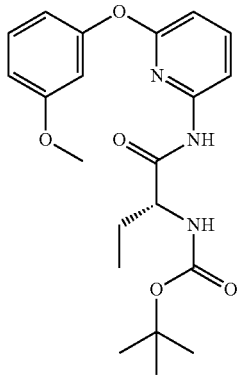 [SMILES: CC[C@@H](NC(=O)OC(C)(C)C)C(=O)Nc1cccc(Oc2cccc(OC)c2)n1]

Essentially following the procedures described for intermediate 6-2, using intermediate 6-22 (1.24 g, 5.73 mmol) to afford, after purification by silica gel flash chromatography eluting with a gradient of cyclohexane:ethyl acetate—100:0 to 60:40, the title compound as a colorless foam (1.32 g, 51% yield). ESIMS m/z [M+H]$^+$ 402.4

Intermediate 6-24: (2R)-2-amino-N-[6-(3-methoxy-phenoxy)-2-pyridyl]butanamide

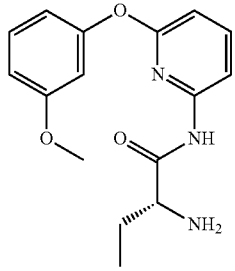 [SMILES: CC[C@@H](N)C(=O)Nc1cccc(Oc2cccc(OC)c2)n1]

Essentially following the procedures described for intermediate 6-6, using intermediate 6-23 (1.32 g, 2.94 mmol) to afford, after evaporation under reduced pressure, the title compound as a yellow oil (860 mg, 85% yield). ESIMS m/z [M+H]$^+$ 302.25

Example 55: (5R)-5-ethyl-3-[6-(3-methoxy-phenoxy)-2-pyridyl]imidazolidine-2,4-dione

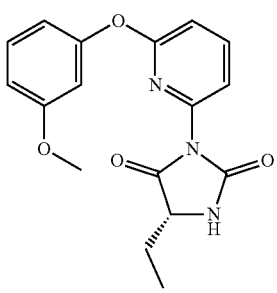 [SMILES: CC[C@H]1NC(=O)N(c2cccc(Oc3cccc(OC)c3)n2)C1=O]

Essentially following the procedures described for example 6-1, using intermediate 6-24 (570 mg, 1.80 mmol) to afford, after purification by silica gel flash chromatography eluting with a gradient of cyclohexane:ethyl acetate—100:0 to 40:60, the title compound as a colorless sticky oil (310 mg, 32% yield). $^1$H NMR (300 MHz, DMSO-d$_6$) 8.53 (bs, 1H), 7.99 (app. t, J=7.9 Hz, 1H), 7.29 (t, J=7.9 Hz, 1H), 7.13 (d, J=7.5 Hz, 1H), 7.01 (d, J=8.2 Hz, 1H), 6.80-6.68 (m, 3H), 4.22-4.15 (m, 1H), 3.73 (s, 3H), 1.84-1.55 (m, 2H), 0.89 (t, J=7.4 Hz, 3H). ESIMS m/z [M+H]$^+$ 328.25

Synthesis of Example 56

Intermediate 6-25: 2-methoxy-3-methyl-benzaldehyde and 2,3-dimethoxy-benzaldehyde

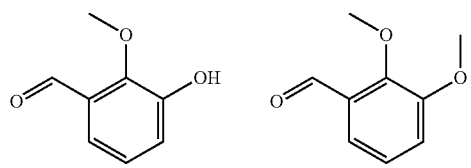

To a stirred solution of 2,3-dihydroxybenzaldehyde (2.0 g, 14.48 mmol) in DMF (25 mL) was added potassium carbonate (2.2 g, 15.90 mmol). The mixture was stirred 30 minutes at room temperature and iodomethane (1.0 mL, 15.90 mmol) was added dropwise. The resulting solution was stirred at room temperature for 18 h. The mixture was hydrolyzed with a saturated aqueous solution of NH$_4$Cl, extracted using ethyl acetate, the organics were washed with brine, dried over MgSO$_4$ and concentrated in vacuo before purification by silica gel flash chromatography eluting with a gradient of cyclohexane:ethyl acetate—100:0 to 75:25 to give as the first eluting compound 2,3-dimethoxy-benzaldehyde as a colorless gum (450 mg, 19% yield) and as the last eluting compound 2-methoxy-3-methyl-benzaldehyde as a white solid (1.27 g, 57% yield). 2,3-dimethoxy-benzaldehyde: $^1$H NMR (300 MHz, CHCl$_3$-d) 10.43 (s, 1H), 7.45-7.38 (m, 1H), 7.18-7.10 (m, 2H), 3.98 (s, 3H), 3.91 (s, 3H). 2-methoxy-3-methyl-benzaldehyde: $^1$H NMR (300 MHz, CHCl$_3$-d) 10.26 (s, 1H), 7.45-7.38 (dd, J=1.8 and 7.6 Hz, 1H), 7.26-7.10 (m, 2H), 5.79 (s, 1H), 3.97 (s, 3H).

Intermediate 6-26: 2-methoxy-3-methyl-phenol

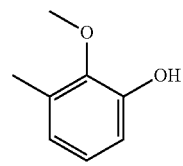

Essentially following the procedures described for intermediate 1-1, using 2-methoxy-3-methylbenzaldehyde (1.27 g, 8.34 mmol) to afford, after purification by silica gel flash chromatography eluting with a gradient of cyclohexane: ethyl acetate—100:0 to 80:20, the title compound as a colorless oil (975 mg, 84% yield). $^1$H NMR (300 MHz, CHCl$_3$-d) 6.91 (app. t, J=7.8 Hz, 1H), 6.80 (dd, J=1.6 and 8.0 Hz, 1H), 6.69 (dd, J=0.7 and 7.5 Hz, 1H), 5.62 (bs, 1H), 3.80 (s, 3H), 2.30 (s, 3H).

Intermediate 6-27: 6-(2-methoxy-3-methyl-phenoxy)pyridin-2-amine

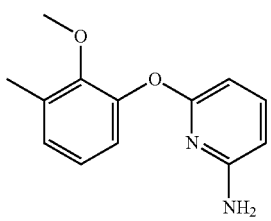 [SMILES: COc1c(C)cccc1Oc1cccc(N)n1]

Essentially following the procedures described for intermediate 6-1, using intermediate 6-26 (210 mg, 1.52 mmol) to afford, after purification by silica gel flash chromatography eluting with a gradient of cyclohexane:ethyl acetate—100:0 to 50:50, the title compound as a white solid (160 mg, 47% yield). ESIMS m/z [M+H]$^+$ 231.0

Intermediate 6-28: methyl (2R)-2-(tert-butoxycarbonylamino)butanoate

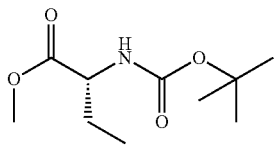

To a stirred solution of Boc-D-Abu-OH (4.0 g, 19.68 mmol) and potassium carbonate (9.52 g, 68.88 mmol) in DMF (25 mL) at room temperature was added Iodomethane (2.45 mL, 39.36 mmol). After addition, the mixture was stirred at room temperature for 24 h. The resulting mixture was diluted with water (20 mL), extracted with ethyl acetate (3×25 mL), the combined organic extracts were washed with saturated aqueous sodium chloride (15 mL), dried over magnesium sulfate, filtered, and concentrated under reduced pressure. The residue was purified by silica gel flash chromatography eluting with a gradient of cyclohexane:ethyl acetate—100:0 to 75:25, to give the title compound as a colorless liquid (4.30 g, 100% yield). $^1$H NMR (300 MHz, CHCl$_3$-d) 5.10-4.95 (m, 1H), 4.32-4.16 (m, 1H), 3.72 (s, 3H), 1.95-1.75 (m, 1H), 1.75-1.58 (m, 1H), 1.43 (s, 9H), 0.91 (t, J=7.4 Hz, 3H).

Intermediate 6-29: tert-butyl N-[(1R)-1-[[6-(2-methoxy-3-methyl-phenoxy)-2-pyridyl]carbamoyl]propyl]carbamate

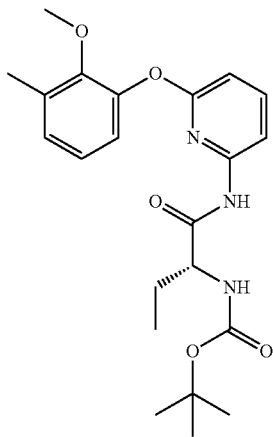 [SMILES: CC[C@@H](NC(=O)OC(C)(C)C)C(=O)Nc1cccc(Oc2cccc(C)c2OC)n1]

In a sealable vessel, intermediate 6-27 (134 mg, 0.58 mmol) was dissolved into DCM (5 mL). Trimethylaluminum, 2.0M solution in toluene (0.87 mL, 1.75 mmol) was slowly added and the reaction mixture was stirred at room temperature for 45 minutes. Intermediate 6-28 (126 mg, 0.58 mmol) was added, the vessel was sealed and the reaction mixture was stirred at room temperature for 18 hours and heated at 50° C. for 5 hours. The reaction was quenched with water, DCM was added and the 2 phases were filtered through celite to remove the aluminum salts. The filtrate was extracted twice with DCM. The combined organic extracts were dried over magnesium sulfate, filtered, and concentrated under reduced pressure. The residue was purified by silica gel flash chromatography eluting with a gradient of cyclohexane:ethyl acetate—100:0 to 70:30, to give the title compound as a colorless oil (100 mg, 42% yield). ESIMS m/z [M+H]$^+$ 416.1

Intermediate 6-30: (2R)-2-amino-N-[6-(2-methoxy-3-methyl-phenoxy)-2-pyridyl]butanamide

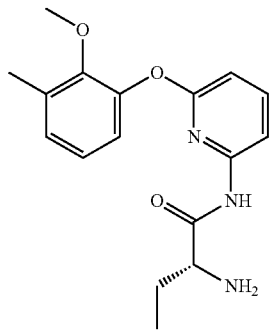 [SMILES: CC[C@@H](N)C(=O)Nc1cccc(Oc2cccc(C)c2OC)n1]

Essentially following the procedures described for intermediate 6-6, using intermediate 6-29 (100 mg, 0.24 mmol) to afford, after evaporation under reduced pressure, the title compound as a yellow oil (59 mg, 78% yield). ESIMS m/z [M+H]$^+$ 316.3

Example 56: (5R)-5-ethyl-3-[6-(2-methoxy-3-methyl-phenoxy)-2-pyridyl]imidazolidine-2,4-dione

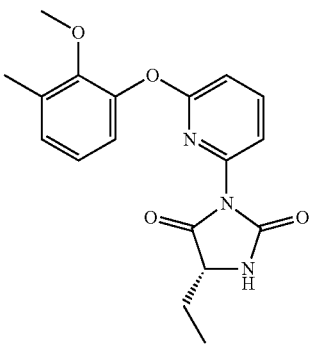 [SMILES: CC[C@H]1NC(=O)N(c2cccc(Oc3cccc(C)c3OC)n2)C1=O]

Essentially following the procedures described for example 6-1, using intermediate 6-30 (59 mg, 0.19 mmol) to afford, after purification by silica gel flash chromatography eluting with a gradient of cyclohexane:ethyl acetate—100:0 to 30:70 and semi-preparative HPLC, the title compound as a colorless oil (23 mg, 36% yield). $^1$H NMR (300 MHz, DMSO-d$_6$) 8.50 (bs, 1H), 7.96 (app. t, J=7.8 Hz, 1H), 7.12-6.96 (m, 4H), 6.93 (d, J=8.0 Hz, 1H), 4.21-4.13 (m, 1H), 3.61 (s, 3H), 2.22 (s, 3H), 1.81-1.56 (m, 2H), 0.88 (t, J=7.4 Hz, 3H). ESIMS m/z [M+H]$^+$ 342.33

Synthesis of Example 57

Intermediate 6-31: 4-[(6-bromo-2-pyridyl)oxy]-3-tert-butyl-benzonitrile

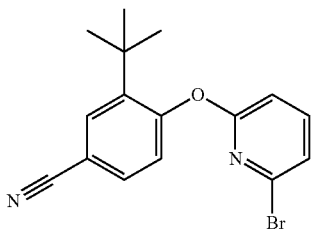 [SMILES: CC(C)(C)c1cc(C#N)ccc1Oc1cccc(Br)n1]

To a solution of 3-(tert-Butyl)-4-hydroxybenzonitrile (290 mg, 1.65 mmol) in DMSO (3 mL) was added potassium tert-butoxide (190 mg, 1.69 mmol) and 2,6-dibromopyridine (400 mg, 1.69 mmol). The reaction mixture was stirred at 160° C. for 4 h. After cooling down to RT, water was added (precipitation). The solid formed was filtered off, washed with water and purified by silica gel flash chromatography eluting with a gradient of cyclohexane:dichloromethane—100:0 to 0:100, to give the title compound as a white solid (355 mg, 65% yield). $^1$H NMR (300 MHz, DMSO-$d_6$) 7.87 (app. t, J=7.8 Hz, 1H), 7.83 (d, J=2.0 Hz, 1H), 7.75 (dd, J=2.0 and 8.4 Hz, 1H), 7.46 (d, J=7.6 Hz, 1H), 7.27-7.12 (m, 2H), 1.33 (s, 9H).

Example 57: 3-tert-butyl-4-[[6-[(4R)-4-ethyl-2,5-dioxo-imidazolidin-1-yl]-2-pyridyl]oxy]benzonitrile

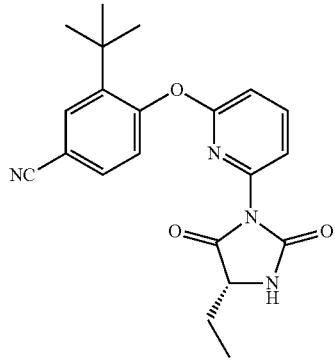 [SMILES: CC[C@H]1NC(=O)N(c2cccc(Oc3ccc(C#N)cc3C(C)(C)C)n2)C1=O]

Essentially following the procedures described for example 2, using intermediate 6-31 (400 mg, 1.21 mmol) and intermediate 2-8 (170 mg, 1.33 mmol) to afford, after purification by silica gel flash chromatography eluting with a gradient of cyclohexane:dichloromethane—100:0 to 0:100 and dichloromethane:ethyl acetate—100:0 to 0:100, semi-preparative HPLC and lyophilization using water and acetonitrile, the title compound as a white solid (61 mg, 13% yield). $^1$H NMR (300 MHz, DMSO-$d_6$) 8.53 (bs, 1H), 8.08 (app. t, J=7.9 Hz, 1H), 7.80 (d, J=2.0 Hz, 1H), 7.70 (dd, J=2.0 and 8.4 Hz, 1H), 7.25-7.14 (m, 3H), 4.23-4.14 (m, 1H), 1.88-1.55 (m, 2H), 1.34 (s, 9H), 0.89 (t, J=7.4 Hz, 3H). ESIMS m/z [M+H]$^+$ 379.33.

Synthesis of Example 58

Intermediate 6-32: 2-bromo-6-(3-methoxy-4-methyl-phenoxy)pyridine

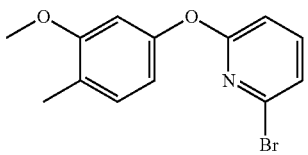 [SMILES: COc1cc(Oc2cccc(Br)n2)ccc1C]

Essentially following the procedures described for intermediate 6-31, using intermediate 1-1 (120 mg, 0.87 mmol) to afford, after purification by silica gel flash chromatography eluting with a gradient of cyclohexane:dichloromethane—100:0 to 50:50, the title compound as a colorless oil (185 mg, 72% yield). $^1$H NMR (300 MHz, CDCl$_3$-d) 7.49 (dd, J=7.6 and 8.1 Hz, 1H), 7.18 (d, J=7.6 Hz, 1H), 7.12 (d, J=8.1 Hz, 1H), 6.72 (d, J=8.1 Hz, 1H), 6.70-6.58 (m, 2H), 3.80 (s, 3H), 2.21 (s, 3H).

Example 58: (5R)-5-ethyl-3-[6-(3-methoxy-4-methyl-phenoxy)-2-pyridyl]-5-methyl-imidazolidine-2,4-dione

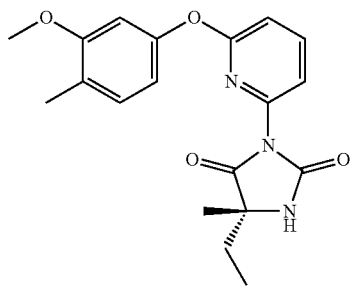 [SMILES: CC[C@@]1(C)NC(=O)N(c2cccc(Oc3ccc(C)c(OC)c3)n2)C1=O]

Essentially following the procedures described for example 2, using intermediate 6-32 (180 mg, 0.61 mmol) and intermediate 2-1 (90 mg, 0.63 mmol) to afford, after purification by silica gel flash chromatography eluting with a gradient of cyclohexane:dichloromethane—100:0 to 0:100 and dichloromethane:ethyl acetate—100:0 to 0:100 and lyophilization using water and acetonitrile, the title compound as a white foam (83 mg, 38% yield). 1H NMR (300 MHz, DMSO-$d_6$) 8.52 (bs, 1H), 7.99 (dd, J=7.8 and 8.0 Hz, 1H), 7.14 (d, J=7.6 Hz, 1H), 6.97 (d, J=8.2 Hz, 1H), 6.84 (d, J=2.1 Hz, 1H), 6.65 (dd, J=2.1 and 8.0 Hz, 1H), 3.76 (s, 3H), 2.13 (s, 3H), 1.85-1.55 (m, 2H), 1.35 (s, 3H), 0.82 (t, J=7.4 Hz, 3H). ESIMS m/z [M+H]$^+$ 356.0.

Synthesis of Example 59

Intermediate 6-33: 2-bromo-6-(4-fluoro-3-methoxy-phenoxy)pyridine

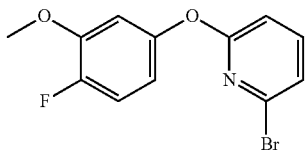 [SMILES: COc1cc(Oc2cccc(Br)n2)ccc1F]

Essentially following the procedures described for intermediate 6-31, using 4-fluoro-3-methoxyphenol (115 mg, 0.81 mmol) to afford without purification the title compound as a brown solid (215 mg, 74% yield). ESIMS m/z [M+H]$^+$ 300.17.

Example 59: (5R)-5-ethyl-3-[6-(4-fluoro-3-methoxy-phenoxy)-2-pyridyl]-5-methyl-imidazolidine-2,4-dione

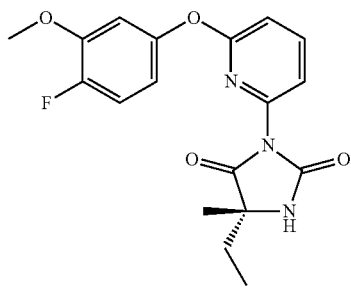 [SMILES: CC[C@@]1(C)NC(=O)N(c2cccc(Oc3ccc(F)c(OC)c3)n2)C1=O]

Essentially following the procedures described for example 2, using intermediate 6-33 (205 mg, 0.57 mmol) and intermediate 2-1 (110 mg, 0.67 mmol) to afford, after two purifications by silica gel flash chromatography eluting for the first one with a gradient of dichloromethane:ethyl acetate—100:0 to 50:50 and for the second one with a gradient of cyclohexane:ethyl acetate—100:0 to 0:100 and lyophilization using water and methanol, the title compound as a white solid (125 mg, 59% yield). $^1$H NMR (300 MHz, DMSO-d$_6$) 8.52 (bs, 1H), 8.01 (dd, J=7.7 and 8.1 Hz, 1H), 7.24 (dd, J=8.8 and 11.3 Hz, 1H), 7.16 (d, J=7.1 Hz, 1H), 7.09 (dd, J=2.8 and 7.5 Hz, 1H), 7.02 (d, J=8.1 Hz, 1H), 6.80-6.69 (m, 1H), 3.82 (s, 3H), 1.80-1.55 (m, 2H), 1.35 (s, 3H), 0.81 (t, J=7.4 Hz, 3H). ESIMS m/z [M+H]$^+$ 360.33

Synthesis of Example 60

Intermediate 6-34: 2-bromo-6-(4-fluoro-3-methyl-phenoxy)pyridine

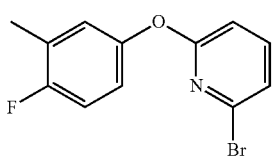 [SMILES: Cc1cc(Oc2cccc(Br)n2)ccc1F]

Essentially following the procedures described for intermediate 6-31, using 4-fluoro-3-methylphenol (105 mg, 0.83 mmol) to afford without purification the title compound as a brown oil (245 mg, 79% yield). ESIMS m/z [M+H]$^+$ 284.08.

Example 60: (5R)-5-ethyl-3-[6-(4-fluoro-3-methyl-phenoxy)-2-pyridyl]-5-methyl-imidazolidine-2,4-dione

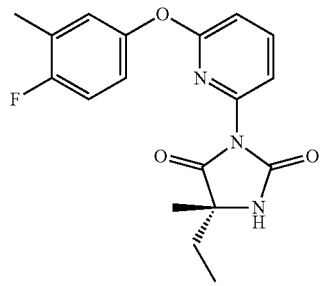 [SMILES: CC[C@@]1(C)NC(=O)N(c2cccc(Oc3ccc(F)c(C)c3)n2)C1=O]

Essentially following the procedures described for example 2, using intermediate 6-34 (235 mg, 0.63 mmol) and intermediate 2-1 (110 mg, 0.67 mmol) to afford, after purification by silica gel flash chromatography eluting with a gradient of dichloromethane:ethyl acetate—100:0 to 0:100, the title compound as an off-white solid (114 mg, 51% yield). $^1$H NMR (300 MHz, DMSO-d$_6$) 8.51 (bs, 1H), 8.01 (app. t, J=7.9 Hz, 1H), 7.31 (app. t, J=8.7 Hz, 1H), 7.18 (d, J=7.5 Hz, 1H), 7.11 (dd, J=2.3 and 11.0 Hz, 1H), 7.05 (d, J=8.1 Hz, 1H), 6.95 (dd, J=2.3 and 8.3 Hz, 1H), 2.22 (s, 3H), 1.82-1.53 (m, 2H), 1.35 (s, 3H), 0.81 (t, J=7.4 Hz, 3H). ESIMS m/z [M+H]$^+$ 344.33

Synthesis of Example 61

Intermediate 6-35: 2-bromo-6-indan-5-yloxy-pyridine

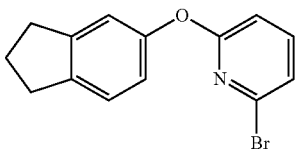 [SMILES: Brc1cccc(Oc2ccc3c(c2)CCC3)n1]

Essentially following the procedures described for intermediate 6-31, using 5-hydroxyindan (300 mg, 2.24 mmol) to afford, after purification by silica gel flash chromatography eluting with a gradient of cyclohexane:dichloromethane—100:0 to 0:100, the title compound as a colorless oil (500 mg, 77% yield).). $^1$H NMR (300 MHz, CDCl$_3$-d) 7.47 (dd, J=7.7 and 7.9 Hz, 1H), 7.24-7.10 (m, 2H), 6.97 (s, 1H), 6.88 (dd, J=2.2 and 8.1 Hz, 1H), 6.70 (d, J=8.1 Hz, 1H), 3.03-2.81 (m, 4H), 2.19-2.05 (m, 2H).

Example 61: (5R)-5-ethyl-3-(6-indan-5-yloxy-2-pyridyl)-5-methyl-imidazolidine-2,4-dione

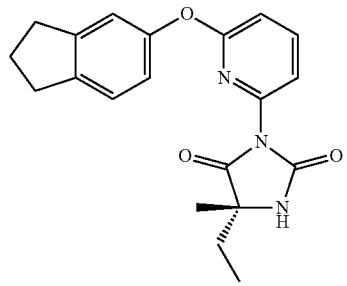 [SMILES: CC[C@@]1(C)NC(=O)N(c2cccc(Oc3ccc4c(c3)CCC4)n2)C1=O]

Essentially following the procedures described for example 2, using intermediate 6-35 (250 mg, 0.86 mmol) and intermediate 2-1 (122 mg, 0.86 mmol) to afford, after purification by silica gel flash chromatography eluting with a gradient of cyclohexane:ethyl acetate—100:0 to 0:100, the title compound as a white solid (164 mg, 53% yield). $^1$H NMR (300 MHz, DMSO-$d_6$) 8.48 (bs, 1H), 8.01 (dd, J=7.8 and 8.0 Hz, 1H), 7.22 (d, J=8.1 Hz, 1H), 7.10 (d, J=7.5 Hz, 1H), 7.04 (d, J=1.7 Hz, 1H), 6.90 (d, J=8.2 Hz, 2H), 2.82 (t, J=7.4 Hz, 4H), 2.02 (quint, J=7.4 Hz, 2H), 1.80-1.55 (m, 2H), 1.33 (s, 3H), 0.80 (t, J=7.4 Hz, 3H). ESIMS m/z [M+H]$^+$ 352.33

Synthesis of Example 62

Intermediate 6-36: 2-bromo-6-(4-chloro-3-methoxy-phenoxy)pyridine

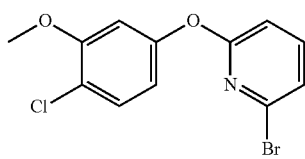 [SMILES: COc1cc(Oc2cccc(Br)n2)ccc1Cl]

Essentially following the procedures described for intermediate 6-31, using 4-chloro-3-methoxyphenol (300 mg, 1.89 mmol) to afford, after purification by silica gel flash chromatography eluting with a gradient of cyclohexane: dichloromethane—100:0 to 50:50, the title compound as a colorless oil (426 mg, 72% yield).). $^1$H NMR (300 MHz, CDCl$_3$-d) 7.53 (dd, J=7.6 and 8.0 Hz, 1H), 7.35 (d, J=8.6 Hz, 1H), 7.23 (d, J=7.6 Hz, 1H), 6.84-6.75 (m, 2H), 6.69 (dd, J=2.6 and 8.6 Hz, 1H), 3.88 (s, 3H).

Example 62: (5R)-3-[6-(4-chloro-3-methoxy-phenoxy)-2-pyridyl]-5-ethyl-5-methyl-imidazolidine-2,4-dione

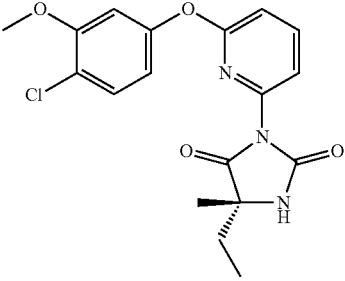 [SMILES: CC[C@@]1(C)NC(=O)N(c2cccc(Oc3ccc(Cl)c(OC)c3)n2)C1=O]

Essentially following the procedures described for example 2, using intermediate 6-36 (200 mg, 0.64 mmol) and intermediate 2-1 (90 mg, 0.64 mmol) in toluene to afford, after purification by silica gel flash chromatography eluting with a gradient of dihchloromethane:ethyl acetate—100:0 to 0:100 and lyophilization using water and acetonitrile, the title compound as a white foam (58 mg, 24% yield). $^1$H NMR (300 MHz, DMSO-$d_6$) 8.51 (bs, 1H), 8.01 (dd, J=7.8 and 8.0 Hz, 1H), 7.41 (d, J=8.6 Hz, 1H), 7.17 (d, J=7.5 Hz, 1H), 7.09-7.03 (m, 2H), 6.76 (dd, J=2.6 and 8.6 Hz, 1H), 3.82 (s, 3H), 1.78-1.54 (m, 2H), 1.33 (s, 3H), 0.79 (t, J=7.4 Hz, 3H). ESIMS m/z [M+H]$^+$ 376.33

Synthesis of Example 63

Intermediate 6-37: 2-(benzofuran-6-yloxy)-6-bromo-pyridine

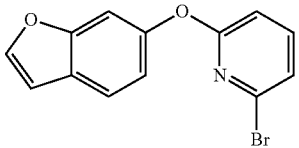 [SMILES: Brc1cccc(Oc2ccc3ccoc3c2)n1]

Essentially following the procedures described for intermediate 6-31, using benzofuran-6-ol (143 mg, 1.07 mmol) to afford, after purification by silica gel flash chromatography eluting with a gradient of cyclohexane:dichloromethane—100:0 to 0:100, the title compound as a colorless oil (266 mg, 87% yield).). $^1$H NMR (300 MHz, CDCl$_3$-d) 7.64 (d, J=2.2 Hz, 1H), 7.58 (d, J=8.4 Hz, 1H), 7.50 (dd, J=7.6 and 8.1 Hz, 1H), 7.32 (d, J=1.6 Hz, 1H), 7.19 (d, J=7.6 Hz, 1H), 7.05 (dd, J=2.1 and 8.4 Hz, 1H), 6.81-6.74 (m, 2H).

Example 63: (5R)-3-[6-(benzofuran-6-yloxy)-2-pyridyl]-5-ethyl-5-methyl-imidazolidine-2,4-dione

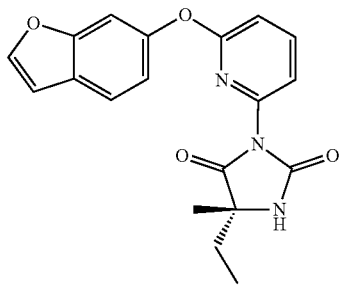 [SMILES: CC[C@@]1(C)NC(=O)N(c2cccc(Oc3ccc4ccoc4c3)n2)C1=O]

Essentially following the procedures described for example 2, using intermediate 6-37 (260 mg, 0.90 mmol) and intermediate 2-1 (127 mg, 0.90 mmol) to afford, after purification by silica gel flash chromatography eluting with a gradient of cyclohexane:ethyl acetate—100:0 to 0:100, the title compound as a white foam (180 mg, 57% yield). $^1$H NMR (300 MHz, DMSO-$d_6$) 8.48 (bs, 1H), 8.02-7.93 (m, 2H), 7.65 (d, J=8.4 Hz, 1H), 7.52 (d, J=1.6 Hz, 1H), 7.15 (d, J=7.5 Hz, 1H), 7.09 (dd, J=2.0 and 8.4 Hz, 1H), 7.02-6.93 (m, 2H), 1.78-1.52 (m, 2H), 1.32 (s, 3H), 0.77 (t, J=7.4 Hz, 3H). ESIMS m/z [M+H]$^+$ 352.25

Synthesis of Example 64

Intermediate 6-38: 2-bromo-6-chroman-7-yloxy-pyridine

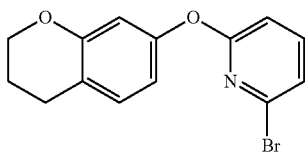 [SMILES: Brc1cccc(Oc2ccc3c(c2)OCCC3)n1]

Essentially following the procedures described for intermediate 6-31, using chroman-7-ol (160 mg, 1.07 mmol) to afford, after purification by silica gel flash chromatography eluting with a gradient of cyclohexane:dichloromethane—100:0 to 0:100, the title compound as a colorless oil (82 mg, 25% yield).). $^1$H NMR (300 MHz, CDCl$_3$-d) 7.47 (dd, J=7.8 and 7.9 Hz, 1H), 7.17 (dd, J=0.4 and 7.5 Hz, 1H), 7.02 (d, J=8.2 Hz, 1H), 6.73 (dd, J=0.6 and 8.2 Hz, 1H), 6.61 (dd, J=2.4 and 8.2 Hz, 1H), 6.57 (d, J=2.4 Hz, 1H), 4.18 (t, J=5.3 Hz, 2H), 2.77 (t, J=6.5 Hz, 2H), 2.06-1.95 (m, 2H).

Example 64: (5R)-3-(6-chroman-7-yloxy-2-pyridyl)-5-ethyl-5-methyl-imidazolidine-2,4-dione

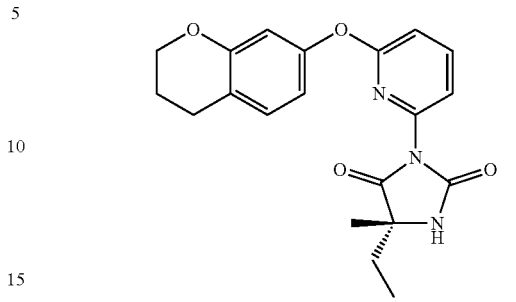

Essentially following the procedures described for example 2, using intermediate 6-38 (82 mg, 0.27 mmol) and intermediate 2-1 (38 mg, 0.27 mmol) to afford, after purification by silica gel flash chromatography eluting with a gradient of cyclohexane:ethyl acetate—100:0 to 0:100, the title compound as a white solid (38 mg, 39% yield). $^1$H NMR (300 MHz, DMSO-$d_6$) 8.49 (bs, 1H), 7.96 (dd, J=7.7 and 8.1 Hz, 1H), 7.11 (d, J=7.5 Hz, 1H), 7.06 (d, J=8.3 Hz, 1H), 6.61 (dd, J=2.4 and 8.3 Hz, 1H), 6.53 (d, J=2.4 Hz, 1H), 4.11 (t, J=5.1 Hz, 2H), 2.70 (t, J=6.3 Hz, 2H), 2.00-1.85 (m, 2H), 1.78-1.52 (m, 2H), 1.34 (s, 3H), 0.81 (t, J=7.4 Hz, 3H). ESIMS m/z [M+H]$^+$ 368.33

Synthesis of Example 65

Intermediate 6-39: 2-bromo-6-(3,4-dimethylphenoxy)pyridine

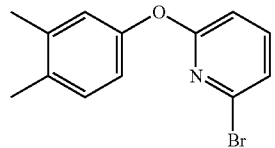 [SMILES: Cc1ccc(Oc2cccc(Br)n2)cc1C]

Essentially following the procedures described for intermediate 6-31, using 3,4-dimethylphenol (300 mg, 2.46 mmol) to afford, after purification by silica gel flash chromatography eluting with a gradient of cyclohexane:dichloromethane—100:0 to 50:50, the title compound as a colorless oil (623 mg, 91% yield).). ESIMS m/z [M+H]$^+$ 280.08.

Example 65: (5R)-3-[6-(3,4-dimethylphenoxy)-2-pyridyl]-5-ethyl-5-methyl-imidazolidine-2,4-dione

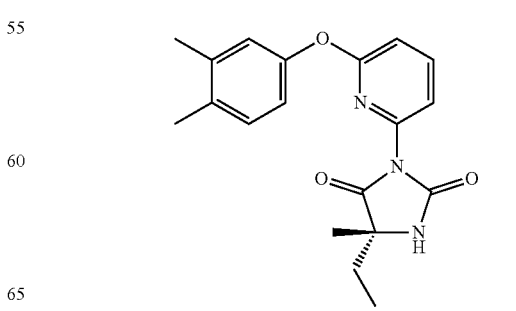

Essentially following the procedures described for example 2, using intermediate 6-39 (200 mg, 0.72 mmol) and intermediate 2-1 (142 mg, 0.79 mmol) to afford, after purification by silica gel flash chromatography eluting with a gradient of cyclohexane:ethyl acetate—100:0 to 0:100, the title compound as a white solid (158 mg, 64% yield). $^1$H NMR (300 MHz, DMSO-$d_6$) 8.48 (bs, 1H), 7.95 (dd, J=7.6 and 8.2 Hz, 1H), 7.18-7.07 (m, 2H), 7.00 (d, J=2.3 Hz, 1H), 6.93-6.84 (m, 2H), 2.18 (s, 6H), 1.80-1.54 (m, 2H), 1.33 (s, 3H), 0.81 (t, J=7.4 Hz, 3H). ESIMS m/z [M+H]$^+$ 340.33

Synthesis of Example 66

Intermediate 6-40: 2-bromo-6-[(2,2-difluoro-1,3-benzodioxol-5-yl)oxy]pyridine

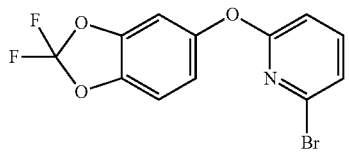 [SMILES: FC1(F)Oc2ccc(Oc3cccc(Br)n3)cc2O1]

Essentially following the procedures described for intermediate 6-31, using intermediate 1-11 (300 mg, 1.72 mmol) to afford, after purification by silica gel flash chromatography eluting with a gradient of cyclohexane:dichloromethane—100:0 to 0:100, the title compound as a white solid (181 mg, 32% yield).). ESIMS m/z [M+H]$^+$ 332.08.

Example 66: (5R)-3-[6-[(2,2-difluoro-1,3-benzodioxol-5-yl)oxy]-2-pyridyl]-5-ethyl-5-methyl-imidazolidine-2,4-dione

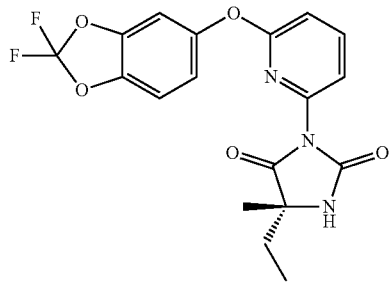 [SMILES: CC[C@@]1(C)NC(=O)N(c2cccc(Oc3ccc4c(c3)OC(F)(F)O4)n2)C1=O]

Essentially following the procedures described for example 2, using intermediate 6-40 (180 mg, 0.55 mmol) and intermediate 2-1 (85 mg, 0.60 mmol) to afford, after purification by silica gel flash chromatography eluting with a gradient of cyclohexane:ethyl acetate—100:0 to 0:100 and lyophilization using water and acetonitrile, the title compound as a white solid (19 mg, 9% yield). $^1$H NMR (300 MHz, DMSO-$d_6$) 8.49 (bs, 1H), 8.01 (dd, J=7.8 and 7.9 Hz, 1H), 7.46-7.40 (m, 2H), 7.16 (d, J=7.6 Hz, 1H), 7.08-6.98 (m, 2H), 1.77-1.53 (m, 2H), 1.32 (s, 3H), 0.76 (t, J=7.4 Hz, 3H). ESIMS m/z [M+H]$^+$ 392.33

Synthesis of Example 67

Intermediate 6-41: 2-bromo-6-(2,3-dihydrobenzofuran-6-yloxy)pyridine

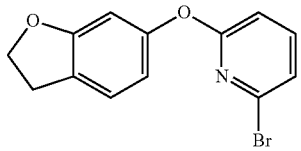

Essentially following the procedures described for intermediate 6-31, using 2,3-dihydrobenzofuran-6-ol (250 mg, 1.83 mmol) to afford, after purification by silica gel flash chromatography eluting with a gradient of cyclohexane:dichloromethane—100:0 to 40:60, the title compound as a white solid (422 mg, 79% yield).). ESIMS m/z [M+H]$^+$ 292.25

Example 67: (5R)-3-[6-(2,3-dihydrobenzofuran-6-yloxy)-2-pyridyl]-5-ethyl-5-methyl-imidazolidine-2,4-dione

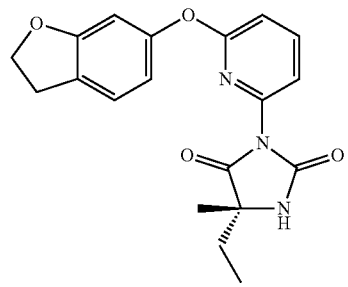

Essentially following the procedures described for example 2, using intermediate 6-41 (200 mg. 0.68 mmol) and intermediate 2-1 (107 mg. 0.75 mmol) to afford, after purification by silica gel flash chromatography eluting with a gradient of cyclohexane:ethyl acetate—100:0 to 0:100, the title compound as a white solid (48 mg, 19% yield). $^1$H NMR (300 MHz, DMSO-$d_6$) 8.49 (bs, 1H), 7.96 (dd, J=7.8 and 8.0 Hz, 1H), 7.21 (d, J=8.4 Hz, 1H), 7.12 (d, J=7.5 Hz, 1H), 6.92 (d, J=8.2 Hz, 1H), 6.63-6.55 (m, 2H), 4.56 (t, J=8.7 Hz, 2H), 3.14 (t, J=8.7 Hz, 2H), 1.78-1.52 (m, 2H), 1.33 (s, 3H), 0.81 (t, J=7.4 Hz, 3H). ESIMS m/z [M+H]$^+$ 354.33

Synthesis of Example 69

Intermediate 6-43: 2-bromo-6-indan-4-yloxy-pyridine

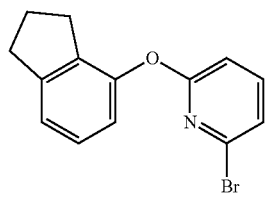 [SMILES: Brc1cccc(Oc2cccc3c2CCC3)n1]

Essentially following the procedures described for intermediate 6-31, using indan-4-ol (200 mg, 1.49 mmol) to afford, after purification by silica gel flash chromatography eluting with a gradient of cyclohexane:dichloromethane—100:0 to 40:60, the title compound as a white solid (247 mg, 57% yield).). ESIMS m/z [M+H]⁺ 290.17

Example 69: (5R)-5-ethyl-3-(6-indan-4-yloxy-2-pyridyl)-5-methyl-imidazolidine-2,4-dione

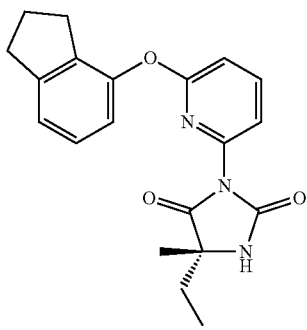 [SMILES: CC[C@@]1(C)NC(=O)N(c2cccc(Oc3cccc4c3CCC4)n2)C1=O]

Essentially following the procedures described for example 2, using intermediate 6-43 (245 mg, 0.84 mmol) and intermediate 2-1 (132 mg, 0.93 mmol) to afford, after purification by silica gel flash chromatography eluting with a gradient of cyclohexane:ethyl acetate—100:0 to 0:100 and lyophilization using water and methanol, the title compound as a white solid (208 mg, 70% yield). $^1$H NMR (300 MHz, DMSO-d$_6$) 8.46 (bs, 1H), 7.96 (app. t, J=7.9 Hz, 1H), 7.20-7.06 (m, 3H), 6.98-6.86 (m, 2H), 2.87 (t, J=7.4 Hz, 2H), 2.63 (t, J=7.4 Hz, 2H), 1.95 (quint, J=7.4 Hz, 2H), 1.76-1.52 (m, 2H), 1.31 (s, 3H), 0.76 (t, J=7.4 Hz, 3H). ESIMS m/z [M+H]⁺ 352.33

Synthesis of Example 70

Intermediate 6-44:
2-bromo-6-(3,5-dimethoxyphenoxy)pyridine

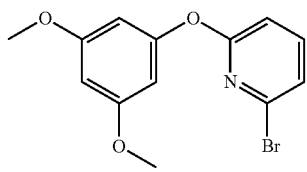 [SMILES: COc1cc(OC)cc(Oc2cccc(Br)n2)c1]

Essentially following the procedures described for intermediate 6-31, using 3,5-dimethoxyphenol (200 mg, 1.30 mmol) to afford, after purification by silica gel flash chromatography eluting with a gradient of cyclohexane:dichloromethane—100:0 to 50:50, the title compound as a white solid (325 mg, 80% yield).). ESIMS m/z [M+H]⁺ 312.08

Example 70: (5R)-3-[6-(3,5-dimethoxyphenoxy)-2-pyridyl]-5-ethyl-5-methyl-imidazolidine-2,4-dione

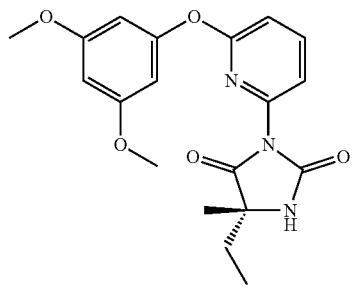 [SMILES: CC[C@@]1(C)NC(=O)N(c2cccc(Oc3cc(OC)cc(OC)c3)n2)C1=O]

Essentially following the procedures described for example 2, using intermediate 6-44 (318 mg, 0.70 mmol) and intermediate 2-1 (100 mg, 0.70 mmol) to afford, after purification by silica gel flash chromatography eluting with a gradient of cyclohexane:ethyl acetate—100:0 to 40:60, the title compound as a white solid (146 mg, 56% yield). $^1$H NMR (300 MHz, DMSO-d$_6$) 8.53 (bs, 1H), 8.01 (dd, J=7.7 and 8.1 Hz, 1H), 7.17 (d, J=7.5 Hz, 1H), 7.01 (d, J=8.2 Hz, 1H), 6.40-6.31 (m, 3H), 3.72 (s, 6H), 1.80-1.56 (m, 2H), 1.36 (s, 3H), 0.83 (t, J=7.4 Hz, 3H). ESIMS m/z [M+H]⁺ 372.25

Synthesis of Example 71

Intermediate 6-45:
2-bromo-6-(3,5-dimethoxy-4-methylphenoxy)pyridine

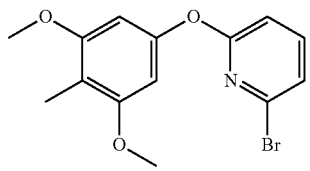 [SMILES: COc1cc(Oc2cccc(Br)n2)cc(OC)c1C]

Essentially following the procedures described for intermediate 6-31, using 3,5-dimethoxy-4-methylphenol (200 mg, 1.19 mmol) to afford, after purification by silica gel flash chromatography eluting with a gradient of cyclohexane:ethylacetate—100:0 to 90:10, the title compound as a white solid (252 mg, 58% yield).). ESIMS m/z [M+H]⁺ 323.9

Example 71: (5R)-3-[6-(3,5-dimethoxy-4-methylphenoxy)-2-pyridyl]-5-ethyl-5-methyl-imidazolidine-2,4-dione

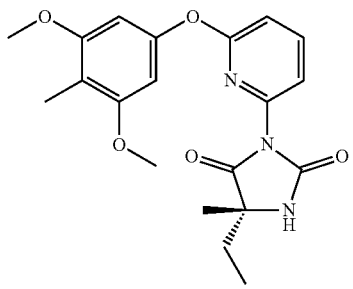 [SMILES: CC[C@@]1(C)NC(=O)N(c2cccc(Oc3cc(OC)c(C)c(OC)c3)n2)C1=O]

Essentially following the procedures described for example 2, using intermediate 6-45 (252 mg, 0.78 mmol) and intermediate 2-1 (142 mg, 0.78 mmol) to afford, after purification by silica gel flash chromatography eluting with a gradient of cyclohexane:ethyl acetate—100:0 to 50:50, the title compound as a white solid (75 mg, 24% yield). $^1$H NMR (300 MHz, DMSO-d$_6$) 8.53 (bs, 1H), 7.99 (dd, J=7.8 and 8.0 Hz, 1H), 7.15 (d, J=7.5 Hz, 1H), 6.99 (d, J=8.2 Hz, 1H), 6.52 (s, 2H), 3.74 (s, 6H), 1.97 (s, 3H), 1.80-1.56 (m, 2H), 1.36 (s, 3H), 0.83 (t, J=7.4 Hz, 3H). ESIMS m/z [M+H]$^+$ 386.33

Synthesis of Example 72

Example 72: (5S)-5-ethyl-3-[6-(3-methoxy-4-methyl-phenoxy)-2-pyridyl]-5-methyl-imidazolidine-2,4-dione

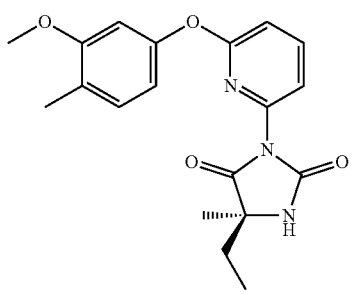 [SMILES: CC[C@]1(C)NC(=O)N(c2cccc(Oc3ccc(C)c(OC)c3)n2)C1=O]

Essentially following the procedures described for example 2, using intermediate 6-32 (200 mg, 0.68 mmol) and intermediate 2-7 (146 mg, 0.68 mmol) to afford, after purification by silica gel flash chromatography eluting with a gradient of cyclohexane:ethyl acetate—100:0 to 0:100, a Sephadex column (eluant DCM/MeOH, 75/25) and lyophilization using water and acetonitrile, the title compound as a white foam (108 mg, 44% yield). $^1$H NMR (300 MHz, DMSO-d$_6$) 8.49 (bs, 1H), 7.97 (dd, J=7.8 and 8.0 Hz, 1H), 7.12 (d, J=7.1 Hz, 1H), 6.95 (d, J=8.2 Hz, 1H), 6.82 (d, J=2.2 Hz, 1H), 6.63 (dd, J=2.2 and 8.0 Hz, 1H), 3.74 (s, 3H), 2.11 (s, 3H), 1.80-1.55 (m, 2H), 1.33 (s, 3H), 0.80 (t, J=7.4 Hz, 3H). ESIMS m/z [M+H]$^+$ 356.42.

Synthesis of Example 73

Example 73: 3-[6-(3-methoxy-4-methyl-phenoxy)-2-pyridyl]-5,5-dimethyl-imidazolidine-2,4-dione

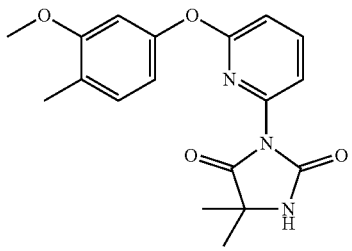 [SMILES: COc1cc(Oc2cccc(N3C(=O)NC(C)(C)C3=O)n2)ccc1C]

Essentially following the procedures described for example 2, using intermediate 6-32 (570 mg, 1.94 mmol) to afford, after purification by silica gel flash chromatography eluting with a gradient of cyclohexane:ethyl acetate—100:0 to 50:50 and lyophilization using water and methanol, the title compound as a white foam (394 mg, 58% yield). $^1$H NMR (300 MHz, DMSO-d$_6$) 8.50 (bs, 1H), 7.99 (dd, J=7.7 and 8.1 Hz, 1H), 7.18 (d, J=7.5 Hz, 1H), 7.15 (d, J=8.1 Hz, 1H), 6.97 (d, J=8.2 Hz, 1H), 6.83 (d, J=2.3 Hz, 1H), 6.64 (dd, J=2.3 and 8.1 Hz, 1H), 3.76 (s, 3H), 2.13 (s, 3H), 1.37 (s, 6H). ESIMS m/z [M+H]$^+$ 342.42.

Synthesis of Example 74

Example 74: 7-[6-(3-methoxy-4-methyl-phenoxy)-2-pyridyl]-5,7-diazaspiro[3.4]octane-6,8-dione

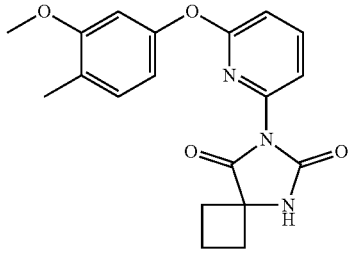 [SMILES: COc1cc(Oc2cccc(N3C(=O)NC4(CCC4)C3=O)n2)ccc1C]

Essentially following the procedures described for example 2, using intermediate 6-32 (200 mg, 0.68 mmol) and intermediate 3-6 (114 mg, 0.82 mmol) to afford, after purification by silica gel flash chromatography eluting with a gradient of cyclohexane:ethyl acetate—100:0 to 0:100, the title compound as a white foam (98 mg, 40% yield). $^1$H NMR (300 MHz, DMSO-d$_6$) 8.90 (bs, 1H), 7.97 (dd, J=7.7 and 8.2 Hz, 1H), 7.18-7.09 (m, 2H), 6.97 (dd, J=0.5 and 8.2 Hz, 1H), 6.80 (d, J=2.3 Hz, 1H), 6.62 (dd, J=2.3 and 8.1 Hz, 1H), 3.75 (s, 3H), 2.48-2.28 (m, 4H), 2.11 (s, 3H), 2.00-1.72 (m, 2H). ESIMS m/z [M+H]$^+$ 354.25.

Synthesis of Example 75

Example 75: 3-[6-(3-methoxy-4-methyl-phenoxy)-2-pyridyl]-1,3-diazaspiro[4.5]decane-2,4-dione

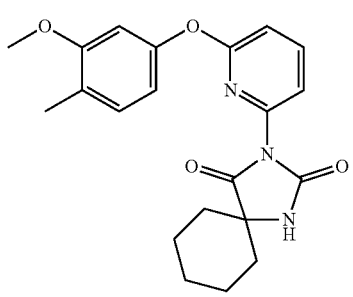 [SMILES: COc1cc(Oc2cccc(N3C(=O)NC4(CCCCC4)C3=O)n2)ccc1C]

Essentially following the procedures described for example 2, using intermediate 6-32 (150 mg, 0.51 mmol) and 3-[6-1,3-diazaspiro[4.5]decane-2,4-dione (103 mg, 0.61 mmol) to afford, after purification by silica gel flash chromatography eluting with a gradient of cyclohexane:ethyl acetate—100:0 to 0:100, the title compound as a white solid (57 mg, 28% yield). $^1$H NMR (300 MHz, DMSO-$d_6$) 8.97 (bs, 1H), 7.97 (dd, J=7.7 and 8.2 Hz, 1H), 7.18-7.09 (m, 2H), 6.96 (d, J=8.2 Hz, 1H), 6.81 (d, J=2.3 Hz, 1H), 6.62 (dd, J=2.3 and 8.1 Hz, 1H), 3.74 (s, 3H), 2.11 (s, 3H), 1.79-1.71.46 (m, 9H), 1.38-1.21 (m, 1H). ESIMS m/z [M+H]$^+$ 382.33

Synthesis of Example 76

Example 76: 3-[6-(3-methoxy-4-methyl-phenoxy)-2-pyridyl]-1,3-diazaspiro[4.4]nonane-2,4-dione

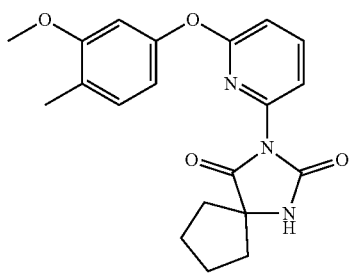 [SMILES: COc1cc(Oc2cccc(N3C(=O)NC4(CCCC4)C3=O)n2)ccc1C]

Essentially following the procedures described for example 2, using intermediate 6-32 (300 mg, 1.02 mmol) and 3-[6-1,3-diazaspiro[4.4]nonane-2,4-dione (157 mg, 1.02 mmol) to afford, after purification by silica gel flash chromatography eluting with a gradient of cyclohexane:ethyl acetate—100:0 to 30:70 and lyophilization using water and acetonitrile, the title compound as a white solid (170 mg, 44% yield). $^1$H NMR (300 MHz, DMSO-$d_6$) 8.77 (bs, 1H), 7.97 (app. t, J=7.9 Hz, 1H), 7.18-7.09 (m, 2H), 6.96 (d, J=8.2 Hz, 1H), 6.81 (d, J=2.3 Hz, 1H), 6.62 (dd, J=2.3 and 8.1 Hz, 1H), 3.74 (s, 3H), 2.11 (s, 3H), 2.08-1.95 (m, 2H), 1.88-1.68 (m, 6H). ESIMS m/z [M+H]$^+$ 368.33

Synthesis of Example 77

Intermediate 6-46: 4-[(6-bromo-2-pyridyl)oxy]-2-isopropyl-benzonitrile

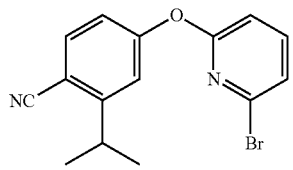 [SMILES: CC(C)c1cc(Oc2cccc(Br)n2)ccc1C#N]

Essentially following the procedures described for intermediate 6-31, using intermediate 5-14 (136 mg, 0.84 mmol) to afford, after purification by silica gel flash chromatography eluting with a gradient of cyclohexane:ethylacetate—100:0 to 70:30, the title compound as a white solid (145 mg, 54% yield). $^1$H NMR (300 MHz, CDCl$_3$-d) 7.66-7.55 (m, 2H), 7.28 (d, J=7.6 Hz, 1H), 7.18 (d, J=2.3 Hz, 1H), 7.05 (dd, J=2.4 and 8.5 Hz, 1H), 6.91 (dd, J=0.5 and 8.1 Hz, 1H), 3.39 (sept, J=6.9 Hz, 1H), 1.30 (d, J=6.9 Hz, 6H).

Example 77: 4-[[6-(4,4-dimethyl-2,5-dioxo-imidazolidin-1-yl)-2-pyridyl]oxy]-2-isopropyl-benzonitrile

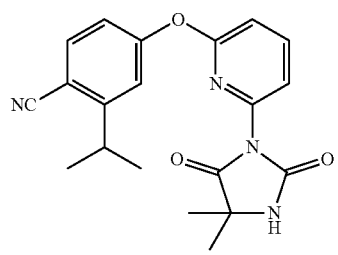 [SMILES: CC(C)c1cc(Oc2cccc(N3C(=O)NC(C)(C)C3=O)n2)ccc1C#N]

Essentially following the procedures described for example 2, using intermediate 6-46 (145 mg, 0.46 mmol) to afford, after purification by silica gel flash chromatography eluting with a gradient of cyclohexane:ethyl acetate—100:0 to 0:100, the title compound as a white solid (77 mg, 46% yield). $^1$H NMR (300 MHz, DMSO-$d_6$) 8.60 (bs, 1H), 8.09 (dd, J=7.9 and 8.0 Hz, 1H), 7.80 (d, J=8.5 Hz, 1H), 7.39 (d, J=2.3 Hz, 1H), 7.29 (d, J=7.6 Hz, 1H), 7.22-7.13 (m, 2H), 3.20 (sept, J=6.9 Hz, 1H), 1.34 (s, 6H), 1.23 (d, J=6.9 Hz, 6H). ESIMS m/z [M+H]$^+$ 365.33

Synthesis of Example 78

Intermediate 7-1: 6-bromo-3-fluoro-2-(3-methoxy-4-methyl-phenoxy)pyridine

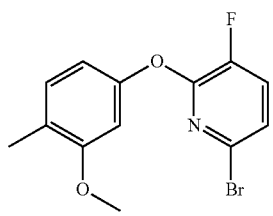 [SMILES: COc1cc(Oc2nc(Br)ccc2F)ccc1C]

Essentially following the procedures described for intermediate 6-31, using intermediate 1-1 (108 mg, 0.78 mmol) to afford, after purification by silica gel flash chromatography eluting with a gradient of cyclohexane:ethylacetate—100:0 to 85:15, the title compound as a colorless oil (217 mg, purity=63%, 56% yield). ESIMS m/z [M+H]$^+$ 311.9.

Example 78: 3-[5-fluoro-6-(3-methoxy-4-methyl-phenoxy)-2-pyridyl]-5,5-dimethyl-imidazolidine-2,4-dione

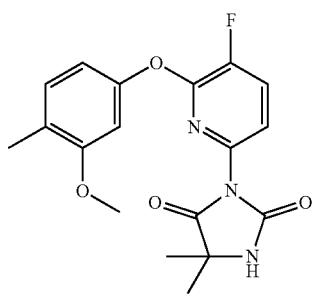 [SMILES: COc1cc(Oc2nc(N3C(=O)NC(C)(C)C3=O)ccc2F)ccc1C]

Essentially following the procedures described for example 2, using intermediate 7-1 (210 mg, 0.68 mmol) to afford, after purification by silica gel flash chromatography eluting with a gradient of cyclohexane:ethyl acetate—100:0 to 0:100 and semi-preparative HPLC, the title compound as a white foam (82 mg, 32% yield). $^1$H NMR (300 MHz, DMSO-d$_6$) 8.59 (bs, 1H), 8.06 (app. t, J=8.4 Hz, 1H), 7.28 (dd, J=2.6 and 8.3 Hz, 1H), 7.13 (d, J=8.2 Hz, 1H), 6.87 (d, J=2.1 Hz, 1H), 6.66 (dd, J=2.3 and 8.1 Hz, 1H), 3.77 (s, 3H), 2.12 (s, 3H), 1.35 (s, 6H). ESIMS m/z [M+H]$^+$ 360.0

Synthesis of Example 79

Intermediate 7-2: 6-bromo-3-fluoro-2-indan-5-yloxy-pyridine

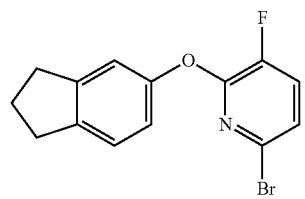 [SMILES: Fc1ccc(Br)nc1Oc1ccc2c(c1)CCC2]

Essentially following the procedures described for intermediate 6-31, using 5-hydroxyindan (108 mg, 0.78 mmol) to afford, after purification by silica gel flash chromatography eluting with a gradient of cyclohexane:ethylacetate—100:0 to 90:10, the title compound as a colorless oil (277 mg, purity=58%, 44% yield). ESIMS m/z [M+H]$^+$ 310.17.

Example 79: 3-(5-fluoro-6-indan-5-yloxy-2-pyridyl)-5,5-dimethyl-imidazolidine-2,4-dione

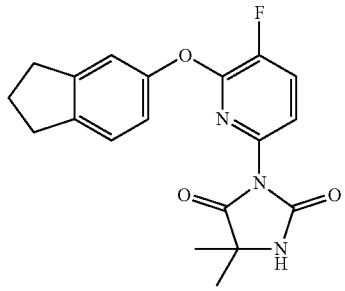 [SMILES: CC1(C)NC(=O)N(c2ccc(F)c(Oc3ccc4c(c3)CCC4)n2)C1=O]

Essentially following the procedures described for example 2, using intermediate 7-2 (277 mg, 0.52 mmol) to afford, after purification by silica gel flash chromatography eluting with a gradient of cyclohexane:ethyl acetate—100:0 to 0:100 and semi-preparative HPLC, the title compound as a white solidified oil (124 mg, 64% yield). $^1$H NMR (300 MHz, DMSO-d$_6$) 8.56 (bs, 1H), 8.05 (app. t, J=8.4 Hz, 1H), 7.27 (dd, J=2.8 and 8.3 Hz, 1H), 7.22 (d, J=8.1 Hz, 1H), 7.06 (s, 1H), 6.92 (dd, J=2.0 and 8.0 Hz, 1H), 2.88-2.80 (m, 4H), 2.13-1.95 (m, 2H), 1.35 (s, 6H). ESIMS m/z [M+H]$^+$ 356.25

Synthesis of Example 80

Intermediate 7-3: 6-bromo-3-fluoro-2-(4-fluoro-3-methoxy-phenoxy)pyridine

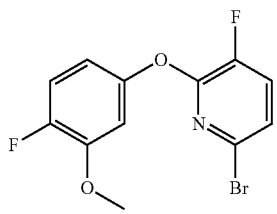 [SMILES: COc1cc(Oc2nc(Br)ccc2F)ccc1F]

Essentially following the procedures described for intermediate 6-31, using 4-fluoro-3-methoxyphenol (167 mg, 1.18 mmol) to afford, after purification by silica gel flash chromatography eluting with a gradient of cyclohexane:dichloromethane—100:0 to 85:15, the title compound as a colorless oil (265 mg, purity=74%, 53% yield). ESIMS m/z [M+H]$^+$ 316.17.

Example 80: 3-[5-fluoro-6-(4-fluoro-3-methoxy-phenoxy)-2-pyridyl]-5,5-dimethyl-imidazolidine-2,4-dione

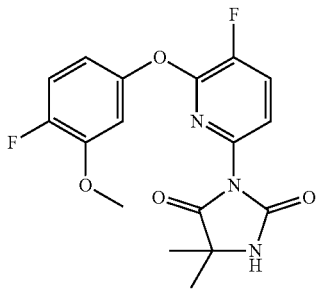 [SMILES: COc1cc(Oc2nc(N3C(=O)NC(C)(C)C3=O)ccc2F)ccc1F]

Essentially following the procedures described for example 2, using intermediate 7-3 (265 mg, 0.62 mmol) to afford, after purification by silica gel flash chromatography eluting with a gradient of cyclohexane:ethyl acetate—100:0 to 0:100 and semi-preparative HPLC, the title compound as a white solidified oil (174 mg, 76% yield). $^1$H NMR (300 MHz, DMSO-$d_6$) 8.59 (bs, 1H), 8.05 (dd, J=8.5 and 9.5 Hz, 1H), 7.33-7.18 (m, 2H), 7.14 (dd, J=2.8 and 7.4 Hz, 1H), 6.81-6.72 (m, 1H), 3.83 (s, 3H), 1.35 (s, 6H). ESIMS m/z [M+H]$^+$ 364.17

Synthesis of Example 81

Intermediate 7-4: 2-(benzofuran-6-yloxy)-6-bromo-3-fluoro-pyridine

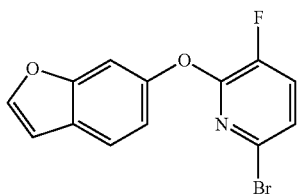 [SMILES: Fc1ccc(Br)nc1Oc1ccc2ccoc2c1]

Essentially following the procedures described for intermediate 6-31, using benzofuran-6-ol (158 mg, 1.18 mmol) to afford, after purification by silica gel flash chromatography eluting with a gradient of cyclohexane:ethylacetate—100:0 to 90:10, the title compound as a colorless oil (305 mg, purity=64%, 54% yield). ESIMS m/z [M+H]$^+$ 308.08.

Example 81: 3-[6-(benzofuran-6-yloxy)-5-fluoro-2-pyridyl]-5,5-dimethyl-imidazolidine-2,4-dione

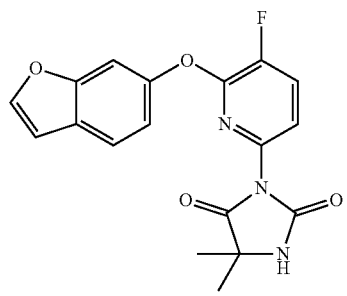 [SMILES: CC1(C)NC(=O)N(c2ccc(F)c(Oc3ccc4ccoc4c3)n2)C1=O]

Essentially following the procedures described for example 2, using intermediate 7-4 (300 mg, 0.62 mmol) to afford, after purification by silica gel flash chromatography eluting with a gradient of cyclohexane:ethyl acetate—100:0 to 0:100 and semi-preparative HPLC, the title compound as a white solidified oil (134 mg, 60% yield). $^1$H NMR (300 MHz, DMSO-$d_6$) 8.54 (bs, 1H), 8.08 (app. t, J=8.4 Hz, 1H), 8.01 (app. t, J=2.2 Hz, 1H), 7.66 (d, J=8.5 Hz, 1H), 7.56 (d, J=1.5 Hz, 1H), 7.30 (dd, J=2.8 and 8.3 Hz, 1H), 7.13 (dd, J=2.1 and 8.5 Hz, 1H), 6.97 (d, J=1.3 Hz, 1H), 1.33 (s, 6H). ESIMS m/z [M+H]$^+$ 356.17

Synthesis of Example 82

Intermediate 7-5: 6-bromo-3-fluoro-2-(4-chloro-3-methoxy-phenoxy)pyridine

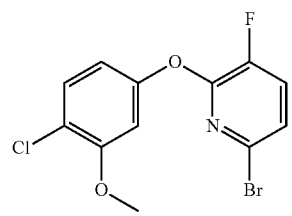 [SMILES: COc1cc(Oc2nc(Br)ccc2F)ccc1Cl]

Essentially following the procedures described for intermediate 6-31, using 4-chloro-3-methoxyphenol (187 mg, 1.18 mmol) to afford, after purification by silica gel flash chromatography eluting with a gradient of cyclohexane:dichloromethane—100:0 to 85:15, the title compound as a colorless oil (313 mg, 80% yield). $^1$H NMR (300 MHz, CDCl$_3$-d) 7.86 (app. t, J=8.4 Hz, 1H), 7.51-7.39 (m, 2H), 7.10 (d, J=2.6 Hz, 1H), 6.81 (dd, J=2.6 and 8.6 Hz, 1H), 3.82 (s, 3H).

Example 82: 3-[5-fluoro-6-(4-chloro-3-methoxy-phenoxy)-2-pyridyl]-5,5-dimethyl-imidazolidine-2,4-dione

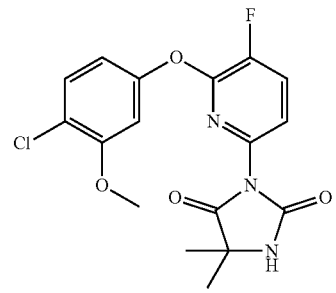 [SMILES: COc1cc(Oc2nc(N3C(=O)NC(C)(C)C3=O)ccc2F)ccc1Cl]

Essentially following the procedures described for example 2, using intermediate 7-5 (310 mg, 0.94 mmol) to afford, after purification by silica gel flash chromatography eluting with a gradient of cyclohexane:ethyl acetate—100:0 to 0:100 and semi-preparative HPLC, the title compound as a white solidified oil (133 mg, 37% yield). $^1$H NMR (300 MHz, DMSO-$d_6$) 8.59 (bs, 1H), 8.09 (app. t, J=8.4 Hz, 1H), 7.44 (d, J=8.7 Hz, 1H), 7.32 (dd, J=2.8 and 8.4 Hz, 1H), 7.12 (d, J=2.6 Hz, 1H), 6.81 (dd, J=2.6 and 8.7 Hz, 1H), 3.85 (s, 3H), 1.36 (s, 6H). ESIMS m/z [M+H]$^+$ 380.25

Synthesis of Example 83

Intermediate 7-6: 6-bromo-3-fluoro-2-(3-fluoro-4-methyl-phenoxy)pyridine

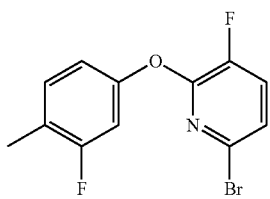 [SMILES: Cc1ccc(Oc2nc(Br)ccc2F)cc1F]

Essentially following the procedures described for intermediate 6-31, using 3-fluoro-4-methylphenol (148 mg, 1.18 mmol) to afford, after purification by silica gel flash chromatography eluting with a gradient of cyclohexane:ethylacetate—100:0 to 50:50, the title compound as a colorless oil (220 mg, purity=64%, 40% yield). ESIMS m/z [M+H]$^+$ 300.17.

Example 83: 3-[5-fluoro-6-(3-fluoro-4-methyl-phenoxy)-2-pyridyl]-5,5-dimethyl-imidazolidine-2,4-dione

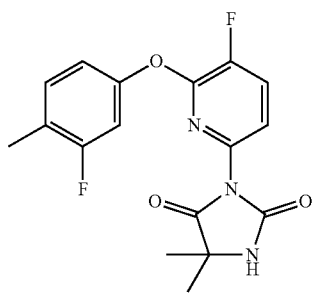 [SMILES: Cc1ccc(Oc2nc(N3C(=O)NC(C)(C)C3=O)ccc2F)cc1F]

Essentially following the procedures described for example 2, using intermediate 7-6 (220 mg, 0.73 mmol) to afford, after purification by silica gel flash chromatography eluting with a gradient of cyclohexane:ethyl acetate—100:0 to 0:100 and semi-preparative HPLC, the title compound as a white foam (47 mg, 18% yield). $^1$H NMR (300 MHz, DMSO-d$_6$) 8.56 (bs, 1H), 8.06 (app. t, J=8.5 Hz, 1H), 7.34-7.24 (m, 2H), 7.12 (dd, J=2.3 and 11.0 Hz, 1H), 6.95 (dd, J=2.4 and 8.4 Hz, 1H), 2.20 (s, 3H), 1.33 (s, 6H). ESIMS m/z [M+H]$^+$ 348.25

Synthesis of Example 84

Intermediate 7-7: 6-bromo-2-[(2,2-difluoro-1,3-benzodioxol-5-yl)oxy]-3-fluoro-pyridine

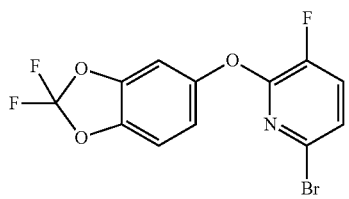 [SMILES: Fc1ccc(Br)nc1Oc1ccc2c(c1)OC(F)(F)O2]

Essentially following the procedures described for intermediate 6-31, using intermediate 1-11 (90 mg, 0.78 mmol) to afford, after purification by silica gel flash chromatography eluting with a gradient of cyclohexane:ethylacetate—100:0 to 50:50, the title compound as a colorless oil (100 mg, purity=67%, 37% yield).). $^1$H NMR (300 MHz, CDCl$_3$-d) 7.87 (app. t, J=8.3 Hz, 1H), 7.57-7.49 (m, 3H), 7.09 (dd, J=2.4 and 8.8 Hz, 1H).

Example 84: 3-[6-[(2,2-difluoro-1,3-benzodioxol-5-yl)oxy]-5-fluoro-2-pyridyl]-5,5-dimethyl-imidazolidine-2,4-dione

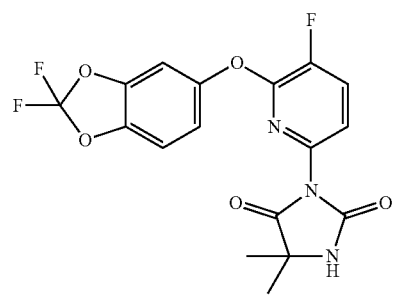 [SMILES: CC1(C)NC(=O)N(c2ccc(F)c(Oc3ccc4c(c3)OC(F)(F)O4)n2)C1=O]

Essentially following the procedures described for example 2, using intermediate 7-7 (100 mg, 0.29 mmol) to afford, after purification by silica gel flash chromatography eluting with a gradient of cyclohexane:ethyl acetate—100:0 to 0:100 and semi-preparative HPLC, the title compound as a white solidified oil (40 mg, 35% yield). $^1$H NMR (300 MHz, DMSO-d$_6$) 8.56 (bs, 1H), 8.06 (app. t, J=8.4 Hz, 1H), 7.48 (d, J=2.4 Hz, 1H), 7.43 (d, J=8.8 Hz, 1H), 7.30 (dd, J=2.8 and 8.4 Hz, 1H), 7.06 (dd, J=2.4 and 8.8 Hz, 1H), 1.33 (s, 6H). ESIMS m/z [M+H]$^+$ 396.25

Synthesis of Example 85

Intermediate 7-8: 6-bromo-3-fluoro-2-[3-methoxy-4-(trifluoromethyl)-phenoxy]pyridine

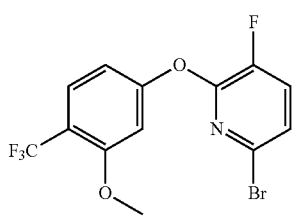 [SMILES: COc1cc(Oc2nc(Br)ccc2F)ccc1C(F)(F)F]

Essentially following the procedures described for intermediate 6-31, using 3-methoxy-4-(trifluoromethyl)phenol (226 mg, 1.18 mmol) to afford, after purification by silica gel flash chromatography eluting with a gradient of cyclohexane:dichloromethane—100:0 to 50:50, the title compound as a colorless oil (163 mg, 38% yield). $^1$H NMR (300 MHz, CDCl$_3$-d) 7.98-7.85 (m, 1H), 7.67 (d, J=8.7 Hz, 1H), 7.50 (dd, J=2.8 and 8.4 Hz, 1H), 7.20 (d, J=1.8 Hz, 1H), 6.91 (dd, J=2.0 and 8.5 Hz, 1H), 3.86 (s, 3H).

Example 85: 3-[5-fluoro-6-[3-methoxy-4-(trifluoromethyl)-phenoxy]-2-pyridyl]-5,5-dimethyl-imidazolidine-2,4-dione

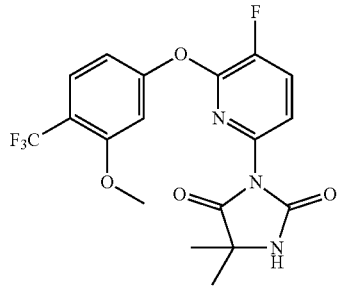 [SMILES: COc1cc(Oc2nc(N3C(=O)NC(C)(C)C3=O)ccc2F)ccc1C(F)(F)F]

Essentially following the procedures described for example 2, using intermediate 7-8 (163 mg, 0.45 mmol) to afford, after purification by silica gel flash chromatography eluting with a gradient of cyclohexane:ethyl acetate—100:0 to 0:100, semi-preparative HPLC and Sephadex column (eluant DCM/MeOH, 75/25), the title compound as a white solidified oil (46 mg, 25% yield). $^1$H NMR (300 MHz, DMSO-$d_6$) 8.59 (bs, 1H), 8.11 (app. t, J=8.5 Hz, 1H), 7.62 (d, J=8.7 Hz, 1H), 7.37 (dd, J=2.8 and 8.4 Hz, 1H), 7.20 (s, 1H), 6.88 (d, J=8.6 Hz, 1H), 3.87 (s, 3H), 1.34 (s, 6H). ESIMS m/z [M+H]$^+$ 414.33

Synthesis of Example 86

Example 86: 7-[5-fluoro-6-(3-methoxy-4-methyl-phenoxy)-2-pyridyl]-5,7-diazaspiro[3.4]octane-6,8-dione

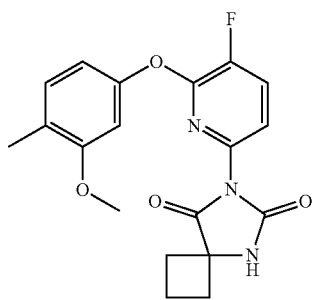 [SMILES: COc1cc(Oc2nc(N3C(=O)NC4(CCC4)C3=O)ccc2F)ccc1C]

Essentially following the procedures described for example 2, using intermediate 7-1 (220 mg, 0.70 mmol) and 5,7-diazaspiro[3.4]octane-6,8-dione (119 mg, 0.85 mmol) to afford, after purification by silica gel flash chromatography eluting with a gradient of cyclohexane:ethyl acetate—100:0 to 0:100 and lyophilization using water and methanol, the title compound as a white powder (126 mg, 47% yield). $^1$H NMR (300 MHz, DMSO-$d_6$) 8.90 (bs, 1H), 8.03 (dd, J=8.5 and 9.6 Hz, 1H), 7.23 (dd, J=2.7 and 8.3 Hz, 1H), 7.11 (d, J=8.2 Hz, 1H), 6.84 (d, J=2.2 Hz, 1H), 6.63 (dd, J=2.2 and 8.2 Hz, 1H), 3.75 (s, 3H), 2.45-2.22 (m, 4H), 2.10 (s, 3H), 1.98-1.70 (m, 2H). ESIMS m/z [M+H]$^+$ 372.25

Synthesis of Example 87

Example 87: 3-[5-fluoro-6-(3-methoxy-4-methyl-phenoxy)-2-pyridyl]-1,3-diazaspiro[4.5]decane-2,4-dione

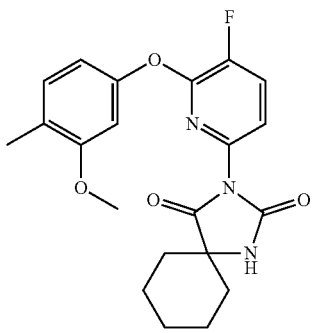 [SMILES: COc1cc(Oc2nc(N3C(=O)NC4(CCCCC4)C3=O)ccc2F)ccc1C]

Essentially following the procedures described for example 2, using intermediate 7-1 (200 mg, 0.64 mmol) and 1,3-diazaspiro[4.5]decane-2,4-dione (130 mg, 0.77 mmol) to afford, after purification by silica gel flash chromatography eluting with a gradient of cyclohexane:ethyl acetate—100:0 to 0:100, the title compound as a white foam (171 mg, 65% yield). $^1$H NMR (300 MHz, DMSO-$d_6$) 8.97 (bs, 1H), 8.03 (dd, J=8.3 and 8.4 Hz, 1H), 7.25 (dd, J=2.8 and 8.3 Hz, 1H), 7.11 (dd, J=0.7 and 8.1 Hz, 1H), 6.85 (d, J=2.3 Hz, 1H), 6.64 (dd, J=2.3 and 8.1 Hz, 1H), 3.75 (s, 3H), 2.10 (s, 3H), 1.75-1.45 (m, 9H), 1.38-1.20 (m, 1H). ESIMS m/z [M+H]$^+$ 400.33

Synthesis of Example 88

Example 88: 3-[5-fluoro-6-(3-methoxy-4-methyl-phenoxy)-2-pyridyl]-1,3-diazaspiro[4.4]nonane-2,4-dione

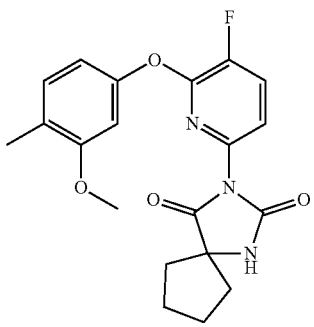 [SMILES: COc1cc(Oc2nc(N3C(=O)NC4(CCCC4)C3=O)ccc2F)ccc1C]

Essentially following the procedures described for example 2, using intermediate 7-1 (230 mg, 0.74 mmol) and 1,3-diazaspiro[4.4]nonane-2,4-dione (115 mg, 0.74 mmol) to afford, after purification by silica gel flash chromatography eluting with a gradient of cyclohexane:ethyl acetate—100:0 to 30:70, the title compound as a white foam (150 mg, 52% yield). $^1$H NMR (300 MHz, DMSO-$d_6$) 8.76 (bs, 1H), 8.03 (dd, J=8.4 and 8.5 Hz, 1H), 7.25 (dd, J=2.8 and 8.3 Hz, 1H), 7.11 (d, J=8.1 Hz, 1H), 6.85 (d, J=2.3 Hz, 1H), 6.64

(dd, J=2.3 and 8.1 Hz, 1H), 3.75 (s, 3H), 2.10 (s, 3H), 2.05-1.95 (m, 2H), 1.84-1.68 (m, 6H). ESIMS m/z [M+H]+ 386.33

Synthesis of Example 89

Example 89: (5R)-5-ethyl-3-[5-fluoro-6-(3-methoxy-4-methyl-phenoxy)-2-pyridyl]-5-methyl-imidazolidine-2,4-dione

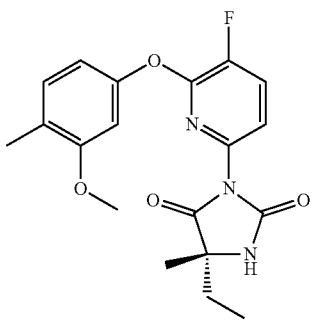 [SMILES: CC[C@@]1(C)NC(=O)N(c2ccc(F)c(Oc3ccc(C)c(OC)c3)n2)C1=O]

Essentially following the procedures described for example 2, using intermediate 7-1 (115 mg, 0.37 mmol) and intermediate 2-1 (52 mg, 0.37 mmol) to afford, after purification by silica gel flash chromatography eluting with a gradient of cyclohexane:ethyl acetate—100:0 to 40:60, the title compound as a white foam (63 mg, 44% yield). $^1$H NMR (300 MHz, DMSO-$d_6$) 8.52 (bs, 1H), 8.05 (dd, J=8.3 and 8.4 Hz, 1H), 7.24 (dd, J=2.8 and 8.3 Hz, 1H), 7.12 (d, J=8.1 Hz, 1H), 6.87 (d, J=2.3 Hz, 1H), 6.66 (dd, J=2.3 and 8.1 Hz, 1H), 3.76 (s, 3H), 2.12 (s, 3H), 1.80-1.50 (m, 2H), 1.33 (s, 3H), 0.78 (t, J=7.4 Hz, 3H). ESIMS m/z [M+H]+ 374.0

Synthesis of Example 90

Intermediate 8-1: 3-fluoro-4-iodo-2-(3-methoxy-4-methyl-phenoxy)pyridine

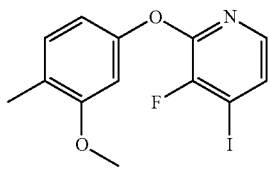 [SMILES: COc1cc(Oc2nccc(I)c2F)ccc1C]

Essentially following the procedures described for intermediate 1-2, using 2,3-difluoro-4-iodopyridine (400 mg, 1.66 mmol) after stirring at 50° C. for 18 h to afford, after purification by silica gel flash chromatography eluting with a gradient of cyclohexane:dichloromethane—100:0 to 50:50, the title compound as a white solid (510 mg, 86% yield). $^1$H NMR (300 MHz, CDCl$_3$-d) 7.57 (d, J=5.3 Hz, 1H), 7.36-7.29 (m, 1H), 7.17-7.10 (m, 1H), 6.67-6.61 (m, 1H), 3.80 (s, 3H), 2.20 (s, 3H).

Example 90: 3-[3-fluoro-2-(3-methoxy-4-methyl-phenoxy)-4-pyridyl]-1,3-diazaspiro[4.4]nonane-2,4-dione

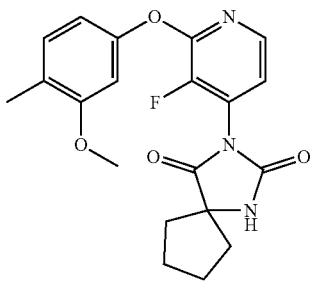 [SMILES: COc1cc(Oc2nccc(N3C(=O)NC4(CCCC4)C3=O)c2F)ccc1C]

Essentially following the procedures described for example 2, using intermediate 8-1 (200 mg, 0.56 mmol) and 1,3-diazaspiro[4.4]nonane-2,4-dione (95 mg, 0.61 mmol) to afford, after purification by silica gel flash chromatography eluting with a gradient of cyclohexane:ethyl acetate—100:0 to 50:50, the title compound as a colorless oil (8 mg, 3% yield). $^1$H NMR (300 MHz, DMSO-$d_6$) 9.03 (bs, 1H), 8.00 (d, J=5.3 Hz, 1H), 7.25 (dd, J=4.6 and 5.1 Hz, 1H), 7.15 (d, J=8.1 Hz, 1H), 6.83 (d, J=2.1 Hz, 1H), 6.66 (dd, J=2.1 and 8.0 Hz, 1H), 3.74 (s, 3H), 2.12 (s, 3H), 2.12-2.00 (m, 2H), 1.96-1.66 (m, 6H). ESIMS m/z [M+H]+ 386.25

Synthesis of Example 91

Example 91: 3-[3-fluoro-2-(3-methoxy-4-methyl-phenoxy)-4-pyridyl]-1,3-diazaspiro[4.5]decane-2,4-dione

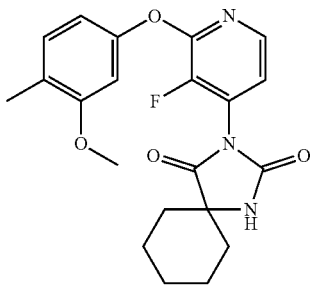 [SMILES: COc1cc(Oc2nccc(N3C(=O)NC4(CCCCC4)C3=O)c2F)ccc1C]

Essentially following the procedures described for example 2, using intermediate 8-1 (265 mg, 0.74 mmol) and 1,3-diazaspiro[4.5]decane-2,4-dione (136 mg, 0.81 mmol) to afford, after purification by silica gel flash chromatography eluting with a gradient of cyclohexane:ethyl acetate—100:0 to 50:50 and lyophilization using water and acetonitrile, the title compound as a white foam (15 mg, 5% yield). $^1$H NMR (300 MHz, DMSO-$d_6$) 9.23 (bs, 1H), 8.00 (d, J=5.3 Hz, 1H), 7.24 (dd, J=4.6 and 5.1 Hz, 1H), 7.15 (d, J=8.1 Hz, 1H), 6.83 (d, J=2.1 Hz, 1H), 6.66 (dd, J=2.1 and 8.0 Hz, 1H), 3.74 (s, 3H), 2.13 (s, 3H), 1.88-1.45 (m, 9H), 1.45-1.30 (m, 1H). ESIMS m/z [M+H]+ 400.33

Synthesis of Example 92

Intermediate 8-2: 2-[(2,2-difluoro-1,3-benzodioxol-5-yl)oxy]-3-fluoro-4-iodo-pyridine

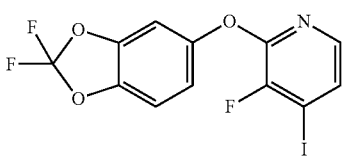 [SMILES: Fc1c(I)ccnc1Oc1ccc2c(c1)OC(F)(F)O2]

Essentially following the procedures described for intermediate 1-2, using 2,3-difluoro-4-iodopyridine (500 mg, 2.07 mmol) and intermediate 1-11 (397 mg, 2.28 mmol) after stirring at 50° C. for 18 h to afford, after purification by silica gel flash chromatography eluting with a gradient of cyclohexane:ethyl acetate—100:0 to 70:30, the title compound as a white solid (735 mg, 90% yield). $^1$H NMR (300 MHz, CDCl$_3$-d) 7.56 (d, J=5.3 Hz, 1H), 7.38 (dd, J=5.2 and 5.2 Hz, 1H), 7.07 (d, J=8.6 Hz, 1H), 6.95 (d, J=2.3 Hz, 1H), 6.88 (dd, J=2.4 and 8.6 Hz, 1H).

Example 92: 3-[2-[(2,2-difluoro-1,3-benzodioxol-5-yl)oxy]-3-fluoro-4-pyridyl]-1,3-diazaspiro[4.4]nonane-2,4-dione

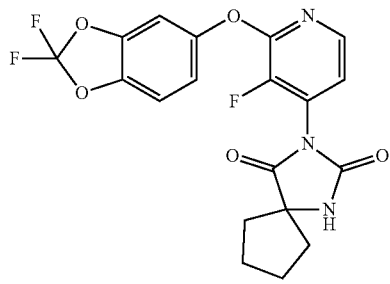 [SMILES: O=C1NC2(CCCC2)C(=O)N1c1ccnc(Oc2ccc3c(c2)OC(F)(F)O3)c1F]

Essentially following the procedures described for example 2, using intermediate 8-2 (300 mg, 0.76 mmol) and 1,3-diazaspiro[4.4]nonane-2,4-dione (130 mg, 0.84 mmol) to afford, after purification by silica gel flash chromatography eluting with a gradient of cyclohexane:ethyl acetate—100:0 to 50:50, a semi-preparative HPLC and a lyophilization using water and acetonitrile, the title compound as a white foam (18 mg, 6% yield). $^1$H NMR (300 MHz, DMSO-d$_6$) 9.03 (bs, 1H), 8.00 (d, J=5.3 Hz, 1H), 7.53 (d, J=2.1 Hz, 1H), 7.46 (d, J=8.7 Hz, 1H), 7.29 (t, J=4.8 Hz, 1H), 7.10 (dd, J=2.1 and 8.7 Hz, 1H), 2.15-1.99 (m, 2H), 1.96-1.68 (m, 6H). ESIMS m/z [M+H]$^+$ 422.25

Synthesis of Example 93

Example 93: 3-[2-[(2,2-difluoro-1,3-benzodioxol-5-yl)oxy]-3-fluoro-4-pyridyl]-1,3-diazaspiro[4.5]decane-2,4-dione

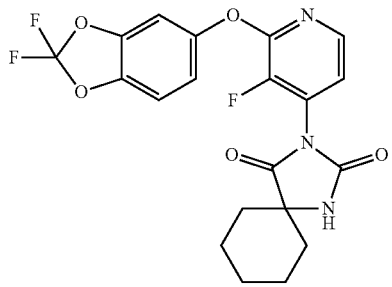 [SMILES: O=C1NC2(CCCCC2)C(=O)N1c1ccnc(Oc2ccc3c(c2)OC(F)(F)O3)c1F]

Essentially following the procedures described for example 2, using intermediate 8-2 (300 mg, 0.76 mmol) and 1,3-diazaspiro[4.5]decane-2,4-dione (140 mg, 0.84 mmol) to afford, after two purifications by silica gel flash chromatography eluting for the first one with a gradient of cyclohexane:ethyl acetate—100:0 to 50:50 and for the second one with a gradient of cyclohexane:dihcloromethane—100:0 to 0:100, the title compound as a white foam (15 mg, 4% yield). $^1$H NMR (300 MHz, DMSO-d$_6$) 9.25 (bs, 1H), 8.00 (d, J=5.3 Hz, 1H), 7.53 (d, J=2.1 Hz, 1H), 7.46 (d, J=8.7 Hz, 1H), 7.29 (t, J=4.8 Hz, 1H), 7.10 (dd, J=2.1 and 8.7 Hz, 1H), 1.86-1.47 (m, 9H), 1.42-1.28 (m, 1H). ESIMS m/z [M+H]$^+$ 436.25.

Cell Biology Protocols and Data

Cell Lines hKv3.1, hKv3.2, hKv3.3, and hKv3.4 were stably expressed in CHO-K1 (Chinese hamster ovary) cells and kept under constant antibiotic selection. For in vitro assays, cells were maintained in appropriate growth medium at 37° C. and 5% CO$_2$ in a humidified incubator.

Electrophysiology

CHO/Kv3.x Cell Preparation hKv3.X expressing cells were plated in T-25 flasks for 3-4 days at 37° C. (no selection antibiotic) prior to use and grown to 80% confluence. Cells were washed twice with PBS (calcium and magnesium free) and detached with a 5-minute treatment at 37° C. with 2-3 mls of Accutase®. Cells were collected, and flask was washed in CHO-SFM II media (Life Technologies Gibco), centrifuged for 2 minutes at ~110×g and resuspended to obtain a single cell suspension of ~2-3×10$^6$ cells/ml.

Solutions and Compound Preparation

The intracellular solution contained the following (in mM): KCl 50, NaCl 10, KF 60, EGTA 20, HEPES 10, adjusted to pH 7.2 with KOH and an osmolarity of 285 mOsmol. Seal enhancer was purchased from Nanion (80 mM NaCl, 3 mM KCl, 10 mM MgCl$_2$, 35 mM CaCl$_2$), 10 mM HEPES, pH7.4, 298 mOsmol. The external solution contained (in mM): NaCl 140, KCl 4, CaCl$_2$) 2, MgCl$_2$ 1, HEPES 10, Glucose 5, adjusted to pH7.4 and an osmolarity of 298 mOsmol.

All compounds were initially tested at 10 uM at a final DMSO concentration of 0.33%. Compounds were dissolved in dimethylsulfoxide (DMSO) at a stock concentration of 30 mM. The compound was further diluted 1:10 to give a stock concentration of 3 mM in DMSO. The final assay solution was diluted 1:300 in External solution to give a final concentration of 10 uM. For the DMSO Control Buffer 30 uL of DMSO was added to 10 mL buffer.

The following voltage protocols were used to assess different hKv3.X channels:

Patchliner Protocol

All electrophysiological recordings were performed at ambient temperature (21-23° C.) using automated patch clamp (Patchliner, Nanion Technologies GmbH) in the whole-cell configuration.

Cell membrane potentials were held at −80 mV, and currents were evoked by voltage steps (1000 ms duration) from −60 to +60 mV in 10 mV increments. This was performed first with vehicle (0.33% DMSO) and then with 10 uM compound, after a 3-minute incubation period. Data was taken from 4 cells per assay.

Data Analysis

The recordings were analysed and selected using peak current amplitude (>100 pA at the −10 mV voltage step) in the absence of compound to eliminate unsuitable cells from analysis. Peak current amplitude was measured and recorded for each voltage step and data was normalised to the maximum current at +60 mV. The normalised Kv3.x currents following addition of the compound were then compared with the currents recorded prior to compound addition (vehicle control). Positive modulation was determined as % potentiation at the voltage step of −10 mV=[current (cmpd)/current (veh)]*100−100. % potentiation ≥50% was considered acceptable. In addition, voltage shift of the IV curve at $V_{1/2}$ was measured. $V_{1/2}$ of ≥−5 mV was also considered acceptable. IV curves were plotted in GraphPad Prism (software version 6.0) and fitted with a Boltzmann equation, where $V_{1/2}$ is the voltage at half-maximal activation.

Electrophysiology Data

| Example # | Structure | Kv3.1 Activity at 10 μM | | Kv3.2 Activity at 10 μM | |
|---|---|---|---|---|---|
| | | Potentiation (%) | Voltage Shift (mV) | Potentiation (%) | Voltage Shift (mV) |
| 1 | | 53 | −2.9 | 21 | −1.23 |
| 3 | | 58 | −4.65 | 66 | −6.71 |
| 4 | | 36 | −5.13 | 14 | −4.12 |
| 6 | | ND | ND | 25 | −3.18 |

-continued

| | | Electrophysiology Data | | | |
|---|---|---|---|---|---|
| | | Kv3.1 Activity at 10 μM | | Kv3.2 Activity at 10 μM | |
| Example # | Structure | Potentiation (%) | Voltage Shift (mV) | Potentiation (%) | Voltage Shift (mV) |
| 8 | | 32 | −4.09 | 22 | −2.39 |
| 9 | | 80 | −6.49 | 30 | −3.92 |
| 10 | | 72 | −5.46 | 21 | −2.67 |
| 12 | | 6 | −3.31 | ND | ND |
| 13 | | 27 | −3.9 | 48 | −4.48 |

-continued

| | | Electrophysiology Data | | | |
|---|---|---|---|---|---|
| | | Kv3.1 Activity at 10 μM | | Kv3.2 Activity at 10 μM | |
| Example # | Structure | Potentiation (%) | Voltage Shift (mV) | Potentiation (%) | Voltage Shift (mV) |
| 15 | | 3 | −0.9 | ND | ND |
| 16 | | ND | ND | 47 | −3.63 |
| 17 | | 28 | −3.12 | ND | ND |
| 19 | | 35 | −0.4 | ND | ND |
| 23 | | 30 | 0.77 | ND | ND |

-continued

| | | Electrophysiology Data | | | |
| | | Kv3.1 Activity at 10 μM | | Kv3.2 Activity at 10 μM | |
| Example # | Structure | Potentiation (%) | Voltage Shift (mV) | Potentiation (%) | Voltage Shift (mV) |
| --- | --- | --- | --- | --- | --- |
| 24 | 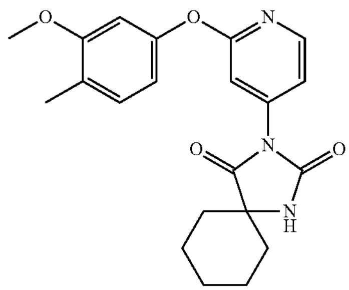 [SMILES: COc1cc(Oc2cc(N3C(=O)NC4(CCCCC4)C3=O)ccn2)ccc1C] | ND | ND | 42 | −5.52 |
| 29 | 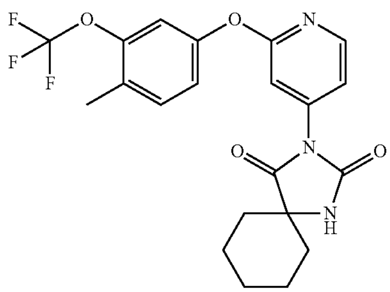 [SMILES: Cc1ccc(Oc2cc(N3C(=O)NC4(CCCCC4)C3=O)ccn2)cc1OC(F)(F)F] | 12 | −0.63 | ND | ND |
| 30 | 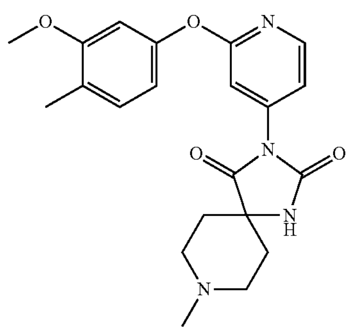 [SMILES: COc1cc(Oc2cc(N3C(=O)NC4(CCN(C)CC4)C3=O)ccn2)ccc1C] | 26 | −0.83 | −4 | 2.06 |
| 32 | 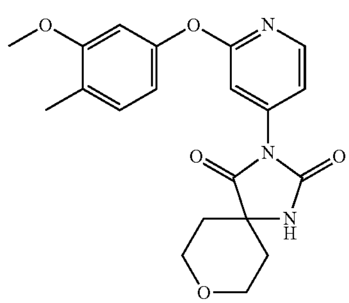 [SMILES: COc1cc(Oc2cc(N3C(=O)NC4(CCOCC4)C3=O)ccn2)ccc1C] | 19 | −2.06 | ND | ND |
| 33 | 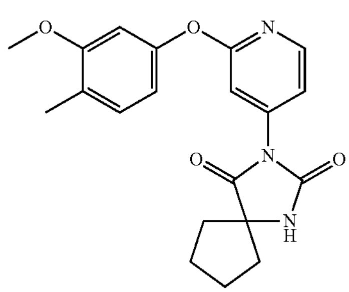 [SMILES: COc1cc(Oc2cc(N3C(=O)NC4(CCCC4)C3=O)ccn2)ccc1C] | 64 | −5.74 | 22 | −2.72 |

-continued
| | | Electrophysiology Data | | | |
|---|---|---|---|---|---|
| | | Kv3.1 Activity at 10 μM | | Kv3.2 Activity at 10 μM | |
| Example # | Structure | Potentiation (%) | Voltage Shift (mV) | Potentiation (%) | Voltage Shift (mV) |
| 34 | 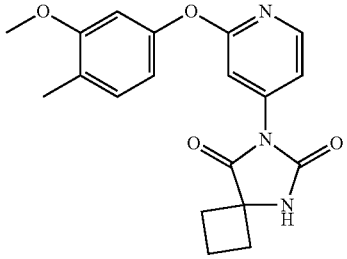 [SMILES: COc1cc(Oc2cc(N3C(=O)NC4(CCC4)C3=O)ccn2)ccc1C] | 27 | −4.19 | 25 | −1.25 |
| 35 | 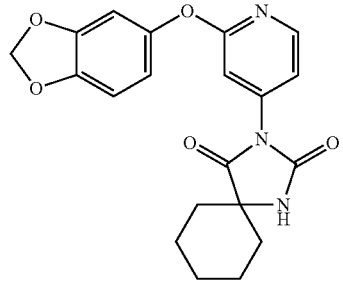 [SMILES: O=C1NC2(CCCCC2)C(=O)N1c1ccnc(Oc2ccc3c(c2)OCO3)c1] | 41 | −3.4 | 55 | −3.73 |
| 36 | 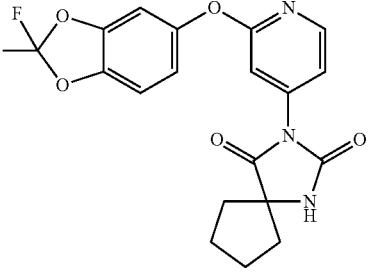 | 85 | −6.21 | 43 | −4.8 |
| 37 | 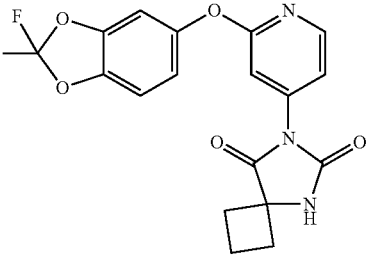 | 90 | −5.21 | 63 | −3.6 |
| 38 | 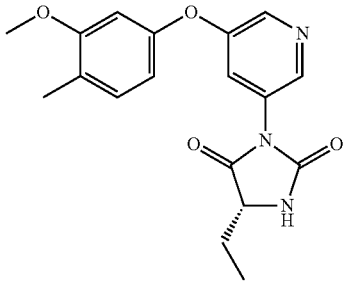 [SMILES: CC[C@H]1NC(=O)N(c2cncc(Oc3ccc(C)c(OC)c3)c2)C1=O] | 48 | −2.8 | ND | ND |

-continued

| | | Electrophysiology Data | | | |
|---|---|---|---|---|---|
| | | Kv3.1 Activity at 10 µM | | Kv3.2 Activity at 10 µM | |
| Example # | Structure | Potentiation (%) | Voltage Shift (mV) | Potentiation (%) | Voltage Shift (mV) |
| 39 | | 25 | −2.77 | 31 | −3.78 |
| 40 | | 78 | −4.77 | ND | ND |
| 41 | | 67 | −4.46 | 53 | −3.77 |
| 42 | | 25 | −3.07 | ND | ND |
| 44 | | 45 | −3.03 | 28 | −2.81 |

-continued

| | | Electrophysiology Data | | | |
| | | Kv3.1 Activity at 10 μM | | Kv3.2 Activity at 10 μM | |
| Example # | Structure | Potentiation (%) | Voltage Shift (mV) | Potentiation (%) | Voltage Shift (mV) |
| --- | --- | --- | --- | --- | --- |
| 45 | | 19 | −2.36 | 61 | −6.69 |
| 47 | | 29 | −1.49 | ND | ND |
| 48 | | 62 | −4.26 | 61 | −5.3 |
| 51 | | 7 | −1.99 | ND | ND |
| 52 | | 14 | −3.5 | ND | ND |

-continued

| | | Electrophysiology Data | | | |
|---|---|---|---|---|---|
| | | Kv3.1 Activity at 10 μM | | Kv3.2 Activity at 10 μM | |
| Example # | Structure | Potentiation (%) | Voltage Shift (mV) | Potentiation (%) | Voltage Shift (mV) |
| 54 | | 11 | −1.69 | ND | ND |
| 55 | | 11 | −1.41 | ND | ND |
| 56 | | 19 | −2.7 | ND | ND |
| 57 | | −23 | 2.18 | ND | ND |

| Example # | Structure | Kv3.1 Activity at 10 μM | | Kv3.2 Activity at 10 μM | |
|---|---|---|---|---|---|
| | | Potentiation (%) | Voltage Shift (mV) | Potentiation (%) | Voltage Shift (mV) |
| 58 | | 35 | −5.32 | 33 | −2.6 |
| 59 | | 10 | −1.95 | ND | ND |
| 60 | | 51 | −3.45 | ND | ND |
| 61 | | 46 | −3.55 | ND | ND |
| 62 | | 57 | −4.05 | ND | ND |

-continued

| | | Electrophysiology Data | | | |
|---|---|---|---|---|---|
| | | Kv3.1 Activity at 10 μM | | Kv3.2 Activity at 10 μM | |
| Example # | Structure | Potentiation (%) | Voltage Shift (mV) | Potentiation (%) | Voltage Shift (mV) |
| 64 | | 15 | −2.57 | ND | ND |
| 65 | | 22 | −3.79 | ND | ND |
| 69 | | 73 | −3 | ND | ND |
| 70 | | 44 | −2.08 | 34 | −2.42 |

-continued

| | | Electrophysiology Data | | | |
|---|---|---|---|---|---|
| | | Kv3.1 Activity at 10 μM | | Kv3.2 Activity at 10 μM | |
| Example # | Structure | Potentiation (%) | Voltage Shift (mV) | Potentiation (%) | Voltage Shift (mV) |
| 72 | | 33 | −4.25 | ND | ND |
| 73 | | 26 | −1.61 | ND | ND |
| 75 | | 15 | −4.01 | 5 | 0 |
| 77 | | 12 | −0.95 | ND | ND |
| 84 | | 30 | −2.27 | 14 | −1.69 |

-continued

| | | Electrophysiology Data | | | |
|---|---|---|---|---|---|
| | | Kv3.1 Activity at 10 μM | | Kv3.2 Activity at 10 μM | |
| Example # | Structure | Potentiation (%) | Voltage Shift (mV) | Potentiation (%) | Voltage Shift (mV) |
| 89 | | ND | ND | 28 | −2.58 |
| 90 | | 217 | −10.39 | 121 | −7.43 |
| 91 | | 150 | −10.63 | 137 | −6.75 |
| 92 | | 227 | −7.49 | 93 | −5.37 |

-continued

| | | Electrophysiology Data | | | |
|---|---|---|---|---|---|
| | | Kv3.1 Activity at 10 µM | | Kv3.2 Activity at 10 µM | |
| Example # | Structure | Potentiation (%) | Voltage Shift (mV) | Potentiation (%) | Voltage Shift (mV) |
| 93 | 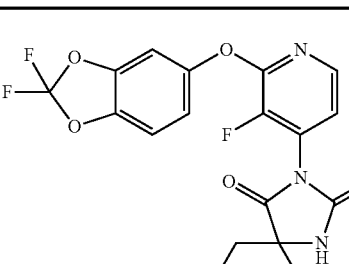 | 142 | −8.79 | 71 | −6.55 |

The invention claimed is:

1. A method of treating cognitive dysfunction and negative symptoms associated with CNS disorders whereby circuitry involving fast spiking PV+ interneurons and production of cortical gamma oscillations are disrupted in a patient in need thereof, including a step of administering to said patient an effective amount of a compound of formula (I):

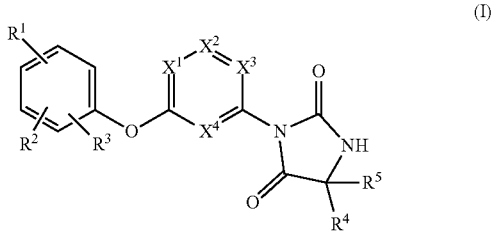

wherein:
$X^1$ is N; $X^2$ and $X^3$ are CH; and $X^4$ is CF;
$R^1$ is phenyl, CN, F, $OCF_3$, $C_1$-$C_3$ alkoxy or $C_1$-$C_5$ alkyl;
$R^2$ is H, $C_1$-$C_5$ alkyl or $C_1$-$C_5$ alkoxy;
$R^3$ is H or $CH_3$; or
$R^1$ and $R^2$ together represent an optionally substituted 5 or 6-membered O-containing heterocyclylene, optionally substituted 5 or 6-membered O-containing heteroarylene, or optionally substituted 5 or 6-membered arylene; and
$R^4$ and $R^5$ are independently H or $C_1$-$C_4$ alkyl, or $R^4$ and $R^5$ together represent an optionally substituted 4-7 membered cycloalkylene or optionally substituted 5-7 membered heterocyclylene;
or a pharmaceutically acceptable salt or solvate thereof and stereoisomers thereof.

2. The method of claim 1, wherein $R_1$ is CN, F, $OCF_3$, $C_1$-$C_3$ alkoxy or $C_1$-$C_5$ alkyl.

3. The method of claim 1, wherein:
$R^2$ is $C_1$-$C_5$ alkyl or $C_1$-$C_5$ alkoxy; or
$R^1$ and $R^2$ together represent an optionally substituted 5-membered O-containing heterocyclyl.

4. The method of claim 1, wherein:
$R^4$ and $R^5$ together represent an optionally substituted 4-7 membered cycloalkylene or optionally substituted 5-7 membered heterocyclylene.

5. The method of claim 1, wherein the group

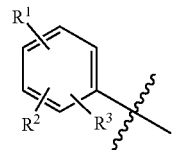

is selected from:

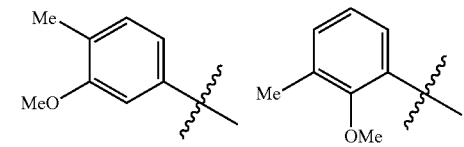

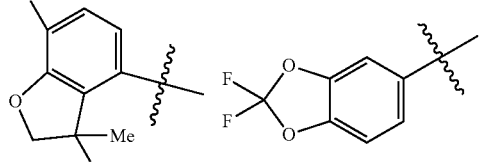

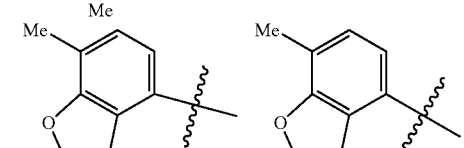

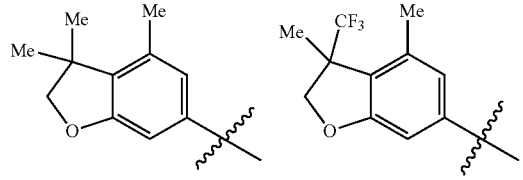

-continued

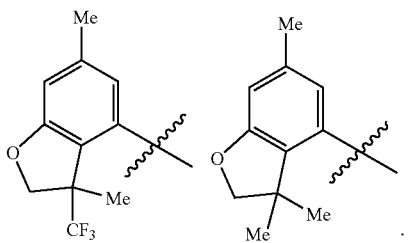

6. The method of claim 1, wherein groups $R^1$ and $R^2$ together are selected from:

(a)
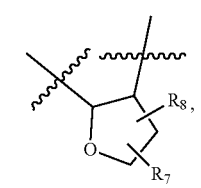

(b)
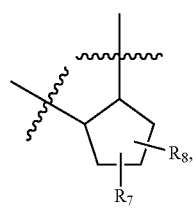

(c)
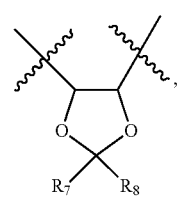

(d)
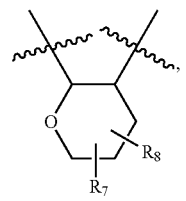

(e)
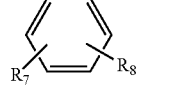, and (f)
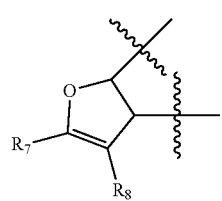

wherein $R_7$ and $R_8$ are independently selected from H, F, CH$_3$ and CF$_3$.

7. A compound of formula (I″b):

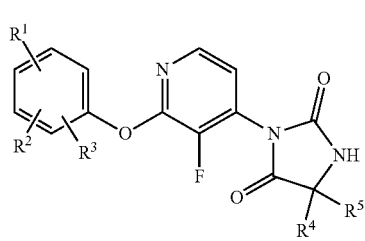

(I″b)

wherein:
$R^1$ is phenyl, CN, F, OCF$_3$, C$_1$-C$_3$ alkoxy or C$_1$-C$_5$ alkyl;
$R^2$ is H, C$_1$-C$_5$ alkyl or C$_1$-C$_5$ alkoxy;
$R^3$ is H or CH$_3$; or
$R^1$ and $R^2$ together represent an optionally substituted 5 or 6-membered O-containing heterocyclylene, optionally substituted 5 or 6-membered O-containing heteroarylene, or optionally substituted 5 or 6-membered arylene; and
$R^4$ and $R^5$ are independently H or C$_1$-C$_4$ alkyl, or $R^4$ and $R^5$ together represent an optionally substituted 4-7 membered cycloalkylene or optionally substituted 5-7 membered heterocyclylene;
or a pharmaceutically acceptable salt or solvate thereof and stereoisomers thereof.

8. The compound according to claim 7, wherein $R^1$ is CN, F, OCF$_3$, C$_1$-C$_3$ alkoxy or C$_1$-C$_5$ alkyl.

9. The compound of formula (I') according to claim 7, wherein
$R^2$ is C$_1$-C$_5$ alkyl or C$_1$-C$_5$ alkoxy; or
$R^1$ and $R^2$ together represent an optionally substituted 5-membered O-containing heterocyclyl.

10. The compound according to claim 7,
wherein $R^4$ and $R^5$ together represent an optionally substituted 4-7 membered cycloalkylene or optionally substituted 5-7 membered heterocyclylene.

11. The compound according to claim 7, wherein the group

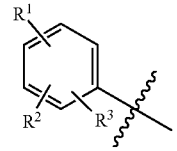

is selected from:

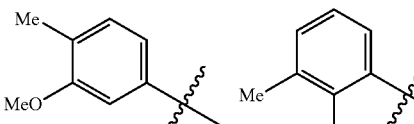

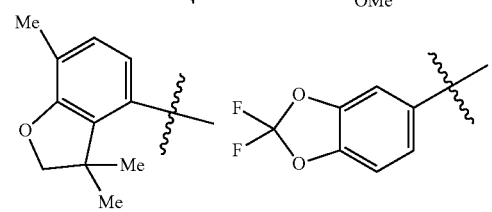

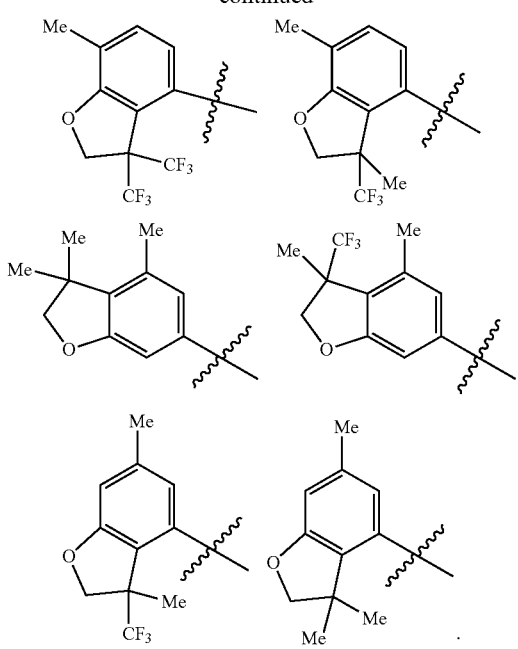
12. The compound according to claim 7, wherein the groups $R^1$ and $R^2$ together are selected from:
(a)
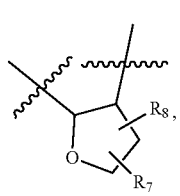
(b)
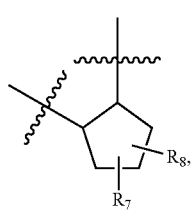
(c)
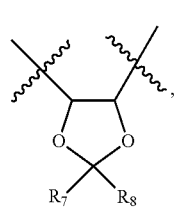
(d)
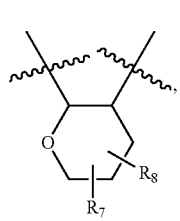
(e)
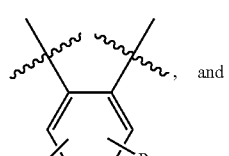, and
(f)
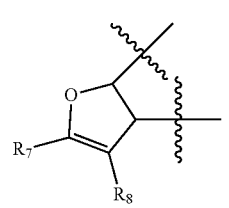
(a)
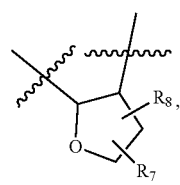
(b)
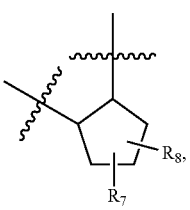
(c)
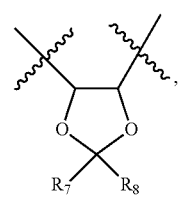
(d)
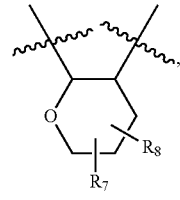
(e)
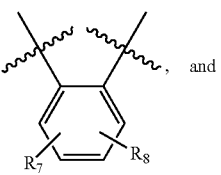, and

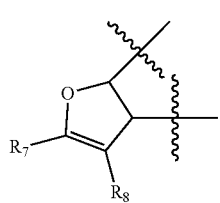 (f)
wherein $R_7$ and $R_8$ are independently selected from H, F, $CH_3$ and $CF_3$.
* * * * *

UNITED STATES PATENT AND TRADEMARK OFFICE
CERTIFICATE OF CORRECTION

PATENT NO. : 12,090,146 B2
APPLICATION NO. : 17/276605
DATED : September 17, 2024
INVENTOR(S) : Hamish Toop et al.

It is certified that error appears in the above-identified patent and that said Letters Patent is hereby corrected as shown below:

In the Claims

In Claim 9, Column 142, Line 31, please delete "The compound of formula (l') according to claim 7" and insert -- The compound according to claim 7 --

In Claim 12, Column 144, Lines 20 through 65, please delete compounds "(a), (b), (c), (d), (e)"

In Claim 12, Column 145, Lines 1 through 10, please delete compound "(f)"

Signed and Sealed this
Twenty-ninth Day of October, 2024

Katherine Kelly Vidal
*Director of the United States Patent and Trademark Office*